(12) United States Patent
Yoshida et al.

(10) Patent No.: US 8,476,301 B2
(45) Date of Patent: Jul. 2, 2013

(54) PYRROLIDIN-3-YLACETIC ACID DERIVATIVE

(75) Inventors: Ichiro Yoshida, Ibaraki (JP); Tadashi Okabe, Ibaraki (JP); Yasunobu Matsumoto, Ibaraki (JP); Nobuhisa Watanabe, Ibaraki (JP); Yoshiaki Ohashi, Ibaraki (JP); Yuji Onizawa, Ibaraki (JP); Hitoshi Harada, Ibaraki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/609,716

(22) Filed: Sep. 11, 2012

(65) Prior Publication Data

US 2013/0065925 A1 Mar. 14, 2013

Related U.S. Application Data

(60) Provisional application No. 61/534,077, filed on Sep. 13, 2011.

(51) Int. Cl.
*A61K 31/445* (2006.01)
*C07D 401/12* (2006.01)

(52) U.S. Cl.
USPC .......................................... 514/326; 546/208

(58) Field of Classification Search
USPC .......................................... 514/326; 546/208
See application file for complete search history.

(56) References Cited

U.S. PATENT DOCUMENTS

| | | | |
|---|---|---|---|
| 5,721,260 A * | 2/1998 | Hohlweg et al. | 514/428 |
| 7,390,490 B1 | 6/2008 | Imai et al. | |
| 7,479,504 B2 * | 1/2009 | Bugianesi et al. | 514/422 |
| 8,088,780 B2 | 1/2012 | Nordvall et al. | |
| 2005/0143372 A1 | 6/2005 | Ghosh et al. | |
| 2007/0142386 A1 | 6/2007 | Nordvall et al. | |
| 2010/0210633 A1 | 8/2010 | Lin et al. | |
| 2010/0317618 A1 | 12/2010 | Guglielmotti et al. | |

FOREIGN PATENT DOCUMENTS

| | | |
|---|---|---|
| JP | 2002-345454 | 12/2002 |
| JP | 2007-507494 | 3/2007 |
| JP | 2008-535834 | 9/2008 |
| JP | 2011-513371 | 4/2011 |
| WO | WO 2006/107257 | 10/2006 |
| WO | WO 2006/107258 | 10/2006 |
| WO | WO 2008/039138 | 4/2008 |
| WO | WO 2008/039139 | 4/2008 |
| WO | WO 2009/120140 | 10/2009 |

OTHER PUBLICATIONS

Kobayashi et al., "Exclusive increase of CX3CR1+CD28−CD4+ T cells in inflammatory bowel disease and their recruitment as intraepithelial lymphocytes," *Inflamm. Bowel Dis.*, 13:837-846 (2007).

Search Report for PCT Application No. PCT/JP2012/073171, Oct. 30, 2012.

Umehara et al., "Fractalkine in vascular biology: from basic research to clinical disease," *Arterioscler. Thromb. Vasc. Biol.*, 24:34-40 (2004).

Arnold et al., "Inflammatory monocytes recruited after skeletal muscle injury switch into antiinflammatory macrophages to support myogenesis," *The Journal of Experimental Medicine*, 204(5):1057-1069 (2007).

Auffray et al., "Monitoring of Blood Vessels and Tissues by a Population of Monocytes with Patrolling Behavior," *Science*, 317(666):666-670 (2007).

Chen et al., "The Amino Terminus and the Third Extracellular Loop of CX3CR1 Contain Determinants Critical for Distinct Receptor Functions," *Molecular Pharmacology*, 69(3):857-865 (2006).

Clark et al., "Inhibition of spinal microglial cathepsin S for the reversal of neuropathic pain," *PNAS*, 104(25):10655-10660 (2007).

Colvin et al., "Intracellular Domains of CXCR3 That Mediate CXCL9, CXCL10, and CXCL11 Function," *The Journal of Biological Chemistry*, 279(29):30219-30227 (2004).

Combadière et al., "Decreased Atherosclerotic Lesion Formation in CX3CR1/Apolipoprotein E Double Knockout Mice," *Circulation*, 107:1009-1016 (2003).

(Continued)

*Primary Examiner* — Dennis Heyer
*Assistant Examiner* — Daniel M Podgorski
(74) *Attorney, Agent, or Firm* — Fish & Richardson P.C.

(57) ABSTRACT

A compound represented by formula (1) or a pharmaceutically acceptable salt thereof has an inhibitory effect in the fractalkine-CX3CR1 pathway:

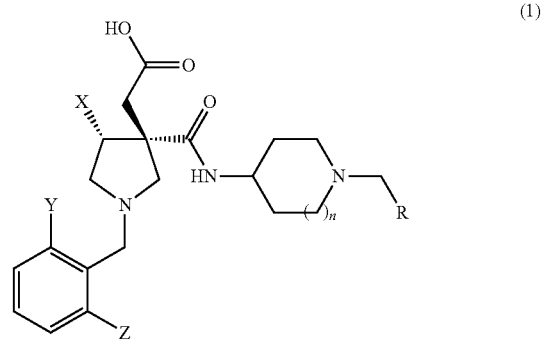

(1)

wherein R represents a $C_{1-6}$ alkyl group unsubstituted or having 1 to 3 substituents selected from Substituent Group A, a $C_{3-8}$ cycloalkyl group unsubstituted or having 1 to 3 substituents selected from Substituent Group A, or a $C_{3-8}$ cycloalkenyl group unsubstituted or having 1 to 3 substituents selected from Substituent Group A, X represents a $C_{1-6}$ alkyl group, Y and Z are the same or different from each other and each represents a halogen atom or a $C_{1-6}$ alkyl group unsubstituted or having 1 to 3 substituents selected from Substituent Group B, n represents 0 or 1, Substituent Group A consists of halogen atoms, and Substituent Group B consists of halogen atoms.

24 Claims, 4 Drawing Sheets

OTHER PUBLICATIONS

Feng et al., Prevention of crescentic glomerulonephritis by immunoneutralization of the fractalkine receptor $CX_3CR1$ *Rapid Communication*, Kidney International, 56:612-620 (1999).

Fong et al., "$CX_3CR1$ Tyrosine Sulfation Enhances Fractalkine-induced Cell Adhesion," *Journal of Biological Chemistry*, 277(22):19418-19423 (2002).

Fong et al., "Fractalkine and $CX_3CR1$ Mediate a Novel Mechanism of Leukocyte Capture, Firm Adhesion, and Activation under Physiologic Flow," *J. Exp. Med.*, 188(8):1413-1419 (1998).

Garin et al., "Cloning and functional characterization of the human fractalkine receptor promoter regions," *Biochem. J.*, 368:753-760 (2002).

Garin et al., "Two Novel Fully Functional Isoforms of $CX_3CR1$ Are Potent HIV Coreceptors," *The Journal of Immunology*, 171:5305-5312 (2003).

Hulshof et al., "$CX_3CL1$ and $CX_3CR1$ expression in human brain tissue: noninflammatory control versus multiple sclerosis," *Journal of Neuropathology & Experimental Neurolo*, 62(9):899-907 (2003).

Hurst et al., "Expression of ADAM-17, TIMP-3 and fractalkine in the human adult brain endothelial cell line, hCMEC/D3, following pro-inflammatory cytokine treatment," *Journal of Neuroimmunology*, 210:108-112 (2009).

Imai et al., "Identification and Molecular Characterization of Fractalkine Receptor $CX_3CR1$,which Mediates Both Leukocyte Migration and Adhesion," *Cell*, 91:521-530 (1997).

Infante-Duarte et al., "Frequency of blood $CX_3CR1$-positive natural killer cells correlates with disease activity in multiple sclerosis patients," *The FASEB Journal*, p. 1 -p19 (2005).

Inoue et al., "Antagonist of Fractalkine (CX3CL1) Delays the Initiation and Ameliorates the Progression of Lupus Nephritis in MRL/*lpr* Mice," *Arthritis & Rheumatism*, 52(5):1522-1533 (2005).

Ito et al., "Fractalkine expression and the recruitment of $CX_3CR1^+$cells in the prolonged mesangial proliferative glomerulonephritis," *Kidney International*, 61:2044-2057 (2002).

Kastenbauer et al., "CSF and serum levels of soluble fractalkine ($CX_3CL1$) in inflammatory diseases of the nervous system," *Journal of Neuroimmunology*, 137:210-217 (2003).

Kenakin, "New Concepts in Drug Discovery: Collateral Efficacy and Permissive Antagonism," *Nature Reviews, Drug Discovery*, 4:919-927, (2005).

Kobayashi et al., "Exclusive Increase of $CX3CR1^+CD28^-CD4^+$T Cells in Inflammatory Bowel Disease and Their Recruitment as Intraepithelial Lymphocytes," *Inflamm Bowel Dis*, 13(7):837-846 (2007).

Komocsi et al., "Peripheral Blood and Granuloma $CD4^+CD28^-$T Cells Are a Major Source of Interferon-γ and Tumor Necrosis Factor-60 in Wegener's Granulomatosis," *American Journal of Pathology*, 160(5):1717-1724 (2002).

Lesnik et al., "Decreased atherosclerosis in $CX_3CR1^{-/-}$ mice reveals a role for fractalkine in atherogenesis," *The Journal of Clinical Investigation*, 111(3):333-340 (2003).

Mack et al., "Aminooxypentane-RANTES Induces CCR5 Internalization but Inhibits Recycling: A Novel Inhibitory Mechanism of HIV Infectivity," *J. Exp. Med*, 187(8):1215-1224 (1998).

Muehlhoefer et al., "Fractalkine Is an Epithelial and Endothelial Cell-Derived Chemoattractant for Intraepithelial Lymphocytes in the Small Intestinal Mucosa," *The Journal of Immunology*, 164:3368-3376 (2000).

Nakajima et al., "T-Cell-Mediated Lysis of Endothelial Cells in Acute Coronary Syndromes," *Circulation*, 105:570-575 (2002).

Nanki et al, "Inhibition of Fractalkine Ameliorates Murine Collagen-Induced Arthritis," *Journal of Immunology*, 173:7010-7016 (2004).

Nanki et al., "Migration of CX3CR1-Positive T Cells Producing Type 1 Cytokines and Cytotoxic Molecules Into the Synovium of Patients With Rheumatoid Arthritis," *Arthritis & Rheumatism*, 46(11):2878-2883 (2002).

Neel et al., "Chemokine receptor internalization and intracellular trafficking," *Cytokine & Growth Factor Reviews*, 16:637-658 (2005).

Odai et al., "Correlation of CX3CL1 and CX3CR1 Levels with Response to Infliximab Therapy in Patients with Rheumatoid Arthritis," *The Journal of Rheumatology*, 36(6):1158-1165 (2009).

Otero et al., "Opposite Fate of Endocytosed CCR7 and Its Ligands: Recycling versus Degradation," *The Journal of Immunology*, 177:2314-2323 (2006).

Pujari et al., "Expression of fractalkine in plasma of patients with relapsing-remitting multiple sclerosis," *Immunology*—Part II, 1 p., (2006).

Robinson et al., "A Role for Fractalkine and Its Receptor ($CX_3CR1$) in Cardiac Allograft Rejection," *The Journal of Immunology*, 165:6067-6072 (2000).

Ruth et al., "Fractalkine, a Novel Chemokine in Rheumatoid Arthritis and in Rat Adjuvant-Induced Arthritis," *Arthritis & Rheumatism*, 44(7):1568-1581 (2001).

Ruth et al., "Selective Lymphocyte Chemokine Receptor Expression in the Rheumatoid Joint," *Arthritis & Rheumatism*, 44(12):2750-2760 (2001).

Sabroe et al., "A Small Molecule Antagonist of Chemokine Receptors CCR1 and CCR3, Potent Inhibition Of Eosinophil Function And CCR3-Mediated HIV-1 Entry," *The Journal Of Biological Chemistry*, 275(34):25985-25992 (2000).

Saita et al., "Structural Basis for the Interaction of CCR5 with a Small Molecule, Functionally Selective CCR5 Agonist," *The Journal of Immunology*, 177:3116-3122 (2006).

Sans et al., "Enhanced Recruitment of CX3CR1 T Cells by Mucosal Endothelial Cell—Derived Fractalkine in Inflammatory Bowel Disease," *Gastroenterology*, 132:139-153, (2007).

Sawai et al., "Fractalkine Mediates T Cell—Dependent Proliferation of Synovial Fibroblasts in Rheumatoid Arthritis," *Arthritis & Rheumatism*, 56(10):3215-3225 (2007).

Sawai et al., "T Cell Costimulation by Fractalkine-Expressing Synoviocytes in Rheumatoid Arthritis," *Arthritis & Rheumatism*, 52(5):1392-1401 (2005).

Sunnemark et al., "Differential Expression of the Chemokine Receptors $CX_3CR1$ and CCR1 by Microglia and Macrophages in Myelin-Oligodendrocyte- Glycoprotein-Induced Experimental Autoimmune Encephalomyelitis," *Brain Pathol*, 13:617-629 (2003).

Suzuki et al , "Inhibition of CX3CL1 (Fractalkine) Improves Experimental Autoimmune Myositis in Sjl/J Mice," *The Journal of Immunology*, 175:6987-6996 (2005).

Ueha et al., "Intervention of MAdCAM-1 or fractalkine alleviates graft-versus-host reaction associated intestinal injury while preserving graft-versus-tumor effects," *Journal of Leukocyte Biology*, 81:176-185 (2007).

Wong et al., "Characterization of fractalkine (CX3CL1) and CX3CR1 in human coronary arteries with native atherosclerosis, diabetes mellitus, and transplant vascular disease," *Cardiovascular Pathology*, 11:332-338 (2002).

Yoneda et al., "Fractalkine-Mediated Endothelial Cell Injury by Nk Cells," *the Journal of Immunology*, 164:4055-4062 (2000).

Yoneda et al., "Membrane-bound form of fractalkine induces IFN-γ production by NK cells," *Eur. J Immunol.*, 33:53-p58 (2003).

Zhuang et al., "Role of the CX3CR1/p38 MAPK pathway in spinal microglia for the development of neuropathic pain following nerve injury-induced cleavage of fractalkine," *Brain, Behavior, and Immunity*, 21:642-651 (2007).

\* cited by examiner

PYRROLIDIN-3-YLACETIC ACID DERIVATIVE

CROSS-REFERENCE TO RELATED APPLICATIONS

This application claims the benefit of U.S. provisional application No. 61/534,077 filed on Sep. 13, 2011, the disclosure of which is herein incorporated by reference in its entirety.

BACKGROUND OF THE INVENTION

1. Field of the Invention

The present invention relates to a pyrrolidin-3-ylacetic acid derivative. More particularly, the present invention relates to a pyrrolidin-3-ylacetic acid derivative having availability as a therapeutic agent for inflammatory bowel disease.

2. Related Background Art

Chemokines are major cell migration factors and regulate infiltration of lymphocytes into tissues through the enhancement of cell movement and the activation of adhesion molecules. Chemokines are classified into four subfamilies of CC, CXC, C and CX3C based on their sequences of the first two cysteine residues.

Fractalkine is the sole CX3C chemokine member and has distinct characteristics in its structure and functions which are not found in other chemokines. Fractalkine binds to a receptor, CX3CR1, which can mediate strong adhesion without mediation of selectin or integrin even in the presence of a physiological blood flow. This means that the fractalkine-CX3CR1 system mediates multi-stage infiltration mechanism through selectin or integrin by only a one-stage reaction.

Expression of fractalkine on vascular endothelial cells is induced by inflammatory cytokines TNF and IL-1. On the other hand, CX3CR1 is expressed on monocytes, almost all NK cells and some T cells, but is not expressed on neutrophils. Therefore, the fractalkine-CX3CR1 system is considered to be an extremely effective mechanism to mobilize immune cells onto the endothelial cells of damaged tissues or into the tissues.

With regard to the relation between the fractalkine-CX3CR1 system and pathologies, it is suggested that the fractalkine-CX3CR1 system is involved in the development and pathologies of autoimmune diseases such as rheumatoid arthritis, inflammatory bowel disease, lupus nephritis and multiple sclerosis (Non Patent Literature 1). In particular, with regard to inflammatory bowel disease, it is reported that expression of fractalkine is enhanced at inflammatory sites of colonic tissues of patients and that CX3CR1 plays an important role in the infiltration of immune cells into the colon tissue (Non Patent Literature 2).

Antibodies described in Patent Literature 1 and low molecular weight compounds described in Patent Literatures 2 to 6 have been previously known as fractalkine inhibitors.

In addition, compounds described in Patent Literature 7 are described to be useful as chemokine CCR2 receptor antagonists, but differ in the target chemokine family from such inhibitors.

CITATION LIST

Patent Literature

Patent Literature 1: Japanese Patent Application Laid-Open Publication No. 2002-345454
Patent Literature 2: WO 2006/107257
Patent Literature 3: WO 2006/107258
Patent Literature 4: WO 2008/039138
Patent Literature 5: WO 2008/039139
Patent Literature 6: WO 2009/120140
Patent Literature 7: U.S. Patent Application Laid-Open Publication No. 2010/0210633

Non Patent Literature

Non Patent Literature 1: Umehara et al., "Fractalkine in Vascular Biology", Arterioscler. Thromb. Vase. Biol., Vol. 24, pp. 34-40, 2004
Non Patent Literature 2: Kobayashi et al., "Exclusive Increase of CX3CR1_CD28_CD4_T Cells in Inflammatory Bowel Disease and Their Recruitment as Intraepithelial Lymphocytes", Inflamm. Bowel. Dis., Vol. 13, pp. 837-846, 2007

SUMMARY OF INVENTION

An object of the present invention is to provide a compound having an inhibitory effect in the fractalkine-CX3CR1 pathway.

As a result of intensive studies, the present inventors have found the present invention. Specifically, the present invention relates to

[1] A compound represented by formula (1) or pharmaceutically acceptable salt thereof:

[Chemical Formula 1]

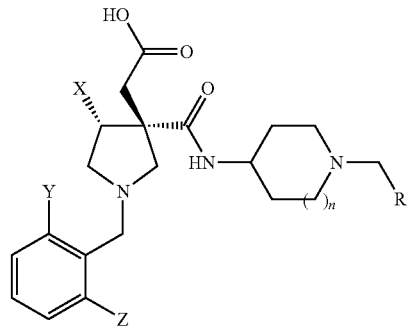

(1)

wherein R represents a $C_{1-6}$ alkyl group unsubstituted or having 1 to 3 substituents selected from Substituent Group A, a $C_{3-8}$ cycloalkyl group unsubstituted or having 1 to 3 substituents selected from Substituent Group A, or a $C_{3-8}$ cycloalkenyl group unsubstituted or having 1 to 3 substituents selected from Substituent Group A,
X represents a $C_{1-6}$ alkyl group,
Y and Z are the same or different from each other and each represents a halogen atom or a $C_{1-6}$ alkyl group unsubstituted or having 1 to 3 substituents selected from Substituent Group B,
n represents 0 or 1,
Substituent Group A consists of halogen atoms, and
Substituent Group B consists of halogen atoms;
[2] The compound or pharmaceutically acceptable salt thereof according to [1], wherein R is a fluorobutyl group, a pentyl group, a cyclohexyl group, a difluorocyclohexyl group, a cyclopentenyl group or a cyclohexenyl group;
[3] The compound or pharmaceutically acceptable salt thereof according to [1] or [2], wherein X is a methyl group;
[4] The compound or pharmaceutically acceptable salt thereof according to any one of [1] to [3], wherein Y is a chlorine atom;

[5] The compound or pharmaceutically acceptable salt thereof according to any one of [1] to [4], wherein Z is a chlorine atom, a methyl group, a difluoromethyl group or a trifluoromethyl group;

[6] The compound or pharmaceutically acceptable salt thereof according to any one of [1] to [5], wherein n is 1;

[7] A compound selected from the group consisting of:
2-[(3S,4R)-1-{[2-chloro-6-(trifluoromethyl)phenyl]methyl}-3-{[1-(2-fluoropentyl)piperidin-4-yl]carbamoyl}-4-methylpyrrolidin-3-yl]acetic acid,
2-[(3S,4R)-1-[(2,6-dichlorophenyl)methyl]-3-({1-[(4,4-difluorocyclohexyl)methyl]piperidin-4-yl}carbamoyl)-4-methylpyrrolidin-3-yl]acetic acid,
2-[(3S,4R)-1-{[2-chloro-6-(trifluoromethyl)phenyl]methyl}-3-{[1-(cyclohex-1-en-1-ylmethyl)piperidin-4-yl]carbamoyl}-4-methylpyrrolidin-3-yl]acetic acid,
2-[(3S,4R)-1-[(2-chloro-6-methylphenyl)methyl]-3-{[1-(cyclohex-1-en-1-ylmethyl)piperidin-4-yl]carbamoyl}-4-methylpyrrolidin-3-yl]acetic acid,
2-[(3S,4R)-1-{[2-chloro-6-(trifluoromethyl)phenyl]methyl}-3-{[1-(cyclopent-1-en-1-ylmethyl)piperidin-4-yl]carbamoyl}-4-methylpyrrolidin-3-yl]acetic acid,
2-[(3S,4R)-1-[(2-chloro-6-methylphenyl)methyl]-3-{[(1-cyclopent-1-en-1-ylmethyl)piperidin-4-yl]carbamoyl}-4-methylpyrrolidin-3-yl]acetic acid,
2-[(3S,4R)-(3-{[(3S)-1-(cyclohex-1-en-1-ylmethyl)pyrrolidin-3-yl]carbamoyl}-1-[(2,6-dichlorophenyl)methyl]-4-methylpyrrolidin-3-yl]acetic acid,
2-[(3S,4R)-1-{[2-chloro-6-(difluoromethyl)phenyl]methyl}-3-[(1-hexylpiperidin-4-yl)carbamoyl]-4-methylpyrrolidin-3-yl]acetic acid,
2-[(3S,4R)-3-{[(1-cyclohex-1-en-1-ylmethyl)piperidin-4-yl]carbamoyl}-1-[(2,6-dichlorophenyl)methyl]-4-methylpyrrolidin-3-yl]acetic acid,
2-[(3S,4R)-1-{[2-chloro-6-(difluoromethyl)phenyl]methyl}-3-{[1-(cyclohex-1-en-1-ylmethyl)piperidin-4-yl]carbamoyl}-4-methylpyrrolidin-3-yl]acetic acid,
2-[(3S,4R)-1-{[2-chloro-6-(difluoromethyl)phenyl]methyl}-3-{[1-(cyclopent-1-en-1-ylmethyl)piperidin-4-yl]carbamoyl}-4-methylpyrrolidin-3-yl]acetic acid and
2-[(3S,4R)-1-{[2-chloro-6-(difluoromethyl)phenyl]methyl}-3-{[1-(cyclohexylmethyl)piperidin-4-yl]carbamoyl}-4-methylpyrrolidin-3-yl]acetic acid,
or a pharmaceutically acceptable salt thereof;

[8] A medicine comprising the compound or pharmaceutically acceptable salt thereof according to any one of [1] to [7] as an active ingredient;

[9] A therapeutic agent for inflammatory bowel disease comprising the compound or pharmaceutically acceptable salt thereof according to any one of [1] to [7] as an active ingredient;

[10] The therapeutic agent according to [9], wherein the inflammatory bowel disease is ulcerative colitis or Crohn's disease;

[11] A fractalkine-CX3CR1 pathway inhibitor comprising the compound or pharmaceutically acceptable salt thereof according to any one of [1] to [7] as an active ingredient;

[12] A fractalkine inhibitor comprising the compound or pharmaceutically acceptable salt thereof according to any one of [1] to [7] as an active ingredient;

[13] A CX3CR1 inhibitor comprising the compound or pharmaceutically acceptable salt thereof according to any one of [1] to [7] as an active ingredient;

[14] A method for treating inflammatory bowel disease comprising administering the compound or pharmaceutically acceptable salt thereof according to any one of [1] to [7] to a patient;

[15] The method according to [14], wherein the inflammatory bowel disease is ulcerative colitis or Crohn's disease;

[16] A method for inhibiting the fractalkine-CX3CR1 pathway comprising administering the compound or pharmaceutically acceptable salt thereof according to any one of [1] to [7] to a patient;

[17] A method for inhibiting fractalkine comprising administering the compound or pharmaceutically acceptable salt thereof according to any one of [1] to [7] to a patient;

[18] A method for inhibiting CX3CR1 comprising administering the compound or pharmaceutically acceptable salt thereof according to any one of [1] to [7] to a patient;

[19] The compound or pharmaceutically acceptable salt thereof according to any one of [1] to [7], which is used for the treatment of inflammatory bowel disease;

[20] The compound or pharmaceutically acceptable salt thereof according to [19], wherein the inflammatory bowel disease is ulcerative colitis or Crohn's disease;

[21] The compound or pharmaceutically acceptable salt thereof according to any one of [1] to [7], which is used for the inhibition of the fractalkine-CX3CR1 pathway;

[22] The compound or pharmaceutically acceptable salt thereof according to any one of [1] to [7], which is used for the inhibition of fractalkine;

[23] The compound or pharmaceutically acceptable salt thereof according to any one of [1] to [7], which is used for the inhibition of CX3CR1;

[24] Use of the compound or pharmaceutically acceptable salt thereof according to any one of [1] to [7] in the manufacture of a therapeutic agent for inflammatory bowel disease;

[25] The use according to [24], wherein the inflammatory bowel disease is ulcerative colitis or Crohn's disease;

[26] Use of the compound or pharmaceutically acceptable salt thereof according to any one of [1] to [7] in the manufacture of a fractalkine-CX3CR1 pathway inhibitor;

[27] Use of the compound or pharmaceutically acceptable salt thereof according to any one of [1] to [7] in the manufacture of a fractalkine inhibitor; and

[28] Use of the compound or pharmaceutically acceptable salt thereof according to any one of [1] to [7] in the manufacture of a CX3CR1 inhibitor.

ADVANTAGEOUS EFFECTS OF INVENTION

According to the results of the tests described below, the compounds according to the present invention have an inhibitory effect in the fractalkine-CX3CR1 pathway. Therefore, the compounds according to the present invention have availability as therapeutic agents for inflammatory bowel disease.

DESCRIPTION OF THE PREFERRED EMBODIMENTS

Figure 1:
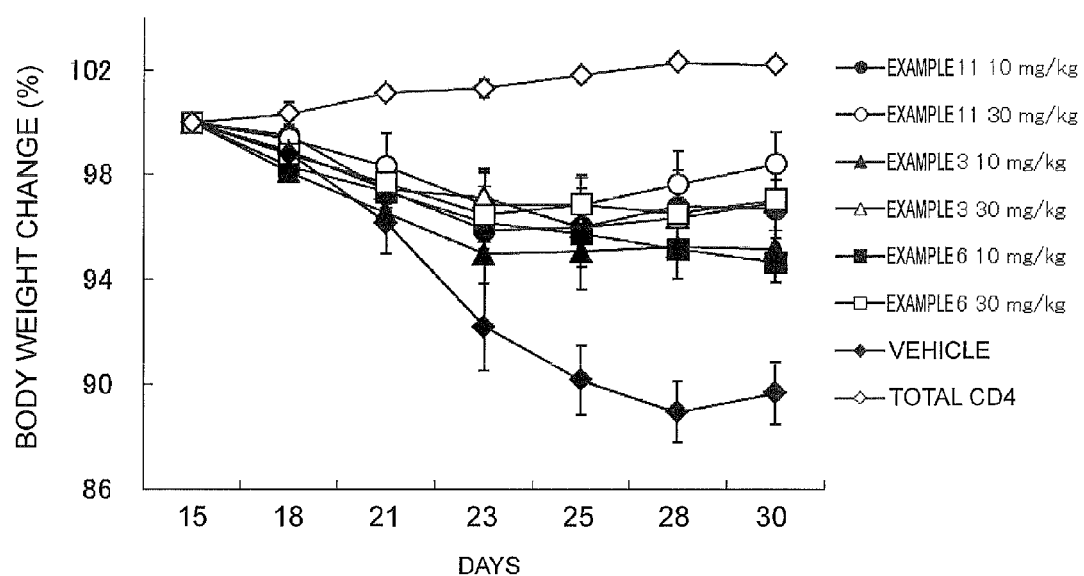
FIG. 1 shows a graph showing the results of Test Example 2 for the compounds of Examples 3, 6 and 11.

The present invention will be described in detail below.

In the present specification, the present invention is not limited to a particular crystal form but may include any one of crystal forms or mixtures thereof, although crystal polymorphs may exist. The present invention also includes amorphous forms, and the compounds according to the present invention include anhydrides, hydrates and solvates.

Hereinafter, the meanings of terms, symbols and the like described in the present specification will be described, and the present invention will be described in detail.

The "$C_{1-6}$ alkyl group" in the present specification means a linear or branched alkyl group having 1 to 6 carbon atoms, and examples include a methyl group, an ethyl group, a 1-propyl group, a 2-propyl group, a 2-methyl-1-propyl group, a 2-methyl-2 propyl group, a 1-butyl group, a 2-butyl group, a 1-pentyl group, a 2-pentyl group, a 3-pentyl group, a 1-hexyl group, a 2-hexyl group and a 3-hexyl group.

The "$C_{3-8}$ cycloalkyl group" in the present specification means a monocyclic saturated aliphatic hydrocarbon group having 3 to 8 carbon atoms, and examples include a cyclopropyl group, a cyclobutyl group, a cyclopentyl group, a cyclohexyl group, a cycloheptyl group and a cyclooctyl group.

The "$C_{3-8}$ cycloalkenyl group" in the present specification means a monocyclic aliphatic hydrocarbon group having 3 to 8 carbon atoms and containing 1 to 4 double bonds in the ring, and examples include a cyclopropenyl group, a cyclobutenyl group, a cyclopentenyl group, a cyclohexenyl group, a cycloheptenyl group and a cyclooctenyl group.

The "halogen atom" in the present specification means a fluorine atom, a chlorine atom, a bromine atom or an iodine atom.

R in the compound represented by formula (1) represents a $C_{1-6}$ alkyl group unsubstituted or having 1 to 3 substituents selected from Substituent Group A, a $C_{3-8}$ cycloalkyl group unsubstituted or having 1 to 3 substituents selected from Substituent Group A, or a $C_{3-8}$ cycloalkenyl group unsubstituted or having 1 to 3 substituents selected from Substituent Group A. Preferably, R represents a fluorobutyl group, a pentyl group, a cyclohexyl group, a difluorocyclohexyl group, a cyclopentenyl group or a cyclohexenyl group.

X in the compound represented by formula (1) represents a $C_{1-6}$ alkyl group. Preferably, X represents a methyl group.

Y and Z in the compound represented by formula (1) are the same or different from each other and each represents a halogen atom or a $C_{1-6}$ alkyl group unsubstituted or having 1 to 3 substituents selected from Substituent Group B. Preferably, Y represents a chlorine atom. Preferably, Z represents a chlorine atom, a methyl group, a difluoromethyl group or a trifluoromethyl group.

n in the compound represented by formula (1) represents 0 or 1, and preferably represents 1.

Substituent Group A consists of halogen atoms, and is preferably a fluorine atom.

Substituent Group B consists of halogen atoms, and is preferably a fluorine atom, a chlorine atom or a bromine atom, more preferably a fluorine atom.

The "pharmaceutically acceptable salt" in the present specification is not particularly limited insofar as it forms a salt with the compound represented by formula (1) and is pharmaceutically acceptable, and examples include inorganic acid salts, organic acid salts, inorganic base salts, organic base salts, and acidic or basic amino acid salts.

Preferred examples of inorganic acid salts include hydrochlorides, hydrobromides, sulfates, nitrates and phosphates, and preferred examples of organic acid salts include acetates, succinates, fumarates, maleates, tartrates, citrates, lactates, stearates, benzoates, mandelates, methanesulfonates, ethanesulfonates, p-toluenesulfonates and benzenesulfonates.

Preferred examples of inorganic base salts include alkali metal salts such as sodium salts and potassium salts, alkaline earth metal salts such as calcium salts and magnesium salts, aluminum salts and ammonium salts, and preferred examples of organic base salts include diethylamine salts, diethanolamine salts, meglumine salts and N,N'-dibenzylethylenediamine salts.

Preferred examples of acidic amino acid salts include aspartates and glutamates, and preferred examples of basic amino acid salts include arginine salts, lysine salts and ornithine salts.

The compound represented by formula (1) can be produced by the method described below, and can also be produced by an improvement of the method described below by those skilled in the art based on the common knowledge. However, the method for producing the compound represented by formula (1) is not limited to these methods.

The compound represented by formula (1) (hereinafter also referred to as Compound (1)) can be produced through Process A, Process B and Process C described below in detail using an intermediate represented by formula (2) as a starting material.

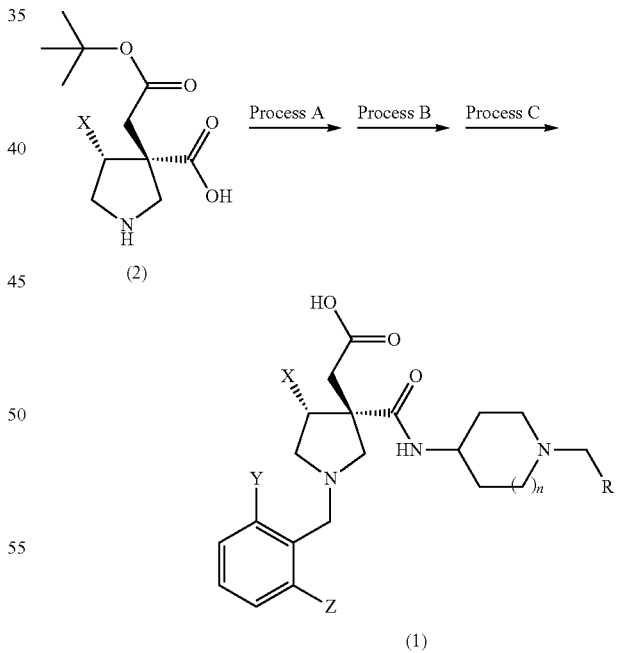

[Chemical Formula 2]

[In the scheme, R, X, Y, Z and n are as defined above.]

The sequence of the respective processes may be changed as appropriate based on the common knowledge of those skilled in the art. Each process may be followed by purification methods known to the skilled in the art, or may progress to next process without isolation and purification.

(Process A) Amidation (Process B) Arylmethylation

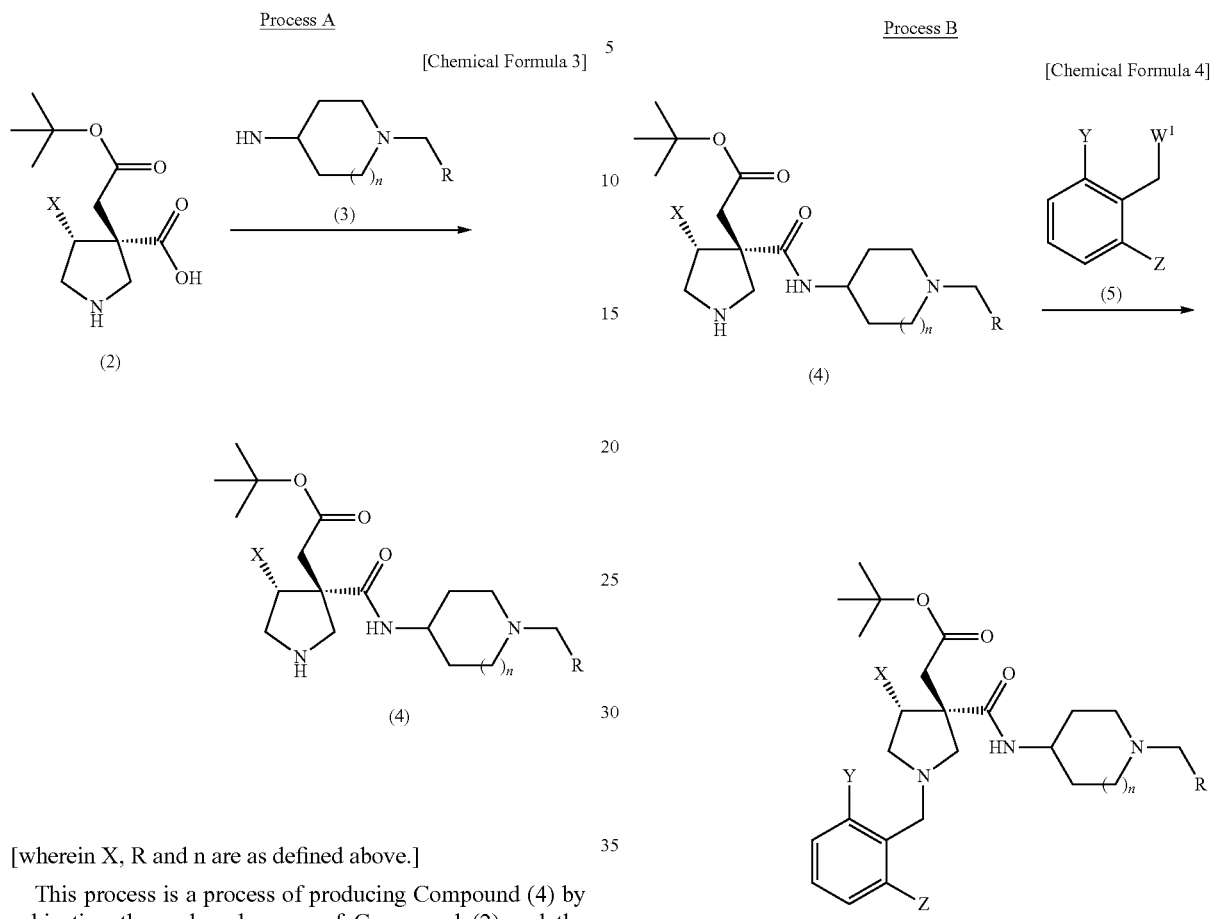

[wherein X, R and n are as defined above.]

This process is a process of producing Compound (4) by subjecting the carboxyl group of Compound (2) and the amino group of Compound (3) to dehydration condensation in an inert solvent in the presence of a condensing agent and a base to form an amide bond.

The solvent used is not particularly limited insofar as it dissolves the starting material to some degree and does not inhibit the reaction, and examples include amides such as N,N-dimethylformamide, N,N-dimethylacetamide and 1-methylpyrrolidinone, ethers such as tetrahydrofuran, and sulfoxides such as dimethyl sulfoxide, with N,N-dimethylformamide being preferred.

Examples of the condensing agent used include benzotriazol-1-yloxytris(pyrrolidino)phosphonium hexafluorophosphate (hereinafter called PyBOP), bis(2-oxo-3-oxazolidinyl)phosphinic chloride (hereinafter called BOP-Cl), benzotriazol-1-yloxytris(dimethylamino)phosphonium hexafluorophosphate, 2-(benzotriazol-1-yl)-1,1,3,3-tetramethyluronium hexafluorophosphate and diethyl cyanophosphate, with PyBOP or BOP-Cl being preferred and PyBOP being most preferred.

Examples of the base used include triethylamine and diisopropylethylamine, with triethylamine being preferred.

The reaction temperature varies depending on the starting material, solvent, condensing agent and base, but is usually −20° C. to 100° C., preferably 0° C. to 60° C.

The reaction time varies depending on the starting material, solvent, condensing agent and base, but is usually 30 minutes to five days, preferably one hour to three days.

[wherein R, X, Y, Z and n are as defined above, and $W^1$ represents a halogen atom, an alkylsulfonyloxy group or an arylsulfonyloxy group.]

This process is a process of producing Compound (6) by reacting Compound (4) with Compound (5) in an inert solvent in the presence of a base.

The solvent used is not particularly limited insofar as it dissolves the starting material to some degree and does not inhibit the reaction, and examples include amides such as N,N-dimethylformamide, N,N-dimethylacetamide and 1-methylpyrrolidinone, and sulfoxides such as dimethyl sulfoxide, with N,N-dimethylformamide being preferred.

Examples of the base used include inorganic bases such as sodium carbonate and potassium carbonate, with potassium carbonate being preferred.

The reaction temperature varies depending on the starting material, solvent and base, but is usually −20° C. to 100° C., preferably 0° C. to 60° C.

The reaction time varies depending on the starting material, solvent and base, but is usually 30 minutes to five days, preferably 1 to 24 hours.

(Process C) Elimination of Tert-Butyl Group

Process C

[Chemical Formula 5]

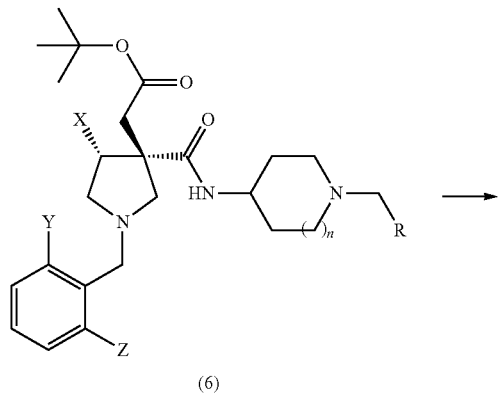

(6)

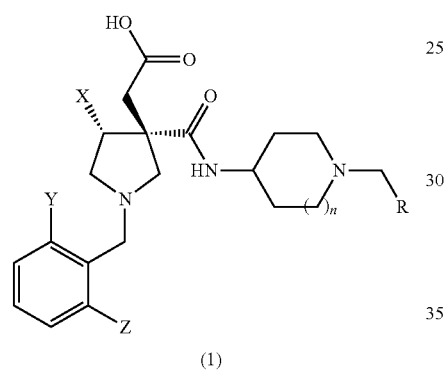

(1)

[wherein R, X, Y, Z and n are as defined above.]

This process is a process of producing Compound (1) by reacting Compound (6) with an acid in the absence of a solvent or in an inert solvent.

The solvent used is not particularly limited insofar as it dissolves the starting material to some degree and does not inhibit the reaction, and examples include halogenated hydrocarbons such as dichloromethane and chloroform, toluene, dioxane, water and a mixed solvent of dioxane and water, with dichloromethane being preferred.

Examples of the acid used include carboxylic acids such as trifluoroacetic acid, and inorganic acids such as hydrochloric acid, with trifluoroacetic acid being preferred.

The reaction temperature varies depending on the starting material, solvent and acid, but is usually −20° C. to 100° C., preferably 0° C. to 40° C.

The reaction time varies depending on the starting material, solvent and acid, but is usually 30 minutes to one day, preferably 1 to 12 hours.

A production method through Process D and Process F may also be used as another method for producing Compound (1).

(Process D) Reductive Amination

Process D

[Chemical Formula 6]

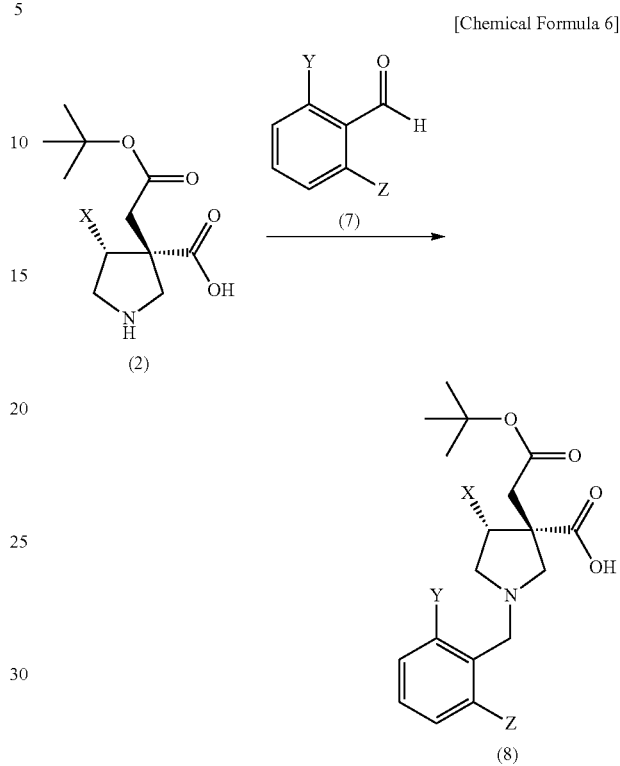

[wherein X, Y and Z are as defined above.]

This process is a process of producing Compound (8) by reacting Compound (2) with Compound (7) and a reducing agent in an inert solvent in the presence or absence of an acid.

The solvent used is not particularly limited insofar as it dissolves the starting material to some degree and does not inhibit the reaction, and examples include ethers such as tetrahydrofuran, and alcohols such as methanol and ethanol, with tetrahydrofuran or methanol being preferred.

Examples of the reducing agent used include borohydride compounds such as sodium triacetoxyborohydride, sodium cyanoborohydride and sodium borohydride, with sodium triacetoxyborohydride being preferred.

The acid may or may not be used in this process, and if used, the acid used is not particularly limited insofar as it does not inhibit the reaction, and is preferably acetic acid.

The reaction temperature varies depending on the starting material, solvent, reducing agent and acid, but is usually −20° C. to 100° C., preferably 0° C. to 60° C.

The reaction time varies depending on the starting material, solvent, reducing agent and acid, but is usually 30 minutes to five days, preferably 1 to 48 hours.

Even when Compound (2) being the starting material forms a salt, the reaction can be allowed to proceed by adding an organic amine such as triethylamine in an amount of one or more equivalents to the amount of the carboxylic acid forming the salt.

(Process E) Hydrogenation

Compound (4) in which the arylmethyl group is eliminated can be obtained by subjecting Compound (6) obtained in the above Process B to hydrogenation reaction. Compound (4) can further be converted by Process B to Compound (6) to which an arylmethyl group having a different substituent is added.

[Chemical Formula 7]

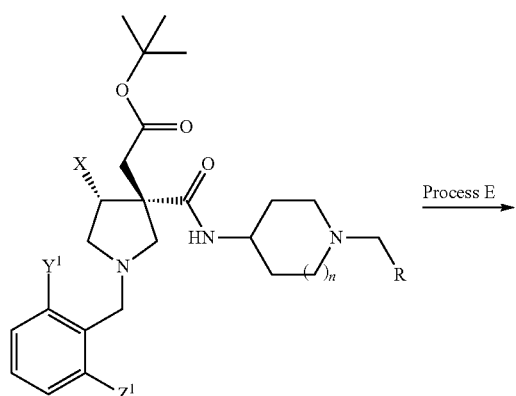

(6)

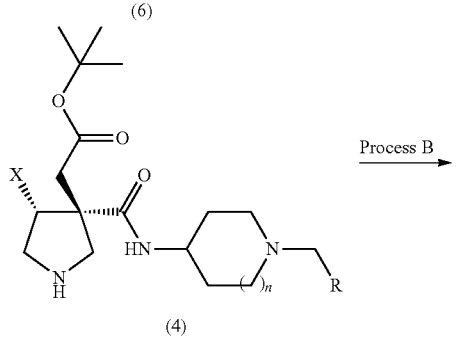

(4)

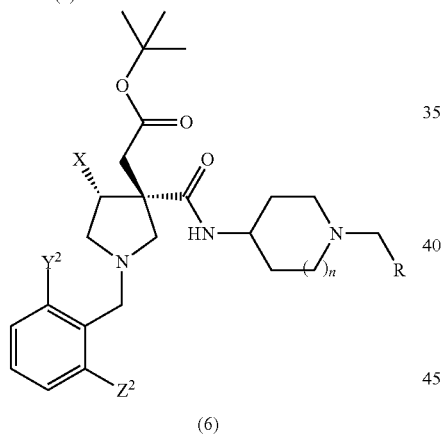

(6)

[wherein R, Z and n are as defined above, $Y^1$ and $Y^2$ have the same meaning as in Y above, and $Z^1$ and $Z^2$ have the same meaning as in Z above.]

This process is a process of producing Compound (4) by reacting Compound (6) with hydrogen in an inert solvent in the presence of a reduction catalyst to remove the arylmethyl group.

The solvent used is not particularly limited insofar as it dissolves the starting material to some degree and does not inhibit the reaction, and examples include alcohols such as methanol and ethanol, ethers such as tetrahydrofuran, dioxane and dimethoxyethane, and organic acid esters such as ethyl acetate, with ethers, alcohols, organic acid esters or mixed solvents thereof being preferred and methanol or ethanol being most preferred.

Examples of the reduction catalyst used include Pd/C, palladium hydroxide, Raney nickel, platinum oxide and platinum black, with Pd/C or palladium hydroxide being preferred.

The reaction temperature varies depending on the starting material and solvent, but is usually 0° C. to 70° C., preferably 10° C. to 50° C.

The reaction time varies depending on the starting material, solvent and reaction temperature, but is usually 30 minutes to five days, preferably one or three days.

The hydrogen pressure during the reaction in the case of using the reduction catalyst is usually 0.5 to 10 atm, preferably 1 to 5 atm.

Typically, the compound obtained in this process can be used in the next process only by filtering off the catalyst.

(Process F)

Compound (1) can also be obtained by Process F.

Process F

[Chemical Formula 8]

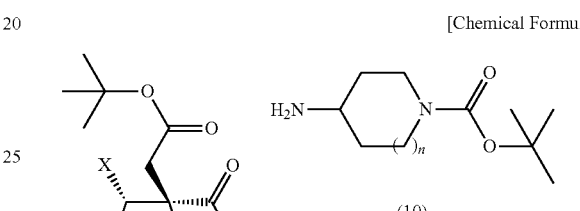

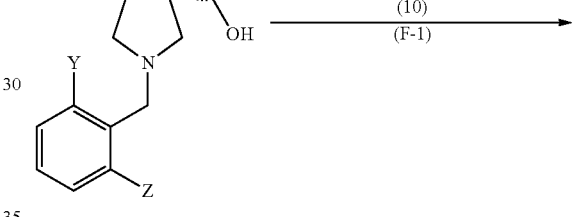

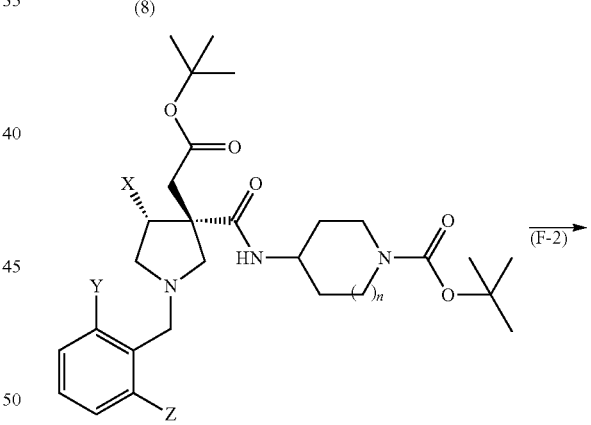

(11)

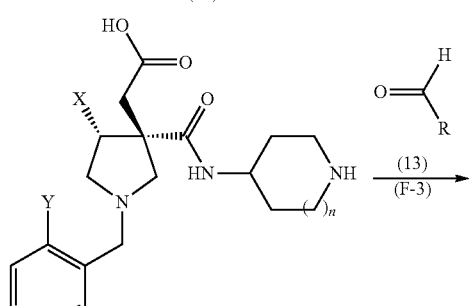

(12)

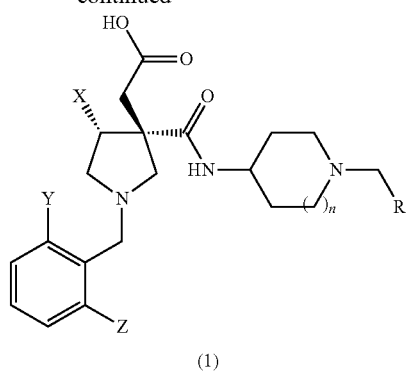

(1)

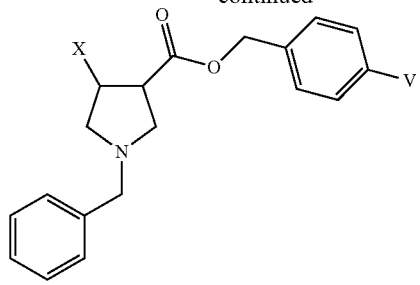

(17)

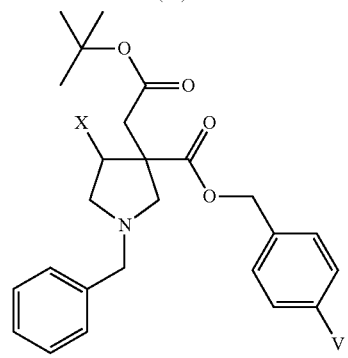

(18)

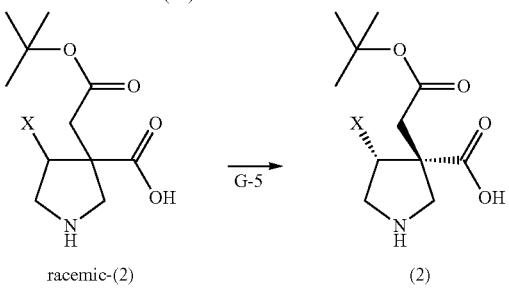

racemic-(2)  (2)

[wherein R, X, Y, Z and n are as defined above.]

(Process F-1) Amidation

This process is a process of producing Compound (11) by subjecting the carboxyl group of Compound (8) and the amino group of Compound (10) to dehydration condensation and can be performed by a method similar to that of Process A.

(Process F-2) Elimination of Tert-Butyl Group and Tert-Butyloxycarbonyl Group

This process is a process of producing Compound (12) by reacting Compound (11) with an acid and can be performed by a method similar to that of Process C.

(Process F-3) Reductive Amination

This process is a process of producing Compound (1) by reacting Compound (12) with aldehyde compound (13) in the presence of a reducing agent and can be performed by a method similar to that of Process D.

Compounds (10) and (13) can be available as commercially available compounds, or can be readily produced from commercially available compounds by methods usually performed by those skilled in the art.

(Process G)

Compound (2) can also be produced by Process G below.

Process G

[Chemical Formula 9]

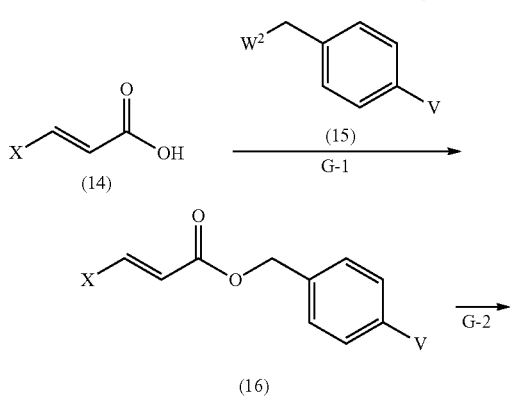

[wherein X is as defined above, V represents a hydrogen atom or a methoxy group, and $W^2$ represents a halogen atom.]

(Process G-1) Esterification

This process is a process of producing Compound (16) by reacting Compound (14) with Compound (15) in an inert solvent in the presence of a base. This process can be performed according to Process B.

(Process G-2) Cycloaddition

This process is a process of producing Compound (17) by reacting Compound (16) with N-(methoxymethyl)-N-(trimethylsilylmethyl)benzylamine in an inert solvent in the presence of an acid.

The solvent used is not particularly limited insofar as it dissolves the starting material to some degree and does not inhibit the reaction, and examples include ethers such as tetrahydrofuran, halogenated hydrocarbons such as dichloromethane and chloroform, and aromatic hydrocarbons such as benzene and toluene, with dichloromethane and toluene and a mixed solvent thereof being preferred.

The acid used may be any acid usually used by those skilled in the art and is preferably trifluoroacetic acid.

The reaction temperature varies depending on the starting material, solvent, reducing agent and acid, but is usually −20° C. to 60° C., preferably 10° C. to 40° C.

The reaction time varies depending on the starting material, solvent, reducing agent and acid, but is usually 30 minutes to five days, preferably 1 to 24 hours.

The reaction may be exothermic, it is preferable to add N-(methoxymethyl)-N-(trimethylsilylmethyl)benzylamine dropwise while being careful about heat generation, after Compound (16), solvent and acid are mixed.

(Process G-3) Alkylation

This process is a process of producing Compound (18) by causing a base to act on Compound (17) in an inert solvent and then reacting with tert-butyl bromoacetate.

The solvent used is not particularly limited insofar as it dissolves the starting material to some degree and does not inhibit the reaction, and examples include ethers such as tetrahydrofuran and diethyl ether, aliphatic hydrocarbons such as hexane, aromatic hydrocarbons such as toluene, and mixed solvents thereof, with tetrahydrofuran and a mixed solvent of tetrahydrofuran and hexane being preferred.

Preferred examples of the base used include lithium salts of organic amines such as lithium diisopropylamide and lithium bis(trimethylsilyl)amide, with lithium diisopropylamide and lithium bis(trimethylsilyl)amide being more preferred.

The reaction temperature varies depending on the starting material, solvent and base, but is usually −100° C. to 50° C., preferably −80° C. to −40° C., most preferably −80° C. to −70° C.

The reaction time varies depending on the starting material, solvent and base, but is usually 30 minutes to five days, preferably 1 to 24 hours, most preferably 2 to 5 hours.

(Process G-4) Hydrogenation Reaction

This process is a process of reacting Compound (18) with hydrogen in an inert solvent in the presence of a reduction catalyst to remove the benzyl group.

This process can be performed according to Process E above.

(Process G-5) Chiral Resolution

This process is a process of obtaining Compound (2) by subjecting a racemate of Compound (2) to chiral resolution.

The solvent used for the mobile phase or sample charge in the resolution is not particularly limited insofar as it dissolves the starting material to some degree and does not have adverse effects on columns or samples, and examples include water, aqueous saline solutions, alcohols such as methanol, ethanol and 2-propanol, hexane, acetonitrile, tetrahydrofuran, trifluoroacetic acid, diethylamine, or mixed solvents thereof, with acetonitrile, ethanol, or a mixed solvent of ethanol and hexane being preferred.

Examples of the column used for the resolution include various commercially available columns for optical resolution, with CHIRALPAK AD-H, CHIRALPAK IA and CHIRALCEL OZ-H manufactured by Daicel Chemical Industries, Ltd. being preferred.

The column temperature during the resolution is preferably 10° C. to 45° C.

(Process H)

Compound (3) used in Process A or the like can also be produced by Process H below.

Process H

[Chemical Formula 10]

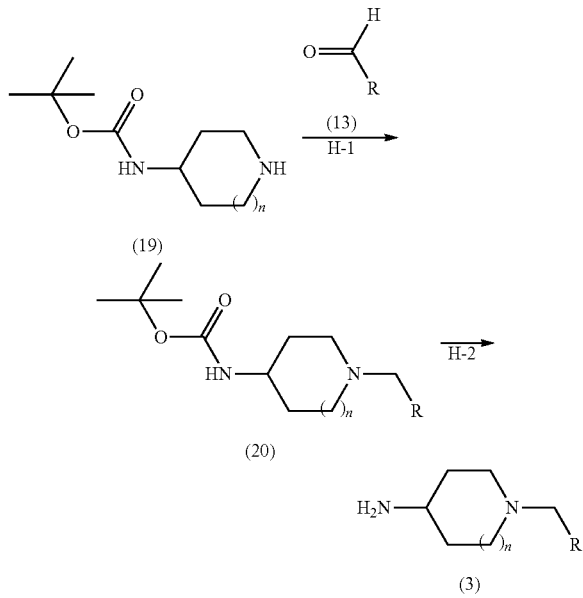

[wherein R and n are as defined above.]

(Process H-1) Reductive Amination

This process is a process of producing Compound (20) by reacting Compound (19) with Compound (13) in the presence of a reducing agent in an inert solvent in the presence or absence of an acid and can be performed according to Process D.

(Process H-2) Elimination of Tert-Butyloxycarbonyl Group

This process is a process of producing Compound (3) by reacting Compound (20) with an acid in the absence of a solvent or in an inert solvent to remove the tert-butyloxycarbonyl group and can be performed according to Process C.

(Process I)

Compound (2) can also be produced by Process I below using a racemate of Compound (2) as a starting material.

Process I

[Chemical Formula 11]

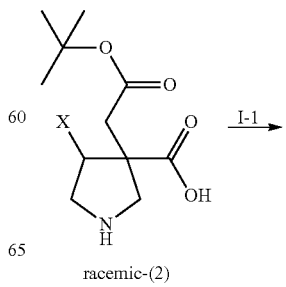

racemic-(2)

-continued

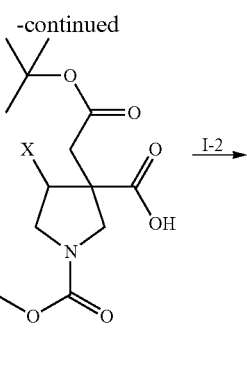

(21)

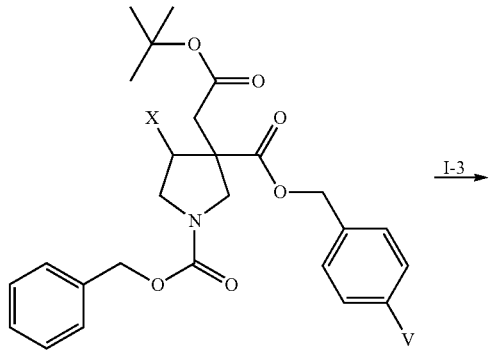

(22)

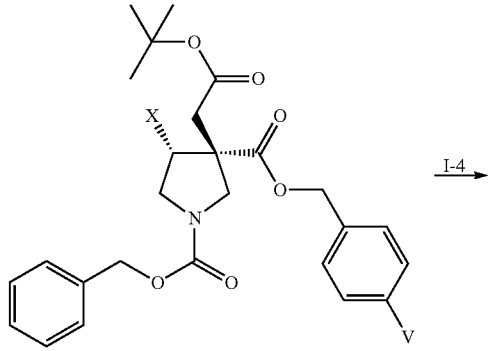

chiral-(22)

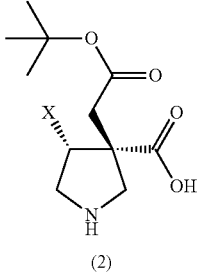

(2)

[wherein X and V are as defined above.]

(Process I-1) Introduction of Benzyloxycarbonyl Group

This process is a process of reacting a racemate of Compound (2) with benzyl chloroformate in an inert solvent in the presence of a base to introduce a benzyloxycarbonyl group.

The solvent used is not particularly limited insofar as it dissolves the starting material to some degree and does not inhibit the reaction, and examples include ethers such as tetrahydrofuran and 1,4-dioxane, water, N,N-dimethylformamide, dichloromethane, acetone and mixed solvents thereof, with a mixed solvent of water and acetone being preferred.

Examples of the base used include inorganic bases such as sodium hydroxide, potassium hydroxide, sodium bicarbonate, sodium carbonate and potassium carbonate, and organic amines such as triethylamine and diisopropylethylamine, with sodium hydroxide being preferred.

The reaction temperature varies depending on the starting material, solvent and base, but is usually −30° C. to 20° C., preferably −10° C. to 15° C.

The reaction time varies depending on the starting material, solvent and base, but is usually 30 minutes to five days, preferably 1 to 24 hours.

(Process I-2) Esterification Reaction

This process is a process of producing Compound (22) by reacting Compound (21) with benzyl halide in an inert solvent in the presence of a base. This process can be performed according to Process B.

(Process I-3) Chiral Resolution

This process is a process of obtaining a chiral form of Compound (22) by subjecting Compound (22) to chiral resolution. This process can be performed according to Process G-5.

(Process I-4) Hydrogenation Reaction

This process is a process of obtaining Compound (2) by reacting the chiral form of Compound (22) with hydrogen in an inert solvent in the presence of a reduction catalyst. This process can be performed according to Process E.

(Process J)

Compound (2) can also be produced by Process J below using Compound (18) as a starting material.

Process J

[Chemical Formula 12]

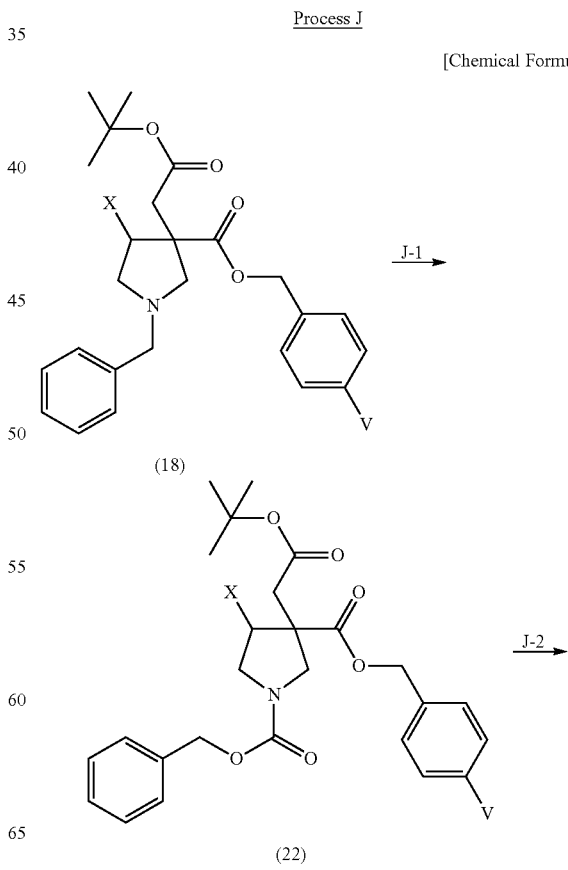

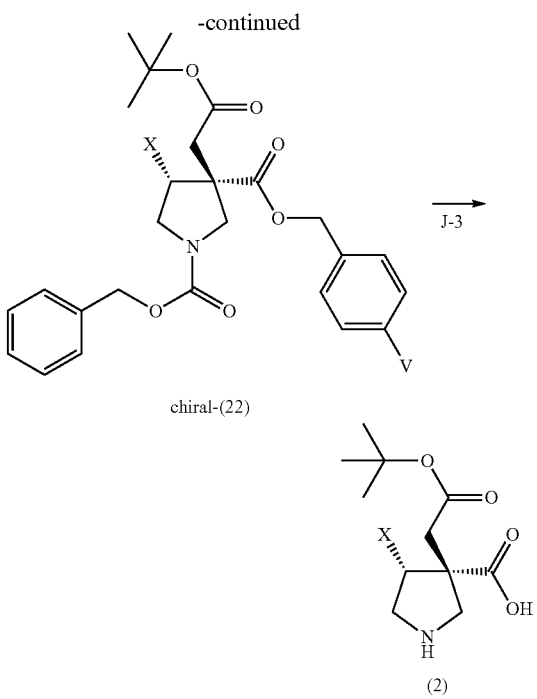

chiral-(22)

[wherein X and V have the same meaning as above.]

(Process J-1) Introduction of Benzyloxycarbonyl Group

This process is a process of obtaining Compound (22) by reacting Compound (18) with benzyl chloroformate in an inert solvent to replace the benzyl group with a benzyloxycarbonyl group.

The solvent used is not particularly limited insofar as it dissolves the starting material to some degree and does not inhibit the reaction, and examples include tetrahydrofuran, toluene, dichloromethane, chloroform and mixed solvents thereof, with dichloromethane being preferred.

The reaction temperature varies depending on the starting material and solvent, but is usually −20° C. to 60° C., preferably 0° C. to 40° C.

The reaction time varies depending on the starting material and solvent, but is usually 30 minutes to five days, preferably 1 to 24 hours.

(Process J-2) Chiral Resolution

This process is a process of obtaining a chiral form of Compound (22) by subjecting Compound (22) to chiral resolution. This process can be performed according to Process G-5.

(Process J-3) Hydrogenation Reaction

This process is a process of obtaining Compound (2) by reacting the chiral form of Compound (22) with hydrogen in an inert solvent in the presence of a reduction catalyst. This process can be performed according to Process E.

After completion of the reaction in each process of each method described above, the target compound in each process can be collected from the reaction mixture according to a conventional method.

For example, when the whole reaction mixture is a liquid, the reaction mixture is cooled to room temperature or cooled with ice as desired, and neutralized with an acid, alkali, oxidizing agent or reducing agent as appropriate, an organic solvent immiscible with water and not reactive with the target compound such as ethyl acetate is added, and the layer containing the target compound is separated. Next, a solvent immiscible with the resulting layer and not reactive with the target compound is added, the layer containing the target compound is washed, and the layer is separated. Moreover, when the layer is an organic layer, the target compound can be collected by drying with a drying agent such as anhydrous magnesium sulfate or anhydrous sodium sulfate and distilling off the solvent. When the layer is an aqueous layer, the target compound can be collected by electrically demineralizing and then lyophilizing the layer.

In addition, when the whole reaction mixture is a liquid and if possible, the target compound can be collected only by distilling off substances other than the target compound (such as a solvent or a reagent) under normal pressure or reduced pressure.

Further, when only the target compound is precipitated as a solid, or when the whole reaction mixture described above is a liquid and only the target compound is precipitated in the course of collection, the target compound can be further collected by collecting the target compound by filtration first, washing the target compound collected by filtration with an appropriate organic or inorganic solvent and drying, such that the mother liquor is treated in a manner similar to the case where the whole reaction mixture described above is a liquid.

Still further, when only the reagent or catalyst is present as a solid, or the whole reaction mixture described above is a liquid and only the reagent or catalyst is precipitated as a solid in the course of collection, and the target compound is dissolved in the solution, the target compound can be collected by filtering off the reagent or catalyst first, washing the reagent or catalyst filtered off with an appropriate organic or inorganic solvent, combining the resulting washings with the mother liquor, and treating the resulting mixture in a manner similar to the case where the whole reaction mixture described above is a liquid.

In particular, when substances other than the target compound which are contained in the reaction mixture do not inhibit the reaction in the next step, the reaction mixture may also be used in the next step as is without particularly isolating the target compound.

Recrystallization, various chromatography methods and distillation may be carried out as appropriate in order to improve the purity of the target compound collected by the above method.

Typically, when the collected target compound is a solid, the purity of the target compound can be improved by recrystallization. In recrystallization, a single solvent or a mixture of a plurality of solvents not reactive with the target compound may be used. Specifically, the target compound is first dissolved in one or more solvents not reactive with the target compound at room temperature or under heating. The resulting mixture is cooled with ice water or the like or is stirred or left to stand at mom temperature, such that the target compound can be crystallized from the mixture.

The purity of the collected target compound can be improved by various chromatography methods. Generally, it is possible to use weak acidic silica gels such as Silica gel 60 manufactured by Merck KGaA (70-230 mesh or 340-400 mesh) and BW-300 manufactured by Fuji Silysia Chemical Ltd. (300 mesh). When the target compound is basic and is adsorbed onto the above silica gels too strongly, it is also possible to use NH silica gels such as propylamine coated silica gel manufactured by Fuji Silysia Chemical Ltd. (200-350 mesh) and disposable medium pressure preparative packed column manufactured by Yamazen Corporation (Hi-Flash Amino). When the target compound is dipolar or must be eluted with a more polar solvent such as methanol, for example, it is also possible to use NAM-200H or NAM-300H manufactured by NAM Laboratory or YMC GEL ODS-A manufactured by YMC Co. Ltd. It is also possible to use disposable medium pressure preparative packed columns as described above that are previously packed with fillers and manufactured by Yamazen Corporation, Wako Pure Chemical Industries, Ltd., Biotage AB or W.R. Grace & Co. (Hi-Flash Amino). The target compound whose purity is improved can be obtained by eluting the target compound with one or more solvents not reactive with the target compound using these silica gels, and distilling off the solvent(s).

When the collected target compound is a liquid, the purity of the target compound can also be improved by distillation. In distillation, the target compound can be distilled out by subjecting the target compound to reduced pressure at room temperature or under heating.

Representative examples of the method for producing Compound (1) have been described above. Raw material compounds and various reagents in the production of Compound (1) may form salts or solvates such as hydrates, all vary depending on the starting material, the solvent used or the like, and are not particularly limited insofar as they do not inhibit the reaction. Also, the solvent used varies depending on the starting material, the reagent or the like, and is not particularly limited insofar as it does not inhibit the reaction and dissolves the starting material to some degree, obviously. When Compounds (1) are obtained as free forms, they can be converted to salts that may be formed by Compounds (1) or solvates of the compounds or salts by conventional methods.

When Compounds (1) are obtained as salts or solvates, they can be converted to free forms of Compounds (1) by conventional methods.

Various isomers obtained for Compounds (1) (such as geometric isomers, optical isomers, rotamers, stereoisomers and tautomers) can be purified and isolated using common separation means, for example, recrystallization, diastereomeric salt formation, enzymatic resolution and various chromatography methods (such as thin layer chromatography, column chromatography and gas chromatography).

Compounds (1) or pharmaceutically acceptable salts thereof can be formulated by conventional methods, and examples of dosage forms include oral formulations (such as tablets, granules, powders, capsules and syrups), injections (for intravenous administration, intramuscular administration, subcutaneous administration and intraperitoneal administration) and external formulations (such as transdermal absorption formulations (such as ointments and patches), ophthalmic preparations, nasal preparations and suppositories).

These solid formulations such as tablets, capsules, granules and powders may contain usually 0.001 to 99.5 wt %, preferably 0.01 to 90 wt % or the like, of Compounds (1) or pharmaceutically acceptable salts thereof.

When oral solid formulations are manufactured, tablets, granules, powders and capsules can be prepared by adding diluents, binders, disintegrants, lubricants, colorants or the like to compounds (1) or pharmaceutically acceptable salts thereof as necessary and treating by conventional methods. Tablets, granules, powders, capsules and the like may also be film coated as necessary Examples of diluents include lactose, corn starch and microcrystalline cellulose, examples of binders include hydroxypropylcellulose and hydroxypropylmethylcellulose, and examples of disintegrants include carboxymethylcellulose calcium and croscarmellose sodium.

Examples of lubricants include magnesium stearate and calcium stearate, and examples of colorants include titanium oxide.

Examples of film coating agents include hydroxypropylcellulose, hydroxypropylmethylcellulose and methylcellulose.

Any excipients described above are not limited to these examples, obviously.

When injections (for intravenous administration, intramuscular administration, subcutaneous administration and intraperitoneal administration) are manufactured, they can be manufactured by adding pH adjusters, buffers, suspending agents, solubilizing agents, antioxidants, preservatives (antiseptics), tonicity adjusting agents or the like to Compounds (1) or pharmaceutically acceptable salts thereof as necessary and treating by conventional methods. Lyophilized formulations to be dissolved before use may also be prepared by lyophilization. These injections can be administered intravenously, subcutaneously and intramuscularly, for example.

Examples of pH adjusters and buffers include organic acids or inorganic acids and/or salts thereof, examples of suspending agents include methylcellulose, polysorbate 80 and carboxymethylcellulose sodium, examples of solubilizing agents include polysorbate 80 and polyoxyethylene sorbitan monolaurate, examples of antioxidants include α-tocopherol, examples of preservatives include methyl parahydroxybenzoate and ethyl parahydroxybenzoate, and examples of tonicity adjusting agents include glucose, sodium chloride and mannitol; however, the excipients are not limited to these examples, obviously.

These injections may contain usually 0.000001 to 99.5 wt %, preferably 0.00001 to 90 wt % or the like, of Compounds (1) or pharmaceutically acceptable salts thereof.

When external formulations are manufactured, transdermal absorption formulations (such as ointments and patches), eye drops, nasal drops, suppositories and the like can be manufactured by adding base materials and, as necessary, the emulsifiers, preservatives, pH adjusters, colorants and the like described above to Compounds (1) or pharmaceutically acceptable salts thereof, and treating by conventional methods.

Various raw materials conventionally used for pharmaceuticals, quasi drugs, cosmetics and the like can be used as base materials, and examples include raw materials such as animal and vegetable oils, mineral oils, ester oils, waxes, higher alcohols and purified water.

These external formulations may contain usually 0.000001 to 99.5 wt %, preferably 0.00001 to 90 wt % or the like, of Compounds (1) or pharmaceutically acceptable salts thereof.

The dosage of the medicine according to the present invention typically varies depending on the symptom, age, sex, weight or the like, but is acceptable if it is a dosage sufficient to produce a desired effect. For example, for an adult, a dosage of about 0.1 to 5000 mg (preferably 0.5 to 1000 mg, more preferably 1 to 600 mg) per day is used in one dose during one or more days or in 2 to 6 divided doses for one day.

The present invention also include isotopically labeled Compounds (1), and such compounds are the same as Compounds (1), except that one or more atoms are replaced with an atom(s) having an atomic mass or mass number different from an atomic mass or mass number commonly found in nature. Isotopes that can be incorporated into Compounds (1) are isotopes of hydrogen, carbon, nitrogen, oxygen, phosphorus, fluoride, iodine and chlorine, for example, and include $^{2}H$, $^{3}H$, $^{11}C$, $^{14}C$, $^{13}N$, $^{15}O$, $^{18}F$, $^{32}P$, $^{35}S$, $^{123}I$ and $^{125}I$.

Compounds (1) containing the above-described isotopes and/or other isotopes or pharmaceutically acceptable derivatives thereof (such as salts) fall within the claims of the present specification. The isotopically labeled compounds of the present invention, for example, compounds into which radioisotopes such as $^3H$ and/or $^{14}C$ are incorporated, are useful for tissue distribution assays for medicines and/or substrates. $^3H$ and $^{14}C$ are considered to be useful because of their ease in preparation and detection. Isotopes $^{11}C$ and $^{18}F$ are considered to be useful for PET (positron emission tomography), an isotope $^{125}I$ is considered to be useful for SPECT (single photon emission computed tomography), and all these isotopes are useful for brain imaging. Replacement with heavier isotopes such as $^2H$ produces certain therapeutic advantages such as an increase in the in vivo half-life due to higher metabolic stability, or a reduction in the required dose, and is therefore considered to be useful under certain circumstances. Isotopically labeled Compounds (1) can be uniformly prepared by performing the procedures disclosed in the following schemes and/or examples using readily available isotopically labeled reagents in place of non-isotopically labeled reagents.

Compounds (1) can be used as chemical probes to trap target proteins in bioactive low molecular weight compounds. Specifically, Compound (1) can be converted to an affinity chromatography probe, a photoaffinity probe or the like by introducing a labeling group, a linker or the like into a moiety differing from a structural moiety essential for expression of activity of the compound by a technique described in J. Mass Spectrum. Soc. Jpn., Vol. 51, No. 5, 2003, pp. 492-498 or WO 2007/139149 or the like.

Examples of labeling groups, linkers or the like used for chemical probes include groups shown in the group consisting of (1) to (5) below:
(1) protein labeling groups such as photoaffinity labeling groups (such as a benzoyl group, a benzophenone group, an azido group, a carbonylazido group, a diaziridine group, an enone group, a diazo group and a nitro group) and chemical affinity groups (such as a ketone group in which an α-carbon atom is replaced with a halogen atom, a carbamoyl group, an ester group, an alkylthio group, Michael receptors such as α,β-unsaturated ketones and esters, and an oxirane group),
(2) cleavable linkers such as —S—S—, —O—Si—O—, monosaccharides (such as a glucose group and a galactose group) or disaccharides (such as lactose), and oligopeptide linkers cleavable by enzymatic reaction,
(3) fishing tag groups such as biotin and a 3-(4,4-difluoro-5,7-dimethyl-4H-3a,4a-diaza-4-bora-s-indacen-3-yl)propionyl group,
(4) detectable markers such as radiolabeling groups such as $^{125}I$, $^{32}P$, $^3H$ and $^{14}C$; fluorescence labeling groups such as fluorescein, rhodamine, dansyl, umbelliferone, 7-nitrofurazanyl and a 3-(4,4-difluoro-5,7-dimethyl-4H-3a,4a-diaza-4-bora-s-indacen-3-yl)propionyl group; chemiluminescent groups such as luciferin and luminol; and heavy metal ions such as lanthanoid metal ions and radium ions; or
(5) groups bound to solid phase carriers such as glass beads, glass beds, microtiter plates, agarose beads, agarose beds, polystyrene beads, polystyrene beds, nylon beads and nylon beds.

Probes prepared by introducing labeling groups or the like selected from the group consisting of (1) to (5) above into Compounds (1) according to the method described in the above documents or the like can be used as chemical probes for identification of labeled proteins useful for searching for novel drug targets, for example.

EXAMPLES

Compounds (1) can be produced by the methods described in examples below, for example, and the effects of Compounds (1) can be confirmed by the methods described in test examples below. However, these methods are illustrative and the present invention is not limited to the following specific examples in any case.

When deuterium oxide is used as a measurement solvent in $^1H$-NMR for confirmation of the structures of compounds, the chemical shift of the spectrum of each compound is shown as a value corrected with the chemical shift of the solvent residual peak in deuterium oxide as 4.79.

Example 1

Chiral form of 2-[(3R*,4S*)-1-{[2-chloro-6-(trifluoromethyl)phenyl]methyl}-3-{[1-(2-fluoropentyl)piperidin-4-yl]carbamoyl}-4-methylpyrrolidin-3-yl] acetic acid Example 1a tert-Butyl 4-{[(benzyloxy)carbonyl]amino}piperidine-1-carboxylate tert-Butyl 4-aminopiperidine-1-carboxylate (10 g, 49.9 mmol), N,N-diisopropylethylamine (26 ml, 149 mmol), benzyl chloroformate (8.5 ml, 59.5 mmol) and dichloromethane (dehydrated) (300 ml) were mixed under ice-cooling. The resulting mixture was stirred at room temperature for one hour. An aqueous saturated sodium bicarbonate solution was added to the reaction mixture, which was extracted with dichloromethane three times. The organic layer was washed with brine and dried over anhydrous sodium sulfate, and the solvent was distilled off. The residue was purified by silica gel column chromatography (silica gel, elution solvent: ethyl acetate/heptane) to give the title compound (13.1 g, yield 78.5%).

$^1H$-NMR (400 MHz, CDCl$_3$) δ ppm; 1.24-1.38 (2H, m), 1.45 (9H, s), 1.88-2.00 (2H, br), 2.80-2.94 (2H, br), 3.60-3.72 (1H, br), 3.92-4.10 (2H, br), 4.63-4.75 (1H, m), 5.09 (2H, s), 7.26-7.40 (5H, m).

Example 1b

Benzyl N-(piperidin-4-yl)carbamate

A mixture of tert-butyl 4-{[(benzyloxy)carbonyl]amino}piperidine-1-carboxylate obtained in Example 1a (13.1 g, 39.2 mmol), a 5 N aqueous hydrochloric acid solution (40 ml, 200 mmol) and methanol (40 ml) was stirred at mom temperature for 23 hours. A 5 N aqueous sodium hydroxide solution (40 ml) was added to the reaction mixture under ice-cooling. Water and the solvent were distilled off from the reaction mixture while the mixture was azeotropically distilled with ethanol. Ethanol was added to the residue, the insoluble matter was removed by filtration, and the filtrate was concentrated to give the title compound (9.10 g, yield 99.1%).

$^1H$-NMR (400 MHz, CDCl$_3$) δ ppm; 1.31-1.42 (2H, m), 1.92-2.04 (2H, br), 2.70 (2H, d, J=12 Hz), 3.10 (2H, d, J=12 Hz), 3.56-3.68 (1H, br), 4.72-4.81 (1H, br), 5.09 (2H, s), 7.26-7.40 (5H, m).

Example 1c

Chiral form of benzyl N-[1-(2-fluoropentyl)piperidin-4-yl]carbamate (5S)-(−)-2,2,3-Trimethyl-5-benzyl-4-imidazolidinone dichloroacetic acid (90 mg, 0.259 mmol), N-fluorobenzenesulfonimide (484 mg, 1.53 mmol), 2-propanol (0.4 ml) and tetrahydrofuran (dehydrated) (3.6 ml) were mixed at room temperature. The reaction mixture was cooled to −10° C., and pentanal (0.175 ml, 1.67 mmol) was then added, followed by stirring for three hours and 20 minutes while naturally warming from −10° C. to room temperature. Benzyl N-(piperidin-4-yl)carbamate obtained in Example 1b (304 mg, 1.3 mmol) and sodium triacetoxyborohydride (600 mg, 2.83 mmol) were added to the reaction mixture, which was stirred at room temperature for 15 hours and 40 minutes. Water and an aqueous sodium bicarbonate solution were added to the reaction mixture, the insoluble matter was removed by filtration, and the resulting filtrate was extracted with ethyl acetate twice. The organic layer was washed with brine and dried over anhydrous sodium sulfate, and the solvent was distilled off. The residue was purified by silica gel column chromatography (silica gel, elution solvent: ethyl acetate/heptane) to give a chiral form mixture of the title compound (44 mg, yield 10.5%).

$^1$H-NMR (400 MHz, CDCl$_3$) δ ppm; 0.94 (3H, t, J=7 Hz), 1.38-1.70 (6H, m), 1.85-2.00 (2H, br), 2.14-2.24 (2H, m), 2.35-2.48 (1H, m), 2.55-2.64 (1H, m), 2.80-3.00 (2H, m), 3.48-3.60 (1H, m), 4.59-4.72 (2H, m), 5.09 (2H, s), 7.26-7.37 (5H, m).

Optical resolution by HPLC (Analysis conditions) Column: CHIRALPAK AD-H (manufactured by Daicel Chemical Industries, Ltd.) (0.46 cm diameter×15 cm), eluent: hexane/ethanol=9/1 (v/v), flow rate: 1 ml/min., detection: UV (210 nm)

(Analysis result) The resulting chiral form mixture was analyzed under the above analysis conditions, and a peak with a retention time of 7.30 minutes (enantiomeric excess: 80% ee) and a peak with a retention time of 8.28 minutes were observed.

Further two lots of the chiral form mixture were obtained by a method similar to the above method. Three lots in total of the chiral form mixture (451 mg, 1.4 mmol) were dissolved in ethanol (18 ml) and optically resolved repeatedly under the following fractionation conditions, and the peak with a shorter retention time was fractionated to give the title compound (318 mg).

(Fractionation conditions) Column: CHIRALPAK AD-H (manufactured by Daicel Chemical Industries, Ltd.) (2 cm diameter×25 cm), eluent: hexane/ethanol=9/1 (v/v), flow rate: 10 ml/min., detection: UV (220 nm)

$^1$H-NMR (400 MHz, CDCl$_3$) δ ppm; 0.94 (3H, t, J=7 Hz), 1.38-1.70 (6H, m), 1.85-2.00 (2H, br), 2.14-2.24 (2H, m), 2.35-2.48 (1H, m), 2.55-2.64 (1H, m), 2.80-3.00 (2H, m), 3.48-3.60 (1H, m), 4.59-4.72 (2H, m), 5.09 (2H, s), 7.26-7.37 (5H, m).

The resulting title compound was analyzed under the above analysis conditions to find that the retention time was 7.41 minutes and the enantiomeric excess was >99% ee.

Example 1d

Chiral form of 1-(2-fluoropentyl)piperidin-4-amine

A mixture of the chiral form (with a shorter retention time) of benzyl N-[1-(2-fluoropentyl)piperidin-4-yl]carbamate obtained in Example 1c (318 mg, 0.986 mmol), 10% Pd/C (100 mg) and methanol (7 ml) was stirred at room temperature for two hours under a hydrogen atmosphere. The atmosphere in the reaction vessel was replaced with nitrogen, 10% Pd/C was filtered off, and the solvent was distilled off to give the title compound (249 mg).

$^1$H-NMR (400 MHz, CDCl$_3$) δ ppm; 0.95 (3H, t, J=7 Hz), 1.35-1.70 (4H, m), 1.92-2.10 (2H, br), 2.20-2.32 (2H, br), 2.48-2.62 (2H, br), 2.65-2.91 (2H, m), 3.18-3.30 (2H, br), 3.31-3.42 (1H, br), 4.72-4.93 (1H, m).

Example 1e

Benzyl (2E)-but-2-enoate

Crotonic acid (70 g, 812 mmol) was dissolved in N,N-dimethylformamide (467 ml), which was cooled in an ice bath under nitrogen, and potassium carbonate (61.6 g, 447 mmol) was added. Benzyl bromide (91.7 ml, 772 mmol) was added dropwise to the reaction mixture over 20 minutes. The reaction mixture was stirred at mom temperature for 18 hours. Ethyl acetate was added to the reaction mixture, which was filtered through Celite. The filtered ethyl acetate solution was washed with water, a saturated aqueous sodium bicarbonate solution and a saturated aqueous sodium chloride solution. The organic layer was dried over magnesium sulfate, filtered and concentrated under reduced pressure to give the title compound (142 g, yield: 99.4%).

$^1$H-NMR (400 MHz, CDCl$_3$) δ ppm; 1.87-1.90 (3H, m), 5.17 (2H, s), 5.87-5.92 (1H, m), 6.98-7.07 (1H, m), 7.26-7.39 (5H, m).

Example 1f

Benzyl (3RS,4SR)-1-benzyl-4-methylpyrrolidine-3-carboxylate

Benzyl (2E)-but-2-enoate obtained in Example 1e (20.5 g, 116 mmol) was dissolved in dichloromethane (5 ml), and the mixture was cooled in an ice bath with stirring. Trifluoroacetic acid (257 μl, 3.47 mmol) was added, and N-(methoxymethyl)-N-(trimethylsilylmethyl)benzylamine (33.1 g, 139 mmol) was added dropwise to the reaction liquid over 15 minutes so that the internal temperature did not exceed 62° C., while washing with dichloromethane (25 ml). The reaction liquid was left to stand until it reached mom temperature and was stirred for 15 hours. The reaction liquid was concentrated and purified by silica gel column chromatography (elution solvent: ethyl acetate/heptane) to give the title compound (38 g).

$^1$H-NMR (400 MHz, CDCl$_3$) δ ppm; 1.14 (3H, d, J=6 Hz), 2.18-2.22 (1H, m), 2.48-2.65 (2H, m), 2.75-2.85 (2H, m), 2.90-2.94 (1H, m), 3.54-3.66 (2H, m), 5.13 (2H, s), 7.20-7.40 (10H, m).

Example 1g

Benzyl (3RS,4SR)-1-benzyl-3-[2-(tert-butoxy)-2-oxoethyl]-4-methylpyrrolidine-3-carboxylate Benzyl (3RS,4SR)-1-benzyl-4-methylpyrrolidine-3-carboxylate obtained in Example 1f (30 g, 97.4 mmol) was dissolved in tetrahydrofuran (300 ml), which was cooled to −70° C. with stirring under nitrogen. A 1.11M lithium diisopropylamide/n-hexane-tetrahydrofuran solution (105 ml, 116 mmol) was added dropwise over 20 minutes so that the internal temperature did not exceed −64.3° C. The mixture was stirred at −70° C. for 1 hour, and tetrahydrofuran (30 ml) and tert-butyl bromoacetate (26.6 g, 136 mmol) were then added dropwise over 10 minutes so that the internal temperature did not exceed −60° C. The reaction mixture was stirred at −70° C. for further one hour, and a saturated aqueous ammonium chloride solution was then added to the reaction mixture.

Immediately thereafter, the reaction mixture was diluted with water and ethyl acetate was added. The organic layer was washed with brine and a 5 N aqueous hydrochloric acid solution, and then dried over magnesium sulfate, filtered and concentrated. The residue was purified by silica gel column chromatography (elution solvent: ethyl acetate/heptane). The residue was further purified by NH silica gel column chromatography (elution solvent: heptane/ethyl acetate=98/2) to give the title compound (6 g, yield: 14.5%).

$^1$H-NMR (400 MHz, CDCl$_3$) δ ppm; 0.86 (3H, d, J=6 Hz), 1.34 (9H, s), 2.05-2.15 (2H, m), 2.53 (1H, d, J=17 Hz), 2.91-3.00 (3H, m), 3.28 (1H, d, J=10 Hz), 3.59-3.72 (2H, m), 5.08-5.16 (2H, m), 7.19-7.39 (10H, m).

By a similar method, 18.1 g of the title compound was obtained.

Example 1h 1,3-Dibenzyl (3RS,4SR)-3-[2-(tert-butoxy)-2-oxoethyl]-4-methylpyrrolidine-1,3-dicarboxylate Benzyl (3RS,4SR)-1-benzyl-3-[2-(tert-butoxy)-2-oxoethyl]-4-methylpyrrolidine-3-carboxylate obtained in a manner similar to that in Example 1g (11.7 g, 27.6 mmol) was dissolved in dichloromethane (117 ml), and benzyl chloroformate (23.7 ml, 166 mmol) was added dropwise to the reaction liquid over 20 minutes so that the internal temperature did not exceed 22° C. The mixture was stirred at room temperature for 12 hours, and then solvent was distilled off. The residue was purified by NH silica gel column chromatography (elution solvent: ethyl acetate/heptane) to give the title compound (9.1 g, yield: 70.5%).

$^1$H-NMR (400 MHz, CDCl$_3$) δ ppm; 0.84-0.90 (3H, m), 1.32-1.46 (9H, m), 2.09-2.16 (1H, m), 2.21-2.27 (1H, m), 3.04-3.14 (2H, m), 3.33-3.38 (1H, m), 3.60-3.68 (1H, m), 4.32 (1H, t, J=12 Hz), 5.07-5.20 (4H, m), 7.26-7.36 (10H, m).
Analysis by HPLC;
(Analysis conditions 1) Column: CHIRALPAK AD-H (manufactured by Daicel Chemical Industries, Ltd.) (0.46 cm diameter×15 cm), eluent: hexane/ethanol=95/5 (v/v), flow rate: 1 ml/min., detection: UV (210 nm)
(Analysis result) The resulting title compound was analyzed under the above analysis conditions 1, and a peak with a retention time of 8.56 minutes and a peak with a retention time of 10.85 minutes were observed.

The title compound separately obtained was analyzed in a chiral column different from the above column.
(Analysis conditions 2) Column: CHIRALPAK IA (manufactured by Daicel Chemical Industries, Ltd.) (0.46 cm diameter×15 cm), eluent: hexane/ethanol=95/5 (v/v), flow rate: 1 ml/min., detection: UV (210 nm)
(Analysis result) The resulting title compound was analyzed under the above analysis conditions 2, and a peak with a retention time of 6.78 minutes and a peak with a retention time of 8.20 minutes were observed.

Example 1i (3R*,4S*)-3-[2-(tert-Butoxy)-2-oxoethyl]-4-methylpyrrolidine-3-carboxylic acid 1,3-Dibenzyl (3RS,4SR)-3-[2-(tert-butoxy)-2-oxoethyl]-4-methylpyrrolidine-1,3-dicarboxylate obtained in Example 1h (9.1 g) was optically resolved repeatedly under the following two types of conditions A or B.

Optical resolution by HPLC;
(Fractionation conditions A) Column: CHIRALPAK AD-H (manufactured by Daicel Chemical Industries, Ltd.) (2 cm diameter×25 cm), eluent: hexane/ethanol=85/15 (v/v), flow rate: 8-10 ml/min.
(Fractionation conditions B) Column: CHIRALPAK IA (manufactured by Daicel Chemical Industries, Ltd.) (3 cm diameter×25 cm), eluent: hexane/ethanol=95/5 (v/v), flow rate: 22 ml/min.

The peak with a shorter retention time was fractionated, and the resulting three lots were then analyzed under the following analysis conditions.
Analysis by HPLC;
(Analysis conditions) Column: CHIRALPAK AD-H (manufactured by Daicel Chemical Industries, Ltd.) (0.46 cm diameter×15 cm), eluent: hexane/ethanol=95/5 (v/v), flow rate: 1 ml/min., detection: UV (210 nm)
(Analysis result) The retention time was 9.0 minutes to 9.3 minutes, and the enantiomeric excess was >99% ee for all lots.

The three lots were combined, the resulting chiral form (4.04 g) was dissolved in methanol (121 ml), 10% Pd/C (0.77 g) was added, and the atmosphere was replaced with hydrogen gas. The mixture was stirred at room temperature for 13 hours and then stirred with addition of warm water (30 to 40° C., 122 ml), and the precipitated solid was dissolved. After Pd/C was filtered off, the solvent was concentrated and dried to give the title compound (2.1 g).

$^1$H-NMR (400 MHz, D$_2$O) δ ppm; 0.97 (3H, d, J=7 Hz), 1.42 (9H, s), 2.15-2.22 (1H, m), 2.30 (1H, d, J=17 Hz), 2.93 (1H, d, J=17 Hz), 3.04 (1H, t, J=12 Hz), 3.18 (1H, d, J=12 Hz), 3.49 (1H, dd, J=8, 12 Hz), 4.03 (1H, d, J=12 Hz).

Example 1j (3R*,4S*)-1-Benzyl-3-[2-(tert-butoxy)-2-oxoethyl]-4-methylpyrrolidine-3-carboxylic acid A mixture of (3R*,4S*)-3-[2-(tert-butoxy)-2-oxoethyl]-4-methylpyrrolidine-3-carboxylic acid obtained in Example 1i (1.8 g, 7.4 mmol), benzaldehyde (1.51 ml, 14.8 mmol), acetic acid (0.635 ml, 11.1 mmol), sodium triacetoxyborohydride (3.14 g, 14.8 mmol) and methanol (35 ml) was heated at 40° C. for 38 hours and 30 minutes. The reaction mixture was concentrated, and the resulting residue was purified by silica gel column chromatography (ODS silica gel, elution solvent: water/methanol) to give the title compound as Lot A (584 mg) and Lot B (708 mg).

$^1$H-NMR (400 MHz, CDCl$_3$) of Lot A δ ppm; 1.02 (3H, d, J=7 Hz), 1.38 (9H, s), 2.14 (1H, d, J=17 Hz), 2.15-2.28 (1H, br), 2.97 (1H, d, J=17 Hz), 3.10-3.42 (3H, m), 4.00-4.10 (1H, m), 4.30-4.40 (1H, br), 4.46 (1H, d, J=12 Hz), 7.45-7.53 (5H, m).

$^1$H-NMR of Lot B: identical to NMR of Lot A.

Example 1k

Chiral form of tert-butyl 2-[(3R*,4S*)-1-benzyl-3-{[1-(2-fluoropentyl)piperidin-4-yl]carbamoyl}-4-methylpyrrolidin-3-yl]acetate A mixture of (3R*,4S*)-1-benzyl-3-[2-(tert-butoxy)-2-oxoethyl]-4-methylpyrrolidine-3-carboxylic acid obtained in Example 1j (300 mg, 0.9 mmol), the chiral form of 1-(2-fluoropentyl)piperidin-4-amine obtained in Example 1d (182 mg, 0.967 mmol), triethylamine (0.376 ml, 2.7 mmol), PyBOP (656 mg, 1.26 mmol) and N,N-dimethylformamide (4.5 ml) was stirred at room temperature for 61 hours and 30 minutes. Triethylamine (0.207 ml, 1.49 mmol) and PyBOP (360 mg, 0.69 mmol) were further added, followed by stirring for four hours and 30 minutes. Water was added to the reaction mixture, which was extracted with ethyl acetate twice. The organic layer was washed with a saturated aqueous ammonium chloride solution and dried over anhydrous magnesium sulfate, and the solvent was distilled off. The residue was purified by silica gel column chromatography (NH silica gel, elution solvent: ethyl acetate/heptane) to give the title compound (161 mg, yield 35.5%).

$^1$H-NMR (400 MHz, CDCl$_3$) δ ppm; 0.92 (3H, d, J=7 Hz), 0.96 (3H, t, J=7 Hz), 1.40 (9H, s), 1.40-1.60 (6H, m), 1.82-2.09 (4H, m), 2.16-2.28 (2H, m), 2.36 (1H, d, J=10 Hz), 2.35-2.50 (1H, m), 2.56-2.67 (3H, m), 2.80-2.90 (2H, br), 3.09 (1H, d, J=16 Hz), 3.58-3.79 (4H, m), 4.59-4.80 (1H, m), 7.25-7.40 (5H, m), 8.58 (1H, d, J=8 Hz).

Example 11

Chiral form of tert-butyl 2-[(3R*,4S*)-1-{[2-chloro-6-(trifluoromethyl)phenyl]methyl}-3-{[1-(2-fluoropentyl)piperidin-4-yl]carbamoyl}-4-methylpyrrolidin-3-yl]acetate A mixture of the chiral form of tert-butyl 2-[(3R*,4S*)-1-benzyl-3-{[1-(2-fluoropentyl)piperidin-4-yl]carbamoyl}-4-methylpyrrolidin-3-yl]acetate obtained in Example 1k (161 mg, 0.32 mmol), 20% palladium hydroxide (135 mg) and methanol (5 ml) was stirred at mom temperature for 15 hours under a hydrogen atmosphere. The atmosphere in the reaction vessel was replaced with nitrogen, 20% palladium hydroxide was filtered off, and the solvent was distilled off. 2-(Bromomethyl)-1-chloro-3-(trifluoromethyl)benzene (159 mg, 0.581 mmol), potassium carbonate (97 mg, 0.702 mmol) and N,N-dimethylformamide (2 ml) were added to the resulting residue, which was heated at 45° C. for three hours and 15 minutes. Water was added to the reaction mixture, which was extracted with ethyl acetate twice. The organic layer was washed with a saturated aqueous ammonium chloride solution and dried over anhydrous magnesium sulfate, and the solvent was distilled off. The residue was purified by silica gel column chromatography (NH silica gel, elution solvent: ethyl acetate/heptane) to give the title compound (153 mg, yield 78.9%).

$^1$H-NMR (400 MHz, CDCl$_3$) δ ppm; 0.91 (3H, d, J=7 Hz), 0.95 (3H, t, J=7 Hz), 1.38-1.70 (7H, m), 1.39 (9H, s), 1.82-1.90 (1H, br), 1.97 (1H, d, J=16 Hz), 2.00-2.20 (3H, m), 2.31-2.45 (1H, m), 2.50-2.68 (3H, m), 2.80-2.92 (3H, m), 3.12 (1H, d, J=16 Hz), 3.57 (1H, d, J=10 Hz), 3.60-3.72 (1H, m), 3.92 (1H, d, J=13 Hz), 3.98 (1H, d, J=13 Hz), 4.56-4.74 (1H, m), 7.37 (1H, t, J=8 Hz), 7.61-7.68 (2H, m), 7.85 (1H, d, J=8 Hz).

Example 1m

Chiral form of 2-[(3R*,4S*)-1-{[2-chloro-6-(trifluoromethyl)phenyl]methyl}-3-{[1-(2-fluoropentyl)piperidin-4-yl]carbamoyl}-4-methylpyrrolidin-3-yl] acetic acid A mixture of the chiral form of tert-butyl 2-[(3R*,4S*)-1-{[2-chloro-6-(trifluoromethyl)phenyl]methyl}-3-{[1-(2-fluoropentyl)piperidin-4-yl]carbamoyl}-4-methylpyrrolidin-3-yl]acetate obtained in Example 11 (153 mg, 0.252 mmol), trifluoroacetic acid (2 ml, 26.9 mmol) and dichloromethane (dehydrated) (2 ml) was stirred at mom temperature for two hours and 35 minutes. The reaction mixture was concentrated, and the resulting residue was purified by silica gel column chromatography (ODS silica gel, elution solvent: water/methanol) to give the title compound (122 mg, yield 88%).

$^1$H-NMR (400 MHz, CDCl$_3$) δ ppm; 0.94-1.02 (6H, m), 1.32-1.70 (5H, m), 1.82-1.90 (1H, br), 2.07-2.20 (3H, m), 2.35-2.75 (8H, m), 2.81-3.05 (3H, m), 3.19 (1H, d, J=10 Hz), 3.63-3.75 (1H, m), 3.89 (1H, d, J=13 Hz), 4.00 (1H, d, J=13 Hz), 4.56-4.76 (1H, m), 7.40 (1H, t, J=8 Hz), 7.62-7.70 (2H, m), 8.52 (1H, d, J=7 Hz).

Example 2

2-[(3R*,4S*)-1-[(2,6-Dichlorophenyl)methyl]-3-({1-[(4,4-difluorocyclohexyl)methyl]piperidin-4-yl}carbamoyl)-4-methylpyrrolidin-3-yl]acetic acid Example 2a 4,4-Difluoro-N-methoxy-N-methylcyclohexane-1-carboxamide A mixture of ethyl 4,4-difluorocyclohexane-1-carboxylate (1.9 g, 9.88 mmol) and tetrahydrofuran (60 ml) was cooled to −70° C., and N,O-dimethylhydroxyamine hydrochloride (1.44 g, 14.8 mmol) was added. Further, 1.05 M n-propylmagnesium bromide (24.2 ml, 25.2 mmol) was added dropwise to the reaction mixture at −55° C. over five minutes so that the internal temperature did not exceed −35° C., and the reaction mixture was stirred at 0° C. for 30 minutes. A saturated aqueous ammonium chloride solution was added to the reaction mixture, which was extracted with ethyl acetate. The organic layer was dried over magnesium sulfate, and the solvent was distilled off. The residue was purified by silica gel column chromatography (elution solvent: ethyl acetate/heptane) to give the title compound (1.7 g, yield 83%).

$^1$H-NMR (400 MHz, CDCl$_3$) δ ppm; 1.65-1.95 (6H, br), 2.13-2.30 (2H, br), 2.70-2.82 (1H, br), 3.20 (3H, s), 3.70 (3H, s).

Example 2b 4,4-Difluorocyclohexane-1-carbaldehyde

A mixture of 4,4-difluoro-N-methoxy-N-methylcyclohexane-1-carboxamide obtained in Example 2a (1.7 g, 8.21 mmol) and tetrahydrofuran (60 ml) was cooled to −70° C., a 1.0 M diisobutylaluminum hydride/toluene solution (9.85 ml, 9.85 mmol) was added, and the reaction mixture was stirred at −60° C. for 35 minutes. A 1.0 M diisobutylaluminum hydride/toluene solution (5 ml, 5 mmol) was further added at −65° C., and the reaction mixture was stirred at −70° C. for two hours. A 2 N aqueous hydrochloric acid solution was added to the reaction mixture, which was extracted with ethyl acetate. The organic layer was dried over magnesium sulfate, and the solvent was distilled off to give a crude product of the title compound (1.4 g).

$^1$H-NMR (400 MHz, CDCl$_3$) δ ppm; 1.72-1.92 (4H, br), 1.95-2.18 (4H, br), 2.30-2.40 (1H, br), 9.68 (1H, s).

Example 2c tert-Butyl N-{1-[(4,4-difluorocyclohexyl)methyl]piperidin-4-yl}carbamate A mixture of the crude product of 4,4-difluorocyclohexane-1-carbaldehyde obtained in Example 2b (1.4 g) and tetrahydrofuran (100 ml) was cooled to 0° C., tert-butyl N-(piperidin-4-yl)carbamate (2.27 g, 11.3 mmol) was added thereto, followed by stirring for 20 minutes. Sodium triacetoxyborohydride (2.2 g, 10.4 mmol) was then added to the reaction mixture, which was stirred at mom temperature for eight hours. Brine was added to the reaction mixture, which was extracted with ethyl acetate. The organic layer was dried over magnesium sulfate, and the solvent was distilled off. The residue was purified by silica gel column chromatography (elution solvent: ethyl acetate/heptane). The resulting residue was dissolved in ethyl acetate and washed with a saturated aqueous sodium bicarbonate solution, and the solvent was then distilled off to give the title compound (650 mg, yield 20.7%).

$^1$H-NMR (400 MHz, CDCl$_3$) δ ppm; 1.15-2.20 (17H, m), 1.44 (9H, s), 2.70-2.85 (2H, br), 3.38-3.53 (1H, br), 4.37-4.50 (1H, br).

Example 2d

1-[(4,4-Difluorocyclohexyl)methyl]piperidin-4-amine

A 4 N hydrogen chloride/1,4-dioxane solution (11 ml, 43 mmol) was added to a mixture of tert-butyl N-{1-[(4,4-difluorocyclohexyl)methyl]piperidin-4-yl}carbamate obtained in Example 2c (650 mg, 1.96 mmol) and methanol (11 ml), followed by stirring at room temperature for three hours. After concentrating the reaction liquid, the residue was dissolved in ethyl acetate, a 1N aqueous sodium hydroxide solution was added, and the organic layer was separated. The aqueous layer was further extracted with ethyl acetate twice, the organic layers were dried over sodium sulfate, and the solvent was then distilled off to give the title compound (419 mg, yield 92%).

$^1$H-NMR (400 MHz, CDCl$_3$) δ ppm; 1.16-1.42 (7H, m), 1.59-2.16 (12H, m), 2.58-2.68 (1H, m), 2.74-2.82 (2H, m).

Example 2e (4-Methoxyphenyl)methyl (2E)-but-2-enoate

Crotonic acid (17.2 g, 200 mmol) was dissolved in N,N-dimethylformamide (100 ml) with cooling in an ice bath under nitrogen, and powdered potassium carbonate (15.2 g, 110 mmol) was added. The mixture was stirred for 30 minutes, and 4-methoxybenzyl chloride (29.8 g, 190 mmol) was then added dropwise over 15 minutes. The reaction mixture was stirred at mom temperature for four hours and at 45° C. for 14 hours. Ethyl acetate (500 ml) and water (200 ml) were added to the reaction liquid. The separated organic layer was washed with water (100 ml×2) and brine (100 ml). The aqueous layer was extracted with ethyl acetate (100 ml). The organic layers were combined, dried over magnesium sulfate, filtered and concentrated under reduced pressure to give a crude product of the title compound (40.51 g, yield: 98.2%).

$^1$H-NMR (400 MHz, CDCl$_3$) δ ppm; 1.87 (3H, dd, J=2, 7 Hz), 3.81 (3H, s), 5.10 (2H, s), 5.87 (1H, dq, J=2, 16 Hz), 6.86-6.92 (2H, m), 7.00 (1H, dq, J=7, 16 Hz), 7.28-7.34 (2H, m).

Example 2f (4-Methoxyphenyl)methyl (3RS,4SR)-1-benzyl-4-methylpyrrolidine-3-carboxylate The title compound (57.86 g, yield: 86.5%) was obtained from (4-methoxyphenyl)methyl (2E)-but-2-enoate obtained in Example 2e (40.6 g, 197 mmol) by a method similar to the method described in Example 1f.

$^1$H-NMR (400 MHz, CDCl$_3$) δ ppm; 1.12 (3H, d, J=7 Hz), 2.17-2.24 (1H, m), 2.46-2.62 (2H, m), 2.73-2.86 (2H, m), 2.87-2.93 (1H, m), 3.55 (1H, d, J=13 Hz), 3.63 (1H, d, J=13 Hz), 3.81 (3H, s), 5.03-5.10 (2H, m), 6.86-6.92 (2H, m), 7.21-7.35 (7H, m).

Example 2g (4-Methoxyphenyl)methyl (3RS,4SR)-1-benzyl-3-[2-(tert-butoxy)-2-oxoethyl]-4-methylpyrrolidine-3-carboxylate The title compound (60.3 g, yield: 80.1%) was obtained from (4-methoxyphenyl)methyl (3RS,4SR)-1-benzyl-4-methylpyrrolidine-3-carboxylate obtained in Example 2f (56.7 g, 166 mmol) by a method similar to the method described in Example 1g.

$^1$H-NMR (400 MHz, CDCl$_3$) δ ppm; 0.83 (3H, d, J=7 Hz), 1.35 (9H, s), 2.05-2.14 (2H, m), 2.51 (1H, d, J=17 Hz), 2.90-2.98 (2H, m), 3.60 (1H, d, J=13 Hz), 3.70 (1H, d, J=13 Hz), 3.81 (3H, s), 5.04 (1H, d, J=12 Hz), 5.07 (1H, d, J=12 Hz), 6.85-6.91 (2H, m), 7.19-7.34 (7H, m).

Example 2h

1-Benzyl 3-(4-methoxyphenyl)methyl (3RS,4SR)-3-[2-(tert-butoxy)-2-oxoethyl]-4-methylpyrrolidine-1,3-dicarboxylate The title compound (15 g, yield: 65.1%) was obtained from (4-methoxyphenyl)methyl (3RS,4SR)-1-benzyl-3-[2-(tert-butoxy)-2-oxoethyl]-4-methylpyrrolidine-3-carboxylate obtained in Example 2g (21 g, 46.3 mmol) by a method similar to the method described in Example 1h.

$^1$H-NMR (400 MHz, CDCl$_3$) δ ppm; 0.80-0.88 (3H, m), 1.38 (9H, d, J=5 Hz), 2.04-2.15 (1H, m), 2.22 (1H, dd, J=3, 7 Hz), 3.00-3.12 (2H, m), 3.30-3.36 (1H, m), 3.57-3.67 (1H, m), 3.79 (3H, d, J=4 Hz), 4.30 (1H, t, J=12 Hz), 5.00-5.16 (4H, m), 6.82-6.86 (2H, m), 7.23-7.39 (7H, m).
Analysis by HPLC;
(Analysis conditions) Column: CHIRALPAK AD-H (manufactured by Daicel Chemical Industries, Ltd.) (0.46 cm diameter×15 cm), 40° C., eluent: hexane/ethanol=9/1 (v/v), flow rate: 1 ml/min., detection: UV (210 nm)
(Analysis result) The resulting title compound was analyzed under the above analysis conditions, and a peak with a retention time of 7.14 minutes and a peak with a retention time of 9.06 minutes were observed.

Example 2i

1-Benzyl 3-(4-methoxyphenyl)methyl (3R*,4S*)-3-[2-(tert-butoxy)-2-oxoethyl]-4-methylpyrrolidine-1,3-dicarboxylate 1-Benzyl 3-(4-methoxyphenyl)methyl (3RS,4SR)-3-[2-(tert-butoxy)-2-oxoethyl]-4-methylpyrrolidine-1,3-dicarboxylate obtained in Example 2h (7.2 g, 14.5 mmol) was optically resolved repeatedly by HPLC(CHIRALPAK AD-H (2 cm diameter×25 cm), elution solvent: hexane/ethanol=85/15, flow rate: 8-10 ml/min.) to give a chiral form corresponding to the peak with a shorter retention time (2.92 g, yield: 40.5%).

Analysis by HPLC;
(Analysis conditions) Column: CHIRALPAK AD-H (manufactured by Daicel Chemical Industries, Ltd.) (0.46 cm diameter×15 cm), 40° C., eluent: hexane/ethanol=9/1 (v/v), flow rate: 1 ml/min., detection: UV (210 nm)
(Analysis result) The resulting chiral form was analyzed under the above analysis conditions to find that the retention time was 7.18 minutes and the enantiomeric excess was >99% ee.

Example 2j (3R*,4S*)-3-[2-(tert-Butoxy)-2-oxoethyl]-4-methylpyrrolidine-3-carboxylic acid Ethanol (50 ml) and 10% Pd/C (500 mg) were added to 1-benzyl 3-(4-methoxyphenyl)methyl (3R*,4S*)-3-[2-(tert-butoxy)-2-oxoethyl]-4-methylpyrrolidine-1,3-dicarboxylate obtained in Example 2i (2.92 g, 5.87 mmol), followed by stirring at mom temperature for 38 hours and five minutes under a hydrogen atmosphere. Water (100 ml) was added to the reaction liquid, which was stirred and filtered. The filtrate was concentrated to give the title compound (1.37 g, yield: 95.9%).
$^1$H-NMR (400 MHz, $D_2O$) δ ppm; 1.00 (3H, d, J=7 Hz), 1.45 (9H, s), 2.16-2.37 (1H, m), 2.33 (1H, d, J=17 Hz), 2.96 (1H, d, J=17 Hz), 3.05-3.11 (1H, m), 3.22 (1H, d, J=12 Hz), 3.50-3.56 (1H, m), 4.07 (1H, d, J=12 Hz).

Example 2k (3R*,4S*)-3-[2-(tert-Butoxy)-2-oxoethyl]-1-[(2,6-dichlorophenyl)methyl]-4-methylpyrrolidine-3-carboxylic acid 2,6-Dichlorobenzaldehyde (646 mg, 3.7 mmol) and sodium triacetoxyborohydride (782 mg, 3.7 mmol) were added to a mixture of (3R*,4S*)-3-[2-(tert-butoxy)-2-oxoethyl]-4-methylpyrrolidine-3-carboxylic acid obtained by the method of Example 2j (600 mg, 2.47 mmol), acetic acid (0.14 ml, 2.47 mmol) and methanol (10 ml), and the reaction mixture was stirred at room temperature for two hours. 2,6-Dichlorobenzaldehyde (430 mg, 2.5 mmol) and sodium triacetoxyborohydride (522 mg, 2.5 mmol) were further added, followed by stirring at an external temperature of 40° C. for 10.5 hours. Water was added to the reaction mixture, which was extracted with dichloromethane five times, and the organic layer was concentrated. The residue was purified by silica gel column chromatography (elution solvent: ethyl acetate/methanol) to give Lot A (32 mg) and Lot B (551 mg) of the title compound.
The chemical shift of Lot A is shown below. Lot B is a combination of three fractions upon column purification, and they were combined after confirming that the chemical shift of each fraction is similar to the chemical shift of Lot A.
$^1$H-NMR (400 MHz, $CDCl_3$) δ ppm; 1.01 (3H, d, J=7 Hz), 1.42 (9H, s), 2.05-2.11 (1H, m), 2.16-2.22 (1H, m), 2.65-2.69 (2H, m), 2.97-3.04 (2H, m), 3.70 (1H, d, J=10 Hz), 4.07-4.15 (2H, m), 7.22 (1H, dd, J=8, 9 Hz), 7.35 (2H, d, J=8 Hz).

Example 2l tert-Butyl 2-[(3R*,4S*)-1-[(2,6-dichlorophenyl)methyl]-3-({1-[(4,4-difluorocyclohexyl)methyl]piperidin-4-yl}carbamoyl)-4-methylpyrrolidin-3-yl]acetate The title compound (409 mg, yield: 92%) was obtained from 1-[(4,4-difluorocyclohexyl)methyl]piperidin-4-amine obtained in Example 2d (201 mg, 0.87 mmol) and (3R*,4S*)-3-[2-(tert-butoxy)-2-oxoethyl]-1-[(2,6-dichlorophenyl)methyl]-4-methylpyrrolidine-3-carboxylic acid obtained in Example 2k (290 mg, 0.72 mmol) by a method similar to the method described in Example 1k.
$^1$H-NMR (400 MHz, $CDCl_3$) δ ppm; 0.85-0.93 (3H, m), 1.15-2.14 (19H, m), 1.41 (9H, s), 2.57-2.71 (4H, m), 2.92 (1H, t, J=10 Hz), 3.12 (1H, d, J=16 Hz), 3.59-3.72 (2H, m), 3.96 (2H, s), 7.18 (1H, t, J=8 Hz), 7.33 (2H, d, J=8 Hz), 8.11 (1H, d, J=8 Hz).

Example 2m

2-[(3R*,4S*)-1-[(2,6-Dichlorophenyl)methyl]-3-({1-[(4,4-difluorocyclohexyl)methyl]piperidin-4-yl}carbamoyl)-4-methylpyrrolidin-3-yl]acetic acid The title compound (242 mg, yield: 66%) was obtained from tert-butyl 2-[(3R*,4S*)-1-[(2,6-dichlorophenyl)methyl]-3-({1-[(4,4-difluorocyclohexyl)methyl]piperidin-4-yl}carbamoyl)-4-methylpyrrolidin-3-yl]acetate obtained in Example 2l (409 mg, 0.66 mmol) by a method similar to the method described in Example 1m.
$^1$H-NMR (400 MHz, $CD_3OD$) δ ppm; 0.87-0.93 (3H, m), 1.20-2.38 (19H, m), 2.62-2.71 (2H, m), 2.86-3.12 (4H, m), 3.61-3.73 (2H, m), 4.01-4.09 (2H, m), 7.29 (1H, dd, J=8, 9 Hz), 7.43 (2H, d, J=8 Hz).

Example 3

2-[(3R*,4S*)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl] acetic acid Example 3a tert-Butyl 4-[(3R*,4S*)-1-benzyl-3-[2-(tert-butoxy)-2-oxoethyl]-4-methylpyrrolidin-3-amido]piperidine-1-carboxylate tert-Butyl 4-aminopiperidine-1-carboxylate (849 mg, 4.24 mmol), triethylamine (1.18 ml, 8.48 mmol) and PyBOP (2.21 g, 4.24 mmol) were added to a solution of (3R*,4S*)-1-benzyl-3-[2-(tert-butoxy)-2-oxoethyl]-4-methylpyrrolidine-3-carboxylic acid obtained by a method similar to that of Example 1j (942 mg, 2.83 mmol) in N,N-dimethylformamide (20 ml), followed by stirring at mom temperature overnight. Ethyl acetate was added to the reaction liquid, which was washed with a 1N aqueous sodium hydroxide solution and brine. This was dried over anhydrous magnesium sulfate and concentrated. The residue was purified by silica gel column chromatography (elution solvent: heptane/ethyl acetate) to give the title compound (1.33 g, yield: 91.1%).
$^1$H-NMR (400 MHz, $CDCl_3$) δ ppm; 0.92 (3H, d, J=7 Hz), 1.20-1.40 (2H, m), 1.40 (9H, s), 1.48 (9H, s), 1.78-1.88 (1H, m), 1.92-1.98 (1H, br), 1.96 (1H, d, J=16 Hz), 2.03-2.09 (1H, m), 2.36 (1H, d, J=10 Hz), 2.58-2.68 (2H, m), 2.89-2.95 (2H, m), 3.10 (1H, d, J=16 Hz), 3.59 (1H, d, J=10 Hz), 3.66 (2H, s), 3.83-4.00 (3H, m), 7.23-7.35 (5H, m), 8.65 (1H, d, J=7 Hz).
MS (ESI) m/z: 538.2 (M+Na)$^+$.

Example 3b tert-Butyl 4-[(3R*,4S*)-3-[2-(tert-butoxy)-2-oxoethyl]-4-methylpyrrolidin-3-amido]piperidine-1-carboxylate 20% palladium hydroxide (724 mg) was added to a solution of tert-butyl 4-[(3R*,4S*)-1-benzyl-3-[2-(tert-butoxy)-

2-oxoethyl]-4-methylpyrrolidin-3-amido]piperidine-1-carboxylate obtained in Example 3a (1.33 g, 2.58 mmol) in methanol (30 ml), which was stirred under a hydrogen atmosphere overnight. The reaction liquid was filtered and concentrated under reduced pressure to give the title compound (1.04 g, yield: 94.7%).

$^1$H-NMR (400 MHz, CDCl$_3$) δ ppm; 0.92 (3H, d, J=7 Hz), 1.20-1.52 (2H, m), 1.41 (9H, s), 1.43 (9H, s), 1.80-2.10 (5H, m), 2.00 (1H, d, J=16 Hz), 2.55-2.61 (1H, m), 2.80-3.06 (2H, m), 2.92 (1H, d, J=10 Hz), 3.12 (1H, d, J=16 Hz), 3.35 (1H, d, J=9 Hz), 3.70 (1H, d, J=10 Hz), 3.80-4.00 (3H, m), 8.30 (1H, d, J=7 Hz).

MS (ESI) m/z: 426.1 (M+H)$^+$.

Example 3c tert-Butyl 4-[(3R*,4S*)-3-[2-(tert-butoxy)-2-oxoethyl]-1-{[2-chloro-6-(trifluoromethyl)phenyl]methyl}-4-methylpyrrolidin-3-amido]piperidine-1-carboxylate 2-(Bromomethyl)-1-chloro-3-(trifluoromethyl)benzene (443 mg, 1.62 mmol) and potassium carbonate (244 mg) were added to a solution of tert-butyl 4-[(3R*,4S*)-3-[2-(tert-butoxy)-2-oxoethyl]-4-methylpyrrolidin-3-amido]piperidine-1-carboxylate obtained in Example 3b (345 mg, 0.811 mmol) in N,N-dimethylformamide (dehydrated) (10 mL), which was stirred at 45° C. for six hours and at 40° C. for two days. Ethyl acetate was added to the reaction liquid, which was washed with a 1N aqueous sodium hydroxide solution and brine. This was dried over anhydrous magnesium sulfate and concentrated. The residue was purified by silica gel column chromatography (elution solvent: heptane/ethyl acetate) to give the title compound (320 mg, yield: 63.8%).

$^1$H-NMR (400 MHz, CDCl$_3$) δ ppm; 0.92 (3H, d, J=7 Hz), 1.13-1.18 (2H, m), 1.39 (9H, s), 1.49 (9H, s), 1.53-1.65 (1H, m), 1.76-1.86 (1H, m), 1.98 (1H, d, J=16 Hz), 2.02-2.10 (1H, m), 2.51 (1H, d, J=10 Hz), 2.60-2.80 (3H, m), 2.88 (1H, t, J=10 Hz), 3.12 (1H, d, J=16 Hz), 3.53 (1H, d, J=10 Hz), 4.09-4.25 (5H, m), 7.38 (1H, t, J=8 Hz), 7.63 (2H, d, J=8 Hz), 7.96 (1H, d, J=8 Hz).

MS (ESI) m/z: 640.2 (M+Na)$^+$.

Example 3d

2-[(3R*,4S*)-1-{[2-Chloro-6-(trifluoromethyl)phenyl]methyl}-4-methyl-3-[(piperidin-4-yl)carbamoyl]pyrrolidin-3-yl]acetic acid Trifluoroacetic acid (8 mL) was added to a solution of tert-butyl 4-[(3R*,4S*)-3-[2-(tert-butoxy)-2-oxoethyl]-1-{[2-chloro-6-(trifluoromethyl)phenyl]methyl}-4-methylpyrrolidin-3-amido]piperidine-1-carboxylate obtained in Example 3c (320 mg, 0.518 mmol) in dichloromethane (dehydrated) (8 mL) under ice-cooling, followed by stirring at room temperature for 2.5 hours. The reaction liquid was concentrated under reduced pressure, and the residue was purified by ODS column chromatography (elution solvent: water/methanol) to give a mixture containing the title compound (344 mg).

$^1$H-NMR (400 MHz, CD$_3$OD) δ ppm; 0.83 (3H, d, J=5 Hz), 1.43-1.63 (2H, m), 1.76-1.89 (1H, m), 1.92-2.00 (1H, m), 2.03-2.19 (2H, m), 2.55-2.68 (2H, m), 2.91-3.10 (4H, m), 3.25-3.36 (2H, m), 3.45-3.59 (1H, m), 3.75-4.18 (3H, m), 7.41-7.76 (3H, m).

MS (ESI) m/z: 462.3 (M+H)$^+$

Example 3e

2-[(3R*,4S*)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl] acetic acid Cyclohex-1-ene-1-carbaldehyde (423 µl, 3.73 mmol), acetic acid (300 µl) and sodium triacetoxyborohydride (789 mg, 3.73 mmol) were added to a solution of the mixture of 2-[(3R*,4S*)-1-{[2-chloro-6-(trifluoromethyl)phenyl]methyl}-4-methyl-3-[(piperidin-4-yl)carbamoyl]pyrrolidin-3-yl]acetic acid obtained by the method of Example 3d (344 mg, 0.745 mmol) in tetrahydrofuran (dehydrated) (10 mL), followed by stirring overnight. Water and methanol were added to the reaction liquid, which was concentrated under reduced pressure, and the residue was purified by ODS column chromatography (elution solvent: water/methanol). The purified product was dissolved in dichloromethane, suspended by adding hexane and concentrated to give the title compound (180 mg, yield: 43.4%).

$^1$H-NMR (400 MHz, CD$_3$OD) δ ppm; 0.89 (3H, d, J=7 Hz), 1.23-1.38 (2H, m), 1.44-1.82 (6H, m), 1.82-1.96 (1H, m), 1.96-2.25 (5H, m), 2.30-2.45 (2H, m), 2.55-2.68 (2H, m), 2.92-3.20 (5H, m), 3.54 (1H, d, J=10 Hz), 3.64-3.78 (1H, m), 3.95 (1H, d, J=10 Hz), 4.05 (1H, d, J=10 Hz), 5.76 (1H, s), 7.47-7.52 (1H, m), 7.72 (1H, d, J=7 Hz), 7.77 (1H, d, J=8 Hz).

MS (ESI) m/z: 578.3 (M+Na)$^+$

Example 4

Another method for compound of Example 3

2-[(3R*,4S*)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl] acetic acid

Example 4a tert-Butyl N-[1-(cyclohex-1-en-1-ylmethyl)piperidin-4-yl]carbamate A mixture of tert-butyl N-(piperidin-4-yl)carbamate (5.3 g, 26.5 mmol), 1-cyclohexane-1-carboxaldehyde (3.5 g, 31.8 mmol), sodium triacetoxyborohydride (7.29 g, 34.4 mmol), acetic acid (0.5 ml) and tetrahydrofuran (dehydrated) (80 ml) was stirred at room temperature for 85 hours and 30 minutes. Water and sodium bicarbonate were added to the reaction mixture, which was stirred and then extracted with ethyl acetate twice. The organic layer was washed with brine and dried over anhydrous sodium sulfate, and the solvent was distilled off. The residue was purified by silica gel column chromatography (NH silica gel, elution solvent: ethyl acetate/heptane) to give the title compound (7.47 g, yield: 95.7%).

$^1$H-NMR (400 MHz, CDCl$_3$) δ ppm; 1.35-1.50 (2H, m), 1.44 (9H, s), 1.51-1.65 (4H, m), 1.84-2.03 (8H, m), 2.68-2.80 (4H, m), 3.39-3.50 (1H, m), 4.38-4.48 (1H, m), 5.54 (1H, s).

Example 4b 1-(Cyclohex-1-en-1-ylmethyl)piperidin-4-amine

A mixture of tert-butyl N-[1-(cyclohex-1-en-1-ylmethyl)piperidin-4-yl]carbamate obtained in Example 4a (7.47 g, 25.4 mmol), a 5 N aqueous hydrochloric acid solution (25 ml, 125 mmol) and methanol (100 ml) was stirred at 70° C. for 1.5

Example 4c

1-Benzyl 3-(4-methoxyphenyl)methyl (3RS,4SR)-3-[2-(tert-butoxy)-2-oxoethyl]-4-methylpyrrolidine-1,3-dicarboxylate A solution of (4-methoxyphenyl)methyl (3RS,4SR)-1-benzyl-3-[2-(tert-butoxy)-2-oxoethyl]-4-methylpyrrolidine-3-carboxylate obtained in Example 2g (18 g, 39.7 mmol) in dichloromethane (85.7 ml) was adjusted to an internal temperature of 10 to 20° C., and benzyl chloroformate (11.9 ml, 79.4 mmol) was added thereto. After returning to mom temperature and stirring for 0.5 hour, the reaction mixture was concentrated directly. The resulting crude product was purified by column chromatography (silica gel, elution solvent: ethyl acetate/heptane) to give the title compound (12.89 g, yield: 65.3%).

$^1$H-NMR (400 MHz, CDCl$_3$) δ ppm; 0.80-0.88 (3H, m), 1.38 (9H, d, J=5 Hz), 2.04-2.15 (1H, m), 2.22 (1H, dd, J=3, 17 Hz), 3.00-3.12 (2H, m), 3.62 (1H, m), 3.79 (3H, d, J=4 Hz), 4.30 (1H, t, J=12 Hz), 5.00-5.16 (4H, m), 6.82-6.86 (2H, m), 7.23-7.39 (8H, m).

Example 4d

1-Benzyl 3-(4-methoxyphenyl)methyl (3R*,4S*)-3-[2-(tert-butoxy)-2-oxoethyl]-4-methylpyrrolidine-1,3-dicarboxylate 1-Benzyl 3-(4-methoxyphenyl)methyl (3RS,4SR)-3-[2-(tert-butoxy)-2-oxoethyl]-4-methylpyrrolidine-1,3-dicarboxylate obtained in Example 4c (12.7 g, 26 mmol) was optically resolved repeatedly by HPLC (CHIRALPAK AD-H (2 cm diameter×25 cm), elution solvent: hexane/ethanol=85/15, flow rate: 8-10 ml/min.) to give a chiral form corresponding to the peak with a shorter retention time (5.7 g, yield: 44.9%). The resulting chiral form (5.3 g) was further purified by silica gel column chromatography (elution solvent; heptane/ethyl acetate) in two portions to give 5.2 g of the title compound.

$^1$H-NMR (400 MHz, CDCl$_3$) δ ppm; 0.81-0.88 (3H, m), 3.37-3.38 (9H, m), 2.04-2.16 (1H, m), 2.19-2.25 (1H, m), 3.00-3.12 (2H, m), 3.30-3.36 (1H, m), 3.56-3.67 (1H, m), 3.75-3.79 (3H, m), 4.26-4.33 (1H, m), 5.00-5.16 (4H, m), 6.82-6.86 (2H, m), 7.27-7.37 (7H, m).

Analysis by HPLC;
(Analysis conditions) Column: CHIRALPAK AD-H (manufactured by Daicel Chemical Industries, Ltd.) (0.46 cm diameter×15 cm), 40° C., eluent: hexane/ethanol=9/1 (v/v), flow rate: 1 ml/min., detection: UV (210 nm)
(Analysis result) The purified chiral form was analyzed under the above analysis conditions to find that the retention time was 7.15 minutes and the enantiomeric excess was >99% ee.

Example 4e

1-Benzyl 3-(4-methoxyphenyl)methyl (3R*,4S*)-3-[2-(tert-butoxy)-2-oxoethyl]-4-methylpyrrolidine-1,3-dicarboxylate 1-Benzyl 3-(4-methoxyphenyl)methyl (3RS,4SR)-3-[2-(tert-butoxy)-2-oxoethyl]-4-methylpyrrolidine-1,3-dicarboxylate obtained by a method similar to that of Example 4c (7.8 g, 16.5 mmol) was optically resolved repeatedly by HPLC (CHIRALPAK AD-H, elution solvent: hexane/ethanol=85/15) to give a chiral form with a shorter retention time (3.3 g, yield: 42.3%).

Example 4f (3R*,4S*)-3-[2-(tert-Butoxy)-2-oxoethyl]-4-methylpyrrolidine-3-carboxylic acid Methanol (70 ml) and 10% Pd/C (600 mg) were added to 1-benzyl 3-(4-methoxyphenyl)methyl (3R*,4S*)-3-[2-(tert-butoxy)-2-oxoethyl]-4-methylpyrrolidine-1,3-dicarboxylate obtained by the method of Example 4e (3.3 g, 6.63 mmol), followed by stirring at mom temperature for three days under a hydrogen atmosphere. Water (70 ml) was added to the reaction liquid, which was stirred and filtered. The filtrate was concentrated to give the title compound (1.15 g, yield: 71.3%).

$^1$H-NMR (400 MHz, D$_2$O) was identical to that of the compound obtained in Example 2j.

Example 4g (3R*,4S*)-3-[2-(tert-Butoxy)-2-oxoethyl]-4-methylpyrrolidine-3-carboxylic acid Methanol (3 ml) and 10% Pd/C (30 mg) were added to 1-benzyl 3-(4-methoxyphenyl)methyl (3R*,4S*)-3-[2-(tert-butoxy)-2-oxoethyl]-4-methylpyrrolidine-1,3-dicarboxylate which is obtained in Example 4d and which is without silica gel column chromatography purification (104 mg, 0.21 mmol), followed by stirring at mom temperature overnight under a hydrogen atmosphere. Water was added to the reaction liquid, which was stirred and filtered. The filtrate was concentrated to give the title compound (48.7 mg, yield: 95.3%).

$^1$H-NMR (400 MHz, D$_2$O) was identical to that of the compound obtained in Example 2j.

Example 4h (3R*,4S*)-3-[2-(tert-Butoxy)-2-oxoethyl]-4-methylpyrrolidine-3-carboxylic acid Methanol (100 ml) and 10% Pd/C (559 mg) were added to 1-benzyl 3-(4-methoxyphenyl)methyl (3R*,4S*)-3-[2-(tert-butoxy)-2-oxoethyl]-4-methylpyrrolidine-1,3-dicarboxylate obtained in Example 4d (5.2 g, 10.5 mmol), followed by stirring at mom temperature for eight hours and 15 minutes under a hydrogen atmosphere. Water (100 ml) was added to the reaction liquid, which was stirred for one hour and filtered. The filtrate was concentrated. A combination (3.2 g, 13.2 mmol) of the residue and (3R*,4S*)-3-[2-(tert-butoxy)-2-oxoethyl]-4-methylpyrrolidine-3-carboxylic acid obtained in Examples 2j, 4f and 4g was suspended by adding methanol (25 ml) and stirred at room temperature for 30 minutes, and collection by filtration gave 3.02 g of the title compound.

--- hours. The reaction mixture was ice-cooled, a 5 N aqueous sodium hydroxide solution (25 ml, 125 mmol) was added, and the solvent was distilled off. Water was added to the residue, which was extracted with ethyl acetate twice. The organic layer was washed with brine and dried over anhydrous sodium sulfate, and the solvent was distilled off to give the title compound (4.73 g, yield: 95.8%).

$^1$H-NMR (400 MHz, CDCl$_3$) δ ppm; 1.30-1.50 (4H, m), 1.51-1.70 (4H, m), 1.75-2.08 (8H, m), 2.59-2.68 (1H, m), 2.72-2.88 (4H, m), 5.55 (1H, s).

¹H-NMR (400 MHz, D₂O) δ ppm; 0.98 (3H, d, J=7 Hz), 1.43 (9H, s), 2.14-2.24 (1H, m), 2.31 (1H, d, J=17 Hz), 2.94 (1H, d, J=17 Hz), 3.06 (1H, t, J=11 Hz), 3.20 (1H, d, J=12 Hz), 3.51 (1H, dd, J=8, 12 Hz), 4.05 (1H, d, J=12 Hz).

Example 4i tert-Butyl 2-[(3R*,4S*)-1-{[2-chloro-6-(trifluoromethyl)phenyl]methyl}-3-{[1-(cyclohex-1-en-1-ylmethyl)piperidin-4-yl]carbamoyl}-4-methylpyrrolidin-3-yl]acetate 1-(Cyclohex-1-en-1-ylmethyl)piperidin-4-amine obtained in Example 4b (240 mg, 1.24 mmol), N,N-dimethylformamide (3 ml), triethylamine (344 μl, 2.47 mmol) and PyBOP (856 mg, 1.64 mmol) were added to (3R*,4S*)-3-[2-(tert-butoxy)-2-oxoethyl]-4-methylpyrrolidine-3-carboxylic acid obtained in Example 4h (200 mg, 0.822 mmol), followed by stirring with heating in a 45° C. oil bath for 1.5 hours. Water was added to the reaction mixture, which was extracted with ethyl acetate. The organic layer was dried over magnesium sulfate and concentrated. 2-(Bromomethyl)-1-chloro-3-(trifluoromethyl)benzene (247 mg, 0.903 mmol), potassium carbonate (170 mg, 1.23 mmol) and N,N-dimethylformamide (1 ml) were added thereto, followed by heating with stirring in a 45° C. oil bath for three hours. Water was added to the reaction mixture, which was extracted with ethyl acetate. The organic layer was washed with water and brine and then dried over magnesium sulfate. The resulting crude product was purified by column chromatography twice (NH silica gel, elution solvent: ethyl acetate/heptane and silica gel, elution solvent: ethyl acetate/heptane) to give the title compound (353 mg, yield 70.1%).

¹H-NMR (400 MHz, CDCl₃) δ ppm; 0.91 (3H, d, J=7 Hz), 1.31-1.42 (2H, m), 1.39 (9H, s), 1.54-1.66 (5H, m), 1.81-2.09 (9H, m), 2.53 (1H, d, J=10 Hz), 2.63-2.77 (5H, m), 2.88 (1H, t, J=10 Hz), 3.11 (1H, d, J=16 Hz), 3.56 (1H, d, J=10 Hz), 3.61-3.72 (1H, m), 3.92 (1H, d, J=13 Hz), 3.98 (1H, d, J=13 Hz), 5.54 (1H, s), 7.36 (1H, t, J=8 Hz), 7.62 (1H, d, J=4 Hz), 7.64 (1H, d, J=4 Hz), 7.83 (1H, d, J=8 Hz).

Example 4j

2-[(3R*,4S*)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl] acetic acid Trifluoroacetic acid (1.5 ml, 20.3 mmol) was added to a solution of tert-butyl 2-[(3R*,4S*)-1-{[2-chloro-6-(trifluoromethyl)phenyl]methyl}-3-{[1-(cyclohex-1-en-1-ylmethyl)piperidin-4-yl]carbamoyl}-4-methylpyrrolidin-3-yl] acetate obtained in Example 4i (353 mg, 0.577 mmol) in dichloromethane (400 μl), which was stirred at mom temperature for two hours. The reaction mixture was concentrated under reduced pressure and purified by ODS column chromatography (elution solvent: methanol/water) to give the title compound (215 mg, yield 67%).

¹H-NMR (400 MHz, CDCl₃) δ ppm; 1.01 (3H, d, J=7 Hz), 1.22-1.34 (2H, m), 1.42-1.68 (7H, m), 1.79-2.07 (6H, m), 2.38-2.46 (1H, m), 2.49 (1H, d, J=10 Hz), 2.56 (1H, d, J=14 Hz), 2.67-2.82 (6H, m), 3.00 (1H, t, J=10 Hz), 3.16 (1H, d, J=10 Hz), 3.63-3.76 (1H, m), 3.88 (1H, d, J=14 Hz), 4.01 (1H, d, J=14 Hz), 5.55 (1H, s), 7.40 (1H, t, J=8 Hz), 7.64 (1H, d, J=4 Hz), 7.66 (1H, d, J=4 Hz), 8.56 (1H, d, J=8 Hz)

Specific rotation: $[\alpha]_D^{29}$ +37.1 (c 0.11, MeOH)

Example 5

Another method for compound of Example 3

2-[(3R*,4S*)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl] acetic acid Example 5a tert-Butyl 4-[(3RS,4SR)-3-[2-(tert-butoxy)-2-oxoethyl]-1-[(2,6-dichlorophenyl)methyl]-4-methylpyrrolidin-3-amido]piperidine-1-carboxylate 20% palladium hydroxide (300 mg) was added to a solution of benzyl (3RS,4SR)-1-benzyl-3-[2-(tert-butoxy)-2-oxoethyl]-4-methylpyrrolidine-3-carboxylate obtained by a method similar to that of Example 1g (3 g, 7.08 mmol) in methanol (200 ml), followed by stirring at mom temperature overnight under a hydrogen atmosphere. The reaction liquid was filtered and washed with methanol. Warm water at about 40° C. was added to the product collected by filtration to dissolve the solid, followed by filtration. The filtrate was concentrated together with the first filtrate to give a deprotected form (1.7 g).

Methanol (44 ml), 2,6-dichlorobenzaldehyde (4.83 g, 27.6 mmol) and acetic acid (1.1 ml, 18.4 mmol) were added to the deprotected form obtained by a method similar to the above method (4.47 g, 18.4 mmol), followed by stirring at room temperature for 15 minutes, and sodium triacetoxyborohydride (6.16 g, 27.6 mmol) was added, followed by heating with stirring at 40° C. overnight. Neutral buffer [prepared from potassium dihydrogenphosphate (13.65 g), disodium hydrogenphosphate dodecahydrate (71.6 g) and water (1.5 l)] was added to the reaction liquid, ethyl acetate and heptane were added, and the mixture was filtered. The filtrate was extracted with ethyl acetate, the organic layer was dried over sodium sulfate and concentrated, and the resulting crude product was then purified by column chromatography (silica gel, elution solvent: methanol/ethyl acetate) and combined with the product collected by filtration to give (3RS,4SR)-3-[2-(tert-butoxy)-2-oxoethyl]-1-[(2,6-dichlorophenyl)methyl]-4-methylpyrrolidine-3-carboxylic acid (3.9 g). tert-Butyl 4-aminopiperidine-1-carboxylate (974 mg, 4.89 mmol), N,N-dimethylformamide (10 ml), triethylamine (1.14 ml, 8.13 mmol) and PyBOP (2.54 g, 4.89 mmol) were added to this compound (1.64 g, 4.07 mmol), followed by stirring at mom temperature overnight. Water was added to the reaction liquid, which was extracted with ethyl acetate, and the organic layer was then washed with water and brine and dried over magnesium sulfate. The crude product obtained by concentration was purified by column chromatography (NH silica gel, elution solvent: ethyl acetate/heptane) to give the title compound (2.10 g, yield: 88.1%).

¹H-NMR (400 MHz, CDCl₃) δ ppm; 0.91 (3H, d, J=7 Hz), 1.15-1.34 (2H, m), 1.40 (9H, s), 1.49 (9H, s), 1.58-1.70 (2H, m), 1.76-1.84 (1H, br), 1.98 (1H, d, J=16 Hz), 2.03-2.13 (1H, m), 2.54-2.65 (2H, m), 2.66-2.88 (2H, br), 2.92 (1H, t, J=10 Hz), 3.11 (1H, d, J=16 Hz), 3.59 (1H, d, J=10 Hz), 3.81-3.90 (1H, m), 3.95 (2H, s), 3.90-4.07 (2H, br), 7.18 (1H, dd, J=7, 8 Hz), 7.33 (1H, d, J=8 Hz), 8.23 (1H, d, J=8 Hz).

Analysis by HPLC;
(Analysis conditions) Column: CHIRALPAK IA (manufactured by Daicel Chemical Industries, Ltd.) (0.46 cm diameter×15 cm), 40° C., eluent: hexane/ethanol=95/5 (v/v), flow rate: 1 ml/min., detection: UV (210 nm)

(Analysis result) The resulting title compound was analyzed under the above analysis conditions, and a peak with a retention time of 3.46 minutes and a peak with a retention time of 6.04 minutes were observed.

Example 5b tert-Butyl 4-[(3R*,4S*)-3-[2-(tert-butoxy)-2-oxoethyl]-1-[(2,6-dichlorophenyl)methyl]-4-methylpyrrolidin-3-amido]piperidine-1-carboxylate tert-Butyl 4-[(3RS,4SR)-3-[2-(tert-butoxy)-2-oxoethyl]-1-[(2,6-dichlorophenyl)methyl]-4-methylpyrrolidin-3-amido]piperidine-1-carboxylate obtained in Example 5a (2.04 g, 3.49 mmol) was optically resolved repeatedly by HPLC (CHIRALPAK IA (3 cm diameter×25 cm), elution solvent: hexane/ethanol=94/6, flow rate: 22 ml/min.) to give the title compound (a chiral form corresponding to the peak with a shorter retention time) (859 mg, 42.1%) and the optical isomer (a chiral form corresponding to the peak with a longer retention time) (817 mg, 40%), respectively.

Chiral form corresponding to the peak with a shorter retention time; $^1$H-NMR (400 MHz, CDCl$_3$) δ ppm; 0.91 (3H, d, J=7 Hz), 1.15-1.33 (2H, m), 1.40 (9H, s), 1.49 (9H, s), 1.76-1.84 (1H, m), 1.98 (1H, d, J=16 Hz), 2.01-2.11 (1H, m), 2.57 (1H, d, J=10 Hz), 2.57-2.64 (1H, m), 2.69-2.82 (2H, m), 2.92 (1H, t, J=10 Hz), 3.11 (1H, d, J=16 Hz), 3.59 (1H, d, J=10 Hz), 3.80-4.09 (2H, m), 3.95 (2H, s), 7.18 (1H, t, J=8 Hz), 7.33 (2H, d, J=8 Hz), 8.23 (1H, d, J=8 Hz).
Analysis by HPLC;
(Analysis conditions) Column: CHIRALPAK IA (manufactured by Daicel Chemical Industries, Ltd.) (0.46 cm diameter×15 cm), 40° C., eluent: hexane/ethanol=95/5 (v/v), flow rate: 1 ml/min., detection: UV (210 nm)
(Analysis result) The resulting chiral form corresponding to the peak with a shorter retention time was analyzed under the above analysis conditions to find that the retention time was 3.44 minutes and the enantiomeric excess was >99% ee.

Example 5c tert-Butyl 4-[(3R*,4S*)-3-[2-(tert-butoxy)-2-oxoethyl]-1-{[2-chloro-6-(trifluoromethyl)phenyl]methyl}-4-methylpyrrolidin-3-amido]piperidine-1-carboxylate 20% palladium hydroxide (75.8 mg) was added to a solution of tert-butyl 4-[(3R*,4S*)-3-[2-(tert-butoxy)-2-oxoethyl]-1-[(2,6-dichlorophenyl)methyl]-4-methylpyrrolidin-3-amido]piperidine-1-carboxylate obtained in Example 5b (a chiral form corresponding to the peak with a shorter retention time) (758 mg, 1.29 mmol) in methanol (20 ml), followed by stirring at 40° C. for three hours under a hydrogen atmosphere. The reaction liquid was filtered, and the filtrate was concentrated to give a crude product (501 mg). 2-(Bromomethyl)-1-chloro-3-(trifluoromethyl)benzene (145 mg, 0.532 mmol) and potassium carbonate (53.2 mg) were added to a solution of this crude product (174 mg) in N,N-dimethylformamide (dehydrated) (6 mL), followed by stirring overnight. 2-(Bromomethyl)-1-chloro-3-(trifluoromethyl)benzene (145 mg, 0.532 mmol) and potassium carbonate (106 mg) were further added, followed by stirring for four hours. Ethyl acetate was added to the reaction liquid, which was washed with a 1N aqueous sodium hydroxide solution and brine. This was dried over anhydrous magnesium sulfate and concentrated. The residue was purified by silica gel column chromatography (elution solvent: heptane/ethyl acetate) to give the title compound (82 mg, yield: 32.4%).
$^1$H-NMR (400 MHz, CDCl$_3$) δ ppm; 0.92 (3H, d, J=7 Hz), 1.12-1.18 (2H, m), 1.39 (9H, s), 1.49 (9H, s), 1.53-1.65 (1H, m), 1.76-1.86 (1H, m), 1.98 (1H, d, J=16 Hz), 2.02-2.10 (1H, m), 2.51 (1H, d, J=10 Hz), 2.61-2.81 (3H, m), 2.89 (1H, t, J=10 Hz), 3.12 (1H, d, J=16 Hz), 3.53 (1H, d, J=10 Hz), 3.80-4.10 (5H, m), 7.38 (1H, t, J=8 Hz), 7.63 (2H, d, J=8 Hz), 7.96 (1H, d, J=8 Hz).
MS (ESI) m/z: 618.1 (M+H)$^+$ Example 5d 2-[(3R*,4S*)-1-{[2-Chloro-6-(trifluoromethyl)phenyl]methyl}-4-methyl-3-[(piperidin-4-yl)carbamoyl]pyrrolidin-3-yl]acetic acid Trifluoroacetic acid (3 mL) was added to a solution of tert-butyl 4-[(3R*,4S*)-3-[2-(tert-butoxy)-2-oxoethyl]-1-{[2-chloro-6-(trifluoromethyl)phenyl]methyl}-4-methylpyrrolidin-3-amido]piperidine-1-carboxylate obtained in Example 5c (82 mg, 0.133 mmol) in dichloromethane (dehydrated) (3 mL) under ice-cooling, followed by stirring at room temperature for 2.5 hours. The reaction liquid was concentrated under reduced pressure, and the residue was purified by ODS column chromatography (elution solvent: water/methanol) to give the title compound (72 mg, yield: quant.).
$^1$H-NMR (400 MHz, CD$_3$OD) δ ppm; 0.90 (3H, d, J=5 Hz), 1.51-1.70 (2H, m), 1.82-1.91 (1H, m), 1.99-2.08 (1H, m), 2.12-2.23 (2H, m), 2.61 (1H, d, J=9 Hz), 2.60-2.70 (2H, m), 2.95-3.12 (4H, m), 3.25-3.36 (2H, m), 3.53 (1H, d, J=9 Hz), 3.83-3.92 (1H, m), 3.97 (1H, d, J=13 Hz), 4.07 (1H, d, J=13 Hz), 7.51 (1H, t, J=8 Hz), 7.73 (1H, d, J=8 Hz), 7.78 (1H, d, J=8 Hz).
MS (ESI) m/z: 462.2 (M+H)$^+$ Example 5e 2-[(3R*,4S*)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl]acetic acid Cyclohex-1-ene-1-carbaldehyde (25.9 µl, 0.227 mmol), acetic acid (30 µl) and sodium triacetoxyborohydride (68.8 mg, 0.325 mmol) were added to a solution of 2-[(3R*,4S*)-1-{[2-chloro-6-(trifluoromethyl)phenyl]methyl}-4-methyl-3-[(piperidin-4-yl)carbamoyl]pyrrolidin-3-yl]acetic acid obtained by the method of Example 5d (15 mg, 0.0325 mmol) in tetrahydrofuran (dehydrated) (2 mL), followed by stirring overnight. Water and methanol were added to the reaction liquid, which was concentrated under reduced pressure, and the residue was purified by ODS column chromatography (elution solvent: water/methanol) to give the title compound (12.8 mg, yield: 70.8%).
$^1$H-NMR (400 MHz, CD$_3$OD) δ ppm; 0.89 (3H, d, J=7 Hz), 1.50-1.90 (2H, m), 1.83-1.95 (1H, m), 2.00-2.22 (5H, m), 2.30-2.45 (2H, m), 2.57-2.68 (2H, m), 2.92-3.14 (5H, m), 3.54 (1H, d, J=10 Hz), 3.64-3.78 (1H, m), 3.95 (1H, d, J=13 Hz), 4.05 (1H, d, J=13 Hz), 5.76 (1H, s), 7.49 (1H, t, J=8 Hz), 7.72 (1H, d, J=8 Hz), 7.77 (1H, d, J=8 Hz).
MS (ESI) m/z: 556.3 (M+H)$^+$

Example 6

2-[(3R*,4S*)-1-[(2-Chloro-6-methylphenyl)methyl]-3-{[1-(cyclohex-1-en-1-ylmethyl)piperidin-4-yl]carbamoyl}-4-methylpyrrolidin-3-yl]acetic acid

Example 6a (3R*,4S*)-3-[2-(tert-Butoxy)-2-oxoethyl]-1-[(2-chloro-6-methylphenyl)methyl]-4-methylpyrrolidine-3-carboxylic acid The title compound (154 mg, yield 27.2%) was obtained from (3R*,4S*)-3-[2-(tert-butoxy)-2-oxoethyl]-4-methylpyrrolidine-3-carboxylic acid obtained by a method similar to that of Example 11 (360 mg, 1.48 mmol) and 2-chloro-6-methylbenzaldehyde (416 mg, 2.69 mmol) by a method similar to the method described in Example 1j.

$^1$H-NMR (400 MHz, CDCl$_3$) δ ppm; 1.01 (3H, d, J=7 Hz), 1.41 (9H, s), 2.10 (1H, d, J=17 Hz), 2.15-2.23 (1H, m), 2.42 (3H, s), 2.63-2.69 (2H, m), 2.97 (1H, t, J=10 Hz), 3.01 (1H, d, J=17 Hz), 3.68 (1H, d, J=9 Hz), 4.00 (2H, s), 7.09-7.26 (3H, m).

Example 6b tert-Butyl 2-[(3R*,4S*)-1-[(2-chloro-6-methylphenyl)methyl]-3-{[1-(cyclohex-1-en-1-ylmethyl)piperidin-4-yl]carbamoyl}-4-methylpyrrolidin-3-yl]acetate The title compound (212 mg, yield 94.2%) was obtained from (3R*,4S*)-3-[2-(tert-butoxy)-2-oxoethyl]-1-[(2-chloro-6-methylphenyl)methyl]-4-methylpyrrolidine-3-carboxylic acid obtained in Example 6a (154 mg, 0.403 mmol) and 1-(cyclohex-1-en-1-ylmethyl)piperidin-4-amine obtained in Example 4b (110 mg, 0.564 mmol) by a method similar to the method described in Example 1k.

$^1$H-NMR (400 MHz, CDCl$_3$) δ ppm; 0.92 (3H, d, J=7 Hz), 1.21-1.39 (3H, m), 1.40 (9H, s), 1.52-1.69 (5H, m), 1.81-2.12 (8H, m), 1.99 (1H, d, J=16 Hz), 2.44 (3H, s), 2.52 (1H, d, J=10 Hz), 2.61 (1H, dd, J=6, 9 Hz), 2.68 (2H, br d, J=9 Hz), 2.75 (2H, s), 2.86 (1H, t, J=10 Hz), 3.10 (1H, d, J=16 Hz), 3.58 (1H, d, J=10 Hz), 3.60-3.70 (1H, m), 3.79 (1H, d, J=13 Hz), 3.84 (1H, d, J=13 Hz), 5.54 (1H, s), 7.08-7.14 (2H, m), 7.23-7.26 (1H, m), 8.00 (1H, d, J=8 Hz).

Example 6c

2-[(3R*,4S*)-1-[(2-Chloro-6-methylphenyl)methyl]-3-{[1-(cyclohex-1-en-1-ylmethyl)piperidin-4-yl]carbamoyl}-4-methylpyrrolidin-3-yl]acetic acid The title compound (140 mg, yield 73.4%) was obtained from tert-butyl 2-[(3R*,4S*)-1-[(2-chloro-6-methylphenyl)methyl]-3-{[1-(cyclohex-1-en-1-ylmethyl)piperidin-4-yl]carbamoyl}-4-methylpyrrolidin-3-yl]acetate obtained in Example 6b (212 mg, 0.38 mmol) by a method similar to the method described in Example 1m.

$^1$H-NMR (400 MHz, CD$_3$OD) δ ppm; 0.93 (3H, d, J=7 Hz), 1.57-1.80 (6H, m), 1.90-2.39 (8H, m), 2.49 (3H, s), 2.61-3.38 (8H, m), 3.59-4.20 (4H, m), 5.95 (1H, s), 7.18-7.39 (3H, m).

Example 7

2-[(3R*,4S*)-1-{[2-Chloro-6-(trifluoromethyl)phenyl]methyl}-3-{[1-(cyclopent-1-en-1-ylmethyl)piperidin-4-yl]carbamoyl}-4-methylpyrrolidin-3-yl]acetic acid

Example 7a

Cyclopent-1-ene-1-carbaldehyde

A mixture of sodium periodate (28.6 g, 134 mmol) and water (250 ml) was added to a mixture of 1,2-cyclohexanediol (12 g, 103 mmol) and diethyl ether (150 ml), which was stirred at mom temperature for 35 minutes. A 20% aqueous potassium hydroxide solution (40 ml, 206 mmol) was added to the reaction mixture, which was stirred at mom temperature for two hours. The reaction mixture was extracted with diethyl ether twice. The organic layer was dried over anhydrous magnesium sulfate, and the solvent was distilled off to give the title compound (6.1 g, yield 61.6%).

$^1$H-NMR (400 MHz, CDCl$_3$) δ ppm; 1.96-2.04 (2H, m), 2.50-2.57 (2H, m), 2.58-2.66 (2H, m), 6.87-6.90 (1H, m), 9.80 (1H, s).

Example 7b

2-[(3R*,4S*)-1-{[2-Chloro-6-(trifluoromethyl)phenyl]methyl}-3-{[1-(cyclopent-1-en-1-ylmethyl)piperidin-4-yl]carbamoyl}-4-methylpyrrolidin-3-yl]acetic acid The title compound (288 mg, yield: 73.5%) was obtained from 2-[(3R*,4S*)-1-{[2-chloro-6-(trifluoromethyl)phenyl]methyl}-4-methyl-3-[(piperidin-4-yl)carbamoyl]pyrrolidin-3-yl]acetic acid obtained in Example 3d (334 mg, 0.723 mmol), cyclopent-1-ene-1-carbaldehyde obtained in Example 7a (209 mg, 2.17 mmol), acetic acid (300 μl) and sodium triacetoxyborohydride (460 mg, 2.17 mmol) by a method similar to the method described in Example 3e.

$^1$H-NMR (400 MHz, CD$_3$OD) δ ppm; 0.89 (3H, d, J=7 Hz), 1.24-1.35 (2H, m), 1.50-1.66 (2H, m), 1.70-1.78 (1H, m), 1.85-1.99 (3H, m), 2.11-2.22 (2H, m), 2.29-2.42 (4H, m), 2.61 (1H, d, J=10 Hz), 2.60-2.68 (1H, m), 2.91-3.02 (2H, m), 3.07 (1H, d, J=16 Hz), 3.54 (1H, d, J=10 Hz), 3.64-3.78 (1H, m), 3.95 (1H, d, J=14 Hz), 4.05 (1H, d, J=14 Hz), 5.74 (1H, s), 7.50 (1H, t, J=8 Hz), 7.71 (1H, d, J=8 Hz), 7.78 (1H, d, J=8 Hz).

MS (ESI) m/z: 564.3 (M+Na)$^+$

Example 8

2-[(3R*,4S*)-1-[(2-Chloro-6-methylphenyl)methyl]-3-{[(1-cyclopent-1-en-1-ylmethyl)piperidin-4-yl]carbamoyl}-4-methylpyrrolidin-3-yl]acetic acid

Example 8a tert-Butyl 4-[(3R*,4S*)-3-[(2-tert-butoxy)-2-oxoethyl]-1-[(2-chloro-6-methylphenyl)methyl]-4-methylpyrrolidin-3-amido}piperidine-1-carboxylate The title compound (237 mg, yield 91.7%) was obtained from (3R*,4S*)-3-[(2-tert-butoxy)-2-oxoethyl]-1-[2-chloro-6-methylphenyl)methyl]-4-methylpyrrolidine-3-carboxylic acid obtained by a method similar to the method described in Example 6a (175 mg, 0.458 mmol) and tert-butyl 4-aminopiperidine-1-carboxylate (137 mg, 0.684 mmol) by a method similar to the method described in Example 1k.

$^1$H-NMR (400 MHz, CDCl$_3$) δ ppm; 0.92 (3H, d, J=8 Hz), 1.15-1.30 (2H, m), 1.40 (9H, s), 1.49 (9H, s), 1.58-1.68 (2H, m), 1.78-1.88 (1H, br), 1.99 (1H, d, J=8 Hz), 2.05-2.11 (1H, m), 2.42 (3H, s), 2.50 (1H, d, J=10 Hz), 2.60-2.66 (1H, m), 2.70-2.81 (2H, br), 2.85 (1H, t, J=10 Hz), 3.10 (1H, d, J=16 Hz), 3.55 (1H, d, J=10 Hz), 3.74-4.10 (4H, m), 7.07-7.15 (2H, m), 7.22-7.27 (1H, m), 8.14 (1H, d, J=8 Hz).

Example 8b

2-[(3R*,4S*)-1-[(2-Chloro-6-methylphenyl)methyl]-3-{[(1-cyclopent-1-en-1-ylmethyl)piperidin-4-yl]carbamoyl}-4-methylpyrrolidin-3-yl]acetic acid A mixture of tert-butyl 4-[(3R*,4S*)-3-[(2-tert-butoxy)-2-oxoethyl]-1-[(2-chloro-6-methylphenyl)methyl]-4-methylpyrrolidin-3-amido}piperidine-1-carboxylate obtained in Example 8a (237 mg, 0.42 mmol), trifluoroacetic acid (2.3 ml, 31 mmol) and dichloromethane (dehydrated) (2.3 ml) was stirred at mom temperature for three hours and 30 minutes. The reaction mixture was concentrated, and cyclopent-1-ene-1-carbaldehyde obtained in Example 7a (121 mg, 1.26 mmol), triethylamine (0.176 ml, 1.26 mmol) and tetrahydrofuran (5 ml) were added to the resulting residue, followed by stirring for 35 minutes. Sodium triacetoxyborohydride (267 mg, 1.26 mmol) was added to the reaction mixture, which was stirred at room temperature for 13 hours. The reaction mixture was concentrated, and the resulting residue was purified by silica gel column chromatography (ODS silica gel, elution solvent: water/methanol) twice to give the title compound (88 mg, yield 42.9%).

$^1$H-NMR (400 MHz, CD$_3$OD) δ ppm; 0.92 (3H, d, J=7 Hz), 1.50-1.68 (2H, br), 1.74-1.83 (1H, br), 1.88-2.00 (3H, m), 2.19-2.30 (2H, m), 2.31-2.43 (6H, m), 2.48 (3H, s), 2.62-2.72 (2H, m), 2.90-3.09 (4H, m), 3.25-3.40 (2H, m), 3.61 (1H, d, J=10 Hz), 3.66-3.78 (1H, m), 3.89-4.06 (2H, m), 5.73 (1H, s), 7.14-7.20 (2H, m), 7.25-7.30 (1H, m).

Example 9

2-[(3R*,4S*)-3-{[(3S)-1-(Cyclohex-1-en-1-ylmethyl)pyrrolidin-3-yl]carbamoyl}-1-[(2,6-dichlorophenyl)methyl]-4-methylpyrrolidin-3-yl]acetic acid

Example 9a tert-Butyl N-[(3S)-1-(cyclohex-1-en-1-ylmethyl)pyrrolidin-3-yl]carbamate 1-Cyclohexene-1-carboxaldehyde (1.48 ml, 13 mmol) was added to a mixture of (3S)-(−)-3-(tert-butoxycarbonylamino) pyrrolidine (2.0 g, 10.8 mmol), acetic acid (1.24 ml, 21.6 mmol) and tetrahydrofuran (dehydrated) (27 ml), followed by stirring at mom temperature for 15 minutes, and sodium triacetoxyborohydride (4.58 g, 21.6 mmol) was then added and the reaction mixture was stirred at mom temperature for 17 hours and 45 minutes. A saturated aqueous sodium bicarbonate solution was added to the reaction mixture, which was extracted with ethyl acetate. The organic layer was dried over sodium sulfate, and the solvent was distilled off. The residue was purified by NH silica gel column chromatography (elution solvent: ethyl acetate/heptane) to give the title compound (1.3 g, yield: 42.9%).

$^1$H-NMR (400 MHz, CDCl$_3$) δ ppm; 1.44 (9H, s), 1.50-1.65 (5H, m), 1.95-2.03 (4H, br), 2.17-2.29 (2H, m), 2.40-2.55 (2H, m), 2.65-2.74 (1H, m), 2.84-2.94 (2H, m), 4.10-4.19 (1H, br), 4.77-4.87 (1H, br), 5.56 (1H, br s).

Example 9b (3S)-1-(Cyclohex-1-en-1-ylmethyl)pyrrolidin-3-amine

A mixture of tert-butyl N-[(3S)-1-(cyclohex-1-en-1-ylmethyl)pyrrolidin-3-yl]carbamate obtained in Example 9a (1.3 g, 4.64 mmol) and ethanol (9.2 ml) was stirred under ice-cooling, a 5 N aqueous hydrochloric acid solution (9.28 ml, 46.4 mmol) was added, and the reaction mixture was stirred at room temperature for 14 hours and 30 minutes. The reaction mixture was stirred under ice-cooling, a 5 N aqueous sodium hydroxide solution (9.28 ml, 46.4 mmol) was added, and the solvent was distilled off. Ethanol was added to the residue, the precipitated solid was filtered off, and the solvent in the filtrate was distilled off. Ethanol was further added to the residue, the precipitated solid was filtered off, and the solvent in the filtrate was distilled off to give the title compound (0.8 g, yield 95.6%).

$^1$H-NMR (400 MHz, CD$_3$OD) δ ppm; 1.50-1.68 (6H, m), 1.90-2.05 (3H, m), 2.14-2.23 (1H, m), 2.28-2.32 (1H, m), 2.43-2.49 (1H, m), 2.63-2.73 (2H, m), 2.91-2.98 (2H, m), 3.44-3.50 (1H, m), 5.62 (1H, br s).

Example 9c tert-Butyl 2-[(3S,4R)-3-{[(3S)-1-(Cyclohex-1-en-1-ylmethyl)pyrrolidin-3-yl]carbamoyl}-1-[(2,6-dichlorophenyl)methyl]-4-methylpyrrolidin-3-yl]acetate The title compound (236 mg, yield 58%) was obtained from (3S)-1-(cyclohex-1-en-1-ylmethyl)pyrrolidin-3-amine obtained in Example 9b (169 mg, 0.94 mmol) and (3R*,4S*)-3-[2-(tert-butoxy)-2-oxoethyl]-1-[(2,6-dichlorophenyl)methyl]-4-methylpyrrolidine-3-carboxylic acid obtained in Example 2k (290 mg, 0.72 mmol) by a method similar to the method described in Example 1k.

$^1$H-NMR (400 MHz, CDCl$_3$) δ ppm; 0.91 (3H, d, J=7 Hz), 1.41 (9H, s), 1.50-1.63 (6H, m), 1.87-2.14 (6H, m), 2.20-2.25 (1H, m), 2.33-2.40 (1H, m), 2.51-2.67 (4H, m), 2.79-2.94 (3H, m), 3.11 (1H, d, J=16 Hz), 3.62 (1H, d, J=10 Hz), 3.92-4.02 (2H, m), 4.28-4.38 (1H, m), 5.74 (1H, br s), 7.17 (1H, dd, J=7, 8 Hz), 7.32 (2H, d, J=8 Hz), 8.30 (1H, d, J=7 Hz).

Example 9d

2-[(3R*,4S*)-3-{[(3S)-1-(Cyclohex-1-en-1-ylmethyl)pyrrolidin-3-yl]carbamoyl}-1-[(2,6-dichlorophenyl)methyl]-4-methylpyrrolidin-3-yl]acetic acid The title compound (173 mg, yield 81%) was obtained from tert-butyl 2-[(3R*,4S*)-3-{[(3S)-1-(cyclohex-1-en-1-ylmethyl)pyrrolidin-3-yl]carbamoyl}-1-[(2,6-dichlorophenyl)methyl]-4-methylpyrrolidin-3-yl]acetate obtained in Example 9c (236 mg, 0.42 mmol) by a method similar to the method described in Example 1m.

$^1$H-NMR (400 MHz, CD$_3$OD) δ ppm; 0.89 (3H, d, J=7 Hz), 1.55-1.67 (4H, m), 1.73-1.84 (1H, m), 1.92-2.32 (7H, m), 2.58-2.68 (2H, m), 2.74-2.85 (2H, m), 2.96-3.15 (4H, m), 3.20-3.34 (2H, m), 3.61 (1H, d, J=10 Hz), 4.00-4.08 (2H, m), 4.18-4.27 (1H, m), 5.74 (1H, br s), 7.29 (1H, dd, J=7, 9 Hz), 7.40-7.44 (2H, m).

Example 10

2-[(3R*,4S*)-1-{[2-Chloro-6-(difluoromethyl)phenyl]methyl}-3-[(1-hexylpiperidin-4-yl)carbamoyl]-4-methylpyrrolidin-3-yl]acetic acid Example 10a 1-Hexylpiperidin-4-amine The title compound was obtained by a method similar to the method described in US2005/0222175 A1 and Examples 4a and 4b.

$^1$H-NMR (400 MHz, CDCl$_3$) δ ppm: 0.80 (3H, t, J=7 Hz), 1.05-1.45 (12H, m), 1.73 (2H, d, J=6 Hz), 1.88 (2H, t, J=6 Hz), 2.21 (2H, dd, J=6, 8 Hz), 2.52-2.62 (1H, m), 2.79 (2H, d, J=12 Hz)

Example 10b

Methyl 3-chloro-2-methylbenzoate

Iodomethane (1.96 ml, 31.5 mmol) was added to a mixture of 3-chloro-2-methylbenzoic acid (3.58 g, 21 mmol), potassium carbonate (5.8 g, 42 mmol) and N,N-dimethylformamide (35.9 ml), followed by stirring at mom temperature for 18 hours and 30 minutes. Water and ethyl acetate were added to the reaction liquid, and the organic layer was extracted. The organic layer was sequentially washed with a saturated aqueous ammonium chloride solution and brine, and then dried over sodium sulfate, filtered and concentrated. The residue was purified by silica gel column chromatography (elution solvent: heptane/ethyl acetate) to give the title compound (3.67 g, yield: 97%).

$^1$H-NMR (400 MHz, CDCl$_3$) δ ppm: 2.60 (3H, s), 3.91 (3H, s), 7.13-7.21 (1H, m), 7.50 (1H, dd, J=1, 8 Hz), 7.70 (1H, dd, J=1, 8 Hz).

Example 10c

Methyl 2-(bromomethyl)-3-chlorobenzoate

A suspension of methyl 3-chloro-2-methylbenzoate obtained in Example 10b (1 g, 5.42 mmol), carbon tetrachloride (13.3 ml), N-bromosuccinimide (1.06 g, 5.96 mmol) and benzoyl peroxide (3.5 mg, 0.0108 mmol) was heated in a 90° C. oil bath under a nitrogen stream. After three hours and 45 minutes, heating was completed, and the mixture was diluted with water, ethyl acetate and a saturated aqueous sodium bicarbonate solution. The organic layer was washed with a saturated aqueous sodium bicarbonate solution, dried over anhydrous magnesium sulfate, filtered and concentrated to give the title compound (1.43 g, yield: 100%).

$^1$H-NMR (400 MHz, CDCl$_3$) δ ppm; 4.00 (3H, s), 5.12 (2H, s), 7.32 (1H, t, J=8 Hz), 7.58 (1H, dd, J=2, 8 Hz), 7.86 (1H, dd, J=2, 8 Hz).

Example 10d

[2-(Bromomethyl)-3-chlorophenyl]methanol

Dichloromethane (10 ml) was added to methyl 2-(bromomethyl)-3-chlorobenzoate obtained in Example 10c (500 mg, 1.9 mmol), a 1.04 M diisobutylaluminum hydride/n-hexane solution (4.57 ml, 4.75 mmol) was added at −78° C., followed by stirring for one hour under a nitrogen atmosphere. A saturated aqueous Rochelle salt solution and tert-butyl methyl ether were added, followed by extraction with tert-butyl methyl ether. The organic layer was washed with brine, dried over magnesium sulfate and then allowed to pass through a silica gel pad. The eluate was concentrated to give the title compound (440 mg, yield 98.3%).

$^1$H-NMR (400 MHz, CDCl$_3$) δ ppm; 1.82 (1H, t, J=6 Hz), 4.78 (2H, s), 4.85 (2H, d, J=5 Hz), 7.25-7.28 (1H, m), 7.31-7.40 (2H, m).

Example 10e 2-(Bromomethyl)-3-chlorobenzaldehyde

Dichloromethane (15 ml) and manganese dioxide (1.69 g, 19.4 mmol) were added to [2-(bromomethyl)-3-chlorophenyl]methanol obtained in Example 10d (440 mg, 1.87 mmol), followed by stirring at mom temperature overnight. Manganese dioxide (1.2 g, 13.8 mmol) was further added, followed by heating with stirring at 40° C. for 2.5 hours. The reaction mixture was filtered through Celite and washed with ethyl acetate. The filtrate was concentrated under reduced pressure, and the resulting crude product was purified by column chromatography (silica gel, elution solvent: heptane/ethyl acetate=99/1->90/10) to give the title compound (289 mg, yield 66.2%).

$^1$H-NMR (400 MHz, CDCl$_3$) δ ppm; 5.13 (2H, s), 7.48 (1H, t, J=8 Hz), 7.66 (1H, dd, J=1, 8 Hz), 7.77 (1H, dd, J=1, 8 Hz), 10.23 (1H, s).

Example 10f 2-(Bromomethyl)-1-chloro-3-(difluoromethyl)benzene

Dichloromethane (10 ml) was added to 2-(bromomethyl)-3-chlorobenzaldehyde obtained in Example 10e (289 mg, 1.24 mmol), [bis(2-methoxyethyl)amino]sulfur trifluoride (457 μl, 2.48 mmol) was added at 0° C., followed by stirring at mom temperature for 1.5 hours under a nitrogen atmosphere. A saturated aqueous sodium bicarbonate solution was added at 0° C. to the reaction mixture, which was extracted with diethyl ether. The organic layer was washed with brine, dried over magnesium sulfate and then concentrated. The resulting crude product was purified by column chromatography (silica gel, elution solvent: heptane/ethyl acetate=99/1->95/5) to give the title compound (238.3 mg, yield 75.2%).

$^1$H-NMR (400 MHz, CDCl$_3$) δ ppm; 4.74 (2H, s), 6.93 (1H, t, J=55 Hz), 7.37 (1H, t, J=8 Hz), 7.53 (2H, t, J=8 Hz).

Example 10g (3RS,4SR)-3-[2-(tert-Butoxy)-2-oxoethyl]-1-[(2,6-dichlorophenyl)methyl]-4-methylpyrrolidine-3-carboxylic acid 20% palladium hydroxide (500 mg) was added to a solution of benzyl (3RS,4SR)-1-benzyl-3-[2-(tert-butoxy)-2-oxoethyl]-4-methylpyrrolidine-3-carboxylate obtained by a method similar to that of Example 1g (8.35 g, 19.7 mmol) in methanol (200 ml), followed by stirring at mom temperature overnight under a hydrogen atmosphere. The reaction mixture was filtered, and palladium on the filter paper was washed well with hot water at 50° C. The filtrate was concentrated and azeotropically distilled with methanol and toluene well to give a white solid (3.92 g). Methanol (20 ml), 2,6-dichlorobenzaldehyde (5.64 g, 32.2 mmol), acetic acid (966 µl, 16.1 mmol) and sodium triacetoxyborohydride (6.82 g, 32.2 mmol) were added thereto, followed by stirring at mom temperature overnight. The reaction mixture was further heated with stirring in a 50° C. hot water bath for three hours. Neutral buffer [prepared from potassium dihydrogenphosphate (13.65 g), disodium hydrogenphosphate dodecahydrate (71.6 g) and water (1.5 L)] and ethyl acetate were added to the reaction mixture, and the solid was filtered off. The solid on the filter paper was washed with ethyl acetate to give the title compound as a white solid. The filtrate was extracted with ethyl acetate, and the organic layer was then dried over sodium sulfate, concentrated, purified by column chromatography (silica gel, elution solvent: methanol/ethyl acetate) and combined with the solid on the filter paper to give the title compound (3.77 g, yield 58.2%).

$^1$H-NMR (400 MHz, CDCl$_3$) δ ppm; 1.01 (3H, d, J=7 Hz), 1.42 (9H, s), 2.09 (1H, d, J=16 Hz), 2.14-2.24 (1H, m), 2.62-2.69 (2H, m), 2.99 (1H, t, J=10 Hz), 3.02 (1H, d, J=10 Hz), 3.71 (1H, d, J=10 Hz), 4.08 (1H, d, J=12 Hz), 4.12 (1H, d, J=12 Hz), 7.21 (1H, d, J=8 Hz), 7.23 (1H, d, J=8 Hz), 7.37 (1H, d, J=8 Hz).

Example 10h tert-Butyl 2-[(3R*,4S*)-1-[(2,6-dichlorophenyl)methyl]-3-[(1-hexylpiperidin-4-yl)carbamoyl]-4-methylpyrrolidin-3-yl]acetate 1-Hexylpiperidin-4-amine obtained in Example 10a (894 mg, 4.85 mmol), triethylamine (1.04 ml, 7.46 mmol), N,N-dimethylformamide (10 ml) and PyBOP (2.52 g, 4.85 mmol) were added to (3RS,4SR)-3-[2-(tert-butoxy)-2-oxoethyl]-1-[(2,6-dichlorophenyl)methyl]-4-methylpyrrolidine-3-carboxylic acid obtained in Example 10g (1.5 g, 3.73 mmol), followed by stirring at room temperature overnight. Water was added to the reaction mixture, which was extracted with ethyl acetate. The organic layer was washed with water and brine and dried over sodium sulfate. This was concentrated, and the crude product was purified by column chromatography (NH silica gel, elution solvent: ethyl acetate/heptane) to give a white solid (1.85 g). This was optically resolved by HPLC (CHIRALPAK IA (3 cm diameter×25 cm), elution solvent: ethanol/hexane=6/94, flow rate: 20 ml/min.) to give a chiral form corresponding to the peak with a shorter retention time (875 mg).
Analysis by HPLC;
(Analysis conditions) Column: CHIRALPAK IA (manufactured by Daicel Chemical Industries, Ltd.) (0.46 cm diameter×15 cm), 40° C., eluent: hexane/ethanol=9/1 (v/v), flow rate: 1 ml/min., detection: UV (210 nm)
(Analysis result) The resulting chiral form was analyzed under the above analysis conditions to find that the retention time was 4.85 minutes and the enantiomeric excess was >99% ee.

Example 10i tert-Butyl 2-[(3R*,4S*)-3-[(1-hexylpiperidin-4-yl)carbamoyl]-4-methylpyrrolidin-3-yl]acetate Methanol (10 ml) and 20% palladium hydroxide (50 mg) were added to 250 mg of tert-butyl 2-[(3R*,4S*)-1-[(2,6-dichlorophenyl)methyl]-3-[(1-hexylpiperidin-4-yl)carbamoyl]-4-methylpyrrolidin-3-yl]acetate obtained in Example 10h, followed by stirring at room temperature for two hours under a hydrogen atmosphere. The reaction mixture was filtered, and the filtrate was concentrated to give the title compound (180 mg).

$^1$H-NMR (400 MHz, CDCl$_3$) δ ppm; 0.85-0.90 (3H, m), 1.04 (3H, d, J=6 Hz), 1.25-1.35 (5H, m), 1.42 (9H, s), 1.78-2.10 (6H, m), 2.26-2.50 (4H, m), 2.88-3.05 (3H, m), 3.23 (1H, d, J=13 Hz), 3.29-3.54 (5H, m), 3.55-3.67 (1H, m), 4.17 (1H, d, J=13 Hz), 4.27-4.40 (1H, br), 7.82-7.92 (1H, br).

Example 10j tert-Butyl 2-[(3R*,4S*)-1-{[2-chloro-6-(difluoromethyl)phenyl]methyl}-3-[(1-hexylpiperidin-4-yl)carbamoyl]-4-methylpyrrolidin-3-yl]acetate N,N-Dimethylformamide (400 µl), 2-(bromomethyl)-1-chloro-3-(difluoromethyl)benzene obtained in Example 10f (24.9 mg, 0.0976 mmol) and potassium carbonate (20.2 mg, 0.146 mmol) were added to tert-butyl 2-[(3R*,4S*)-3-[(1-hexylpiperidin-4-yl)carbamoyl]-4-methylpyrrolidin-3-yl]acetate obtained in Example 10i (20 mg, 0.0488 mmol), followed by stirring at room temperature overnight. Ethyl acetate and water were added to the reaction mixture, which was extracted with ethyl acetate. The organic layer was washed with brine and dried over magnesium sulfate. This was concentrated, and the resulting crude product was purified by column chromatography (NH silica gel, elution solvent: heptane/ethyl acetate=98/2->80/20) to give the title compound (14.4 mg, yield 50.2%).

$^1$H-NMR (400 MHz, CDCl$_3$) δ ppm; 0.87-0.94 (6H, m), 1.22-1.35 (6H, m), 1.40 (9H, s), 1.40-1.49 (2H, m), 1.68-1.76 (1H, m), 1.77-2.12 (7H, m), 2.24-2.28 (2H, m), 2.54 (1H, d, J=10 Hz), 2.59-2.63 (1H, m), 2.74-2.88 (3H, m), 3.13 (1H, d, J=16 Hz), 3.61 (1H, d, J=10 Hz), 3.61-3.72 (1H, m), 3.91 (1H, d, J=13 Hz), 3.95 (1H, d, J=13 Hz), 6.96 (1H, t, J=55 Hz), 7.35 (1H, t, J=8 Hz), 7.54 (2H, d, J=8 Hz), 7.65 (1H, d, J=8 Hz).

Example 10k

2-[(3R*,4S*)-1-{[2-Chloro-6-(difluoromethyl)phenyl]methyl}-3-[(1-hexylpiperidin-4-yl)carbamoyl]-4-methylpyrrolidin-3-yl]acetic acid The title compound (13.9 mg, yield 61.5%) was obtained from tert-butyl 2-[(3R*,4S*)-1-{[2-chloro-6-(difluoromethyl)phenyl]methyl}-3-[(1-hexylpiperidin-4-yl)carbamoyl]-4-methylpyrrolidin-3-yl]acetate obtained by a method similar to that of Example 10j (25 mg, 0.0428 mmol) by a method similar to the method described in Example 1m.

$^1$H-NMR (400 MHz, CDCl$_3$) δ ppm; 0.82-0.90 (3H, m), 0.93 (3H, d, J=7 Hz), 1.23-1.34 (6H, m), 1.52-1.64 (2H, m), 1.76-1.98 (4H, m), 2.22-2.44 (4H, m), 2.50-2.78 (5H, m), 2.91 (1H, t, J=8 Hz), 3.22-3.35 (1H, br), 3.36-3.43 (1H, m), 3.70-3.82 (1H, m), 3.92 (1H, d, J=14 Hz), 3.96 (1H, d, J=14 Hz), 7.21 (1H, t, J=55 Hz), 7.30 (1H, t, J=8 Hz), 7.48 (1H, d, J=8 Hz), 7.55 (1H, d, J=8 Hz), 8.92-9.08 (1H, br).

Example 11

2-[(3R*,4S*)-3-{[(1-Cyclohex-1-en-1-ylmethyl)piperidin-4-yl]carbamoyl}-1-[(2,6-dichlorophenyl)methyl]-4-methylpyrrolidin-3-yl]acetic acid Example 11a (3R*,4S*)-3-[2-(tert-Butoxy)-2-oxoethyl]-1-[(2,6-dichlorophenyl)methyl]-4-methylpyrrolidine-3-carboxylic acid Methanol (3 ml), 2,6-dichlorobenzaldehyde (431 mg, 2.46 mmol), acetic acid (73.8 µl, 1.23 mmol) and sodium triacetoxyborohydride (521 mg, 2.46 mmol) were added to (3R*,4S*)-3-[2-(tert-butoxy)-2-oxoethyl]-4-methylpyrrolidine-3-carboxylic acid obtained by a method similar to that of Example 11 (300 mg, 1.23 mmol), followed by stirring at room temperature for two days. Water was added to the system, which was extracted with ethyl acetate, and the organic layer was dried over sodium sulfate and concentrated. The resulting crude product was purified by column chromatography (silica gel, elution solvent: methanol/ethyl acetate) to give the title compound (180 mg). On the other hand, the aqueous layer upon partitioning was concentrated and purified by ODS column chromatography (elution solvent, methanol/water) to recover (3R*,4S*)-3-[2-(tert-butoxy)-2-oxoethyl]-4-methylpyrrolidine-3-carboxylic acid (120 mg). The title compound (42.7 mg) was obtained by performing similar reaction again using the recovered raw material, and was combined with the first title compound (180 mg).

$^1$H-NMR (400 MHz, CDCl$_3$) was confirmed to be identical to that of the compound obtained in Example 10g.

Example 11b tert-Butyl 2-[(3R*,4S*)-{3-[(1-cyclohex-1-en-1-ylmethyl)piperidin-4-yl]carbamoyl}-1-[(2,6-dichlorophenyl)methyl]-4-methylpyrrolidin-3-yl]acetate The title compound (274 mg, yield 85.8%) was obtained from (3R*,4S*)-3-[2-(tert-butoxy)-2-oxoethyl]-1-[(2,6-dichlorophenyl)methyl]-4-methylpyrrolidine-3-carboxylic acid obtained in Example 11a (222 mg, 0.55 mmol) and 1-(cyclohex-1-en-1-ylmethyl)piperidin-4-amine obtained in Example 4b (150 mg, 0.772 mmol) by a method similar to the method described in Example 1k.

$^1$H-NMR (400 MHz, CDCl$_3$) δ ppm; 0.91 (3H, d, J=8 Hz), 1.31-1.50 (2H, m), 1.42 (9H, s), 1.52-1.72 (5H, m), 1.81-2.12 (9H, m), 2.55-2.70 (4H, m), 2.75 (2H, s), 2.92 (1H, t, J=10 Hz), 3.12 (1H, d, J=16 Hz), 3.60-3.72 (2H, m), 3.96 (2H, s), 5.54 (1H, s), 7.18 (1H, t, J=8 Hz), 7.33 (2H, d, J=8 Hz), 8.09 (1H, d, J=8 Hz).

Example 11c

2-[(3R*,4S*)-3-{[(1-Cyclohex-1-en-1-ylmethyl)piperidin-4-yl]carbamoyl}-1-[(2,6-dichlorophenyl)methyl]-4-methylpyrrolidin-3-yl]acetic acid The title compound (169 mg, yield 68.2%) was obtained from tert-butyl 2-[(3R*,4S*)-{3-[(1-cyclohex-1-en-1-ylmethyl)piperidin-4-yl]carbamoyl}-1-[(2,6-dichlorophenyl)methyl]-4-methylpyrrolidin-3-yl]acetate obtained in Example 11b (274 mg, 0.474 mmol) by a method similar to the method described in Example 1m.

$^1$H-NMR (400 MHz, CD$_3$OD) δ ppm; 0.89 (3H, d, J=7 Hz), 1.56-1.75 (6H, m), 1.78-1.94 (2H, m), 2.00-2.26 (6H, m), 2.36-2.48 (2H, m), 2.60-2.64 (1H, m), 2.68 (1H, d, J=10 Hz), 2.95-3.19 (6H, m), 3.62 (1H, d, J=10 Hz), 3.68-3.80 (1H, br), 3.99-4.07 (2H, m), 5.76 (1H, s), 7.29 (1H, t, J=8 Hz), 7.43 (2H, d, J=8 Hz).

Example 12

2-[(3R*,4S*)-1-{[2-Chloro-6-(difluoromethyl)phenyl]methyl}-3-{[1-(cyclohex-1-en-1-ylmethyl)piperidin-4-yl]carbamoyl}-4-methylpyrrolidin-3-yl]acetic acid

Example 12a tert-Butyl 4-[(3R*,4S*)-3-[2-(tert-butoxy)-2-oxoethyl]-1-{[2-chloro-6-(difluoromethyl)phenyl]methyl}-4-methylpyrrolidin-3-amido]piperidine-1-carboxylate tert-Butyl 4-[(3R*,4S*)-3-[2-(tert-butoxy)-2-oxoethyl]-4-methylpyrrolidin-3-amido]piperidine-1-carboxylate obtained in Example 3b (375 mg, 0.881 mmol) was dissolved in N,N-dimethylformamide (7 ml). Potassium carbonate (304 mg, 2.2 mmol) and 2-(bromomethyl)-1-chloro-3-(difluoromethyl)benzene obtained by a method similar to that of Example 10f (450 mg, 1.76 mmol) were added thereto, and the mixture was heated in a 45° C. oil bath for two hours. The reaction mixture was partitioned between ethyl acetate and a saturated aqueous ammonium chloride solution. The separated organic layer was washed with a saturated aqueous ammonium chloride solution three times, dried over anhydrous magnesium sulfate, filtered and concentrated. The residue was purified by silica gel column chromatography (silica gel, elution solvent: heptane/ethyl acetate) to give the title compound (332 mg, yield: 62.8%).

$^1$H-NMR (400 MHz, CDCl$_3$) δ ppm; 0.92 (3H, d, J=7 Hz), 1.13-1.74 (3H, m), 1.39 (9H, s), 1.49 (9H, s), 1.75-1.87 (1H, m), 2.00 (1H, d, J=16 Hz), 2.04-2.15 (1H, m), 2.52 (1H, d, J=10 Hz), 2.56-2.83 (3H, m), 2.86 (1H, t, J=10 Hz), 3.12 (1H, d, J=10 Hz), 3.57 (1H, d, J=10 Hz), 3.80-4.16 (3H, m), 3.90 (1H, d, J=13 Hz), 3.96 (1H, d, J=13 Hz), 6.93 (1H, t, J=55 Hz), 7.37 (1H, t, J=8 Hz), 7.55 (2H, d, J=8 Hz), 7.77 (1H, d, J=8 Hz).

Example 12b

2-[(3R*,4S*)-1-{[2-Chloro-6-(difluoromethyl)phenyl]methyl}-3-{[1-(cyclohex-1-en-1-ylmethyl)piperidin-4-yl]carbamoyl}-4-methylpyrrolidin-3-yl]acetic acid tert-Butyl 4-[(3R*,4S*)-3-[2-(tert-butoxy)-2-oxoethyl]-1-{[2-chloro-6-(difluoromethyl)phenyl]methyl}-4-methylpyrrolidin-3-amido]piperidine-1-carboxylate obtained in Example 12a (332 mg, 0.553 mmol) was dissolved in dichloromethane (3.0 ml), trifluoroacetic acid (3.0 ml) was added thereto, and the mixture was then left to stand at mom temperature. After two hours and 30 minutes, the reaction liquid was concentrated and azeotropically distilled with dichloromethane twice to give an intermediate. 186 mg of the resulting intermediate (372 mg) was dissolved in tetrahydrofuran (5 ml), triethylamine (116 μl, 0.831 mmol) and cyclohex-1-ene-1-carbaldehyde (91.5 mg, 0.831 mmol) were added, and the mixture was left to stand at room temperature. After 30 minutes, sodium triacetoxyborohydride (176 mg, 0.831 mmol) was added thereto, and the mixture was stirred at mom temperature. After 10 hours and 50 minutes, the mixture was concentrated. The residue was purified by silica gel column chromatography (ODS, elution solvent: water/methanol) to give the title compound (80 mg).

$^1$H-NMR (400 MHz, CD$_3$OD) δ ppm; 0.90 (3H, d, J=7 Hz), 1.57-1.75 (6H, m), 1.83-1.96 (2H, m), 2.02-2.13 (4H, m), 2.15-2.27 (1H, m), 2.27 (1H, d, J=16 Hz), 2.46-2.65 (3H, m), 2.61 (1H, d, J=10 Hz), 2.95 (1H, t, J=9 Hz), 2.97 (1H, d, J=16 Hz), 3.03-3.16 (2H, m), 3.20-3.27 (2H, m), 3.50 (1H, d, J=10 Hz), 3.74-3.83 (1H, m), 3.98 (1H, d, J=13 Hz), 4.02 (1H, d, J=13 Hz), 5.78-5.86 (1H, br), 7.26 (1H, t, J=55 Hz), 7.42 (1H, t, J=8 Hz), 7.60 (2H, d, J=8 Hz).

Example 13

2-[(3R*,4S*)-1-{[2-Chloro-6-(difluoromethyl)phenyl]methyl}-3-{[1-(cyclopent-1-en-1-ylmethyl)piperidin-4-yl]carbamoyl}-4-methylpyrrolidin-3-yl] acetic acid The title compound (76 mg) was obtained by a method similar to the method described in Example 12b using the intermediate obtained in Example 12b (186 mg) and cyclopent-1-ene-1-carbaldehyde obtained in Example 7a (79.9 mg, 0.831 mmol).

$^1$H-NMR (400 MHz, CD$_3$OD) δ ppm; 0.90 (3H, d, J=7 Hz), 1.58-1.75 (2H, m), 1.80-2.00 (4H, m), 2.15-2.27 (1H, m), 2.47 (1H, d, J=16 Hz), 2.32-2.42 (4H, m), 2.46-2.65 (3H, m), 2.62 (1H, d, J=10 Hz), 2.95 (1H, t, J=9 Hz), 2.99 (1H, d, J=16 Hz), 3.03-3.16 (2H, m), 3.36-3.43 (2H, m), 3.51 (1H, d, J=10 Hz), 3.73-3.82 (1H, m), 3.98 (1H, d, J=13 Hz), 4.03 (1H, d, J=13 Hz), 5.78-5.83 (1H, br), 7.25 (1H, t, J=55 Hz), 7.43 (1H, t, J=8 Hz), 7.61 (2H, d, J=8 Hz).

Example 14

2-[(3R*,4S*)-1-{[2-Chloro-6-(difluoromethyl)phenyl]methyl}-3-{[1-(cyclohexylmethyl)piperidin-4-yl]carbamoyl}-4-methylpyrrolidin-3-yl]acetic acid

Example 14a 1-(Cyclohexylmethyl)piperidin-4-amine

The title compound was obtained by a method similar to the method described in US2005/0222175 A1 and Examples 4a and 4b.

$^1$H-NMR (400 MHz, CDCl$_3$) δ ppm: 0.77-0.87 (2H, m), 1.11-1.49 (8H, m), 1.61-1.80 (5H, m), 1.97 (2H, t, J=12 Hz), 2.14 (2H, d, J=7 Hz), 2.50-2.64 (1H, m), 2.96 (2H, d, J=12 Hz).

Example 14b tert-Butyl 2-[(3R*,4S*)-1-benzyl-3-{[1-(cyclohexylmethyl)piperidin-4-yl]carbamoyl}-4-methylpyrrolidin-3-yl]acetate The title compound (250 mg, yield: 81.4%) was obtained from (3R*,4S*)-1-benzyl-3-[2-(tert-butoxy)-2-oxoethyl]-4-methylpyrrolidine-3-carboxylic acid obtained in Example 1j (200 mg, 0.6 mmol) and 1-(cyclohexylmethyl)piperidine-4-amine obtained in Example 14a (141 mg, 0.72 mmol) by a method similar to the method described in Example 1k.

$^1$H-NMR (400 MHz, CDCl$_3$) δ ppm; 0.80-0.98 (2H, m), 0.92 (3H, d, J=7 Hz), 1.07-2.15 (17H, m), 1, 58 (9H, s), 1.95 (1H, d, J=16 Hz), 2.10 (1H, d, J=7 Hz), 2.36 (1H, d, J=10 Hz), 2.55-2.83 (4H, m), 3.08 (1H, d, J=16 Hz), 3.59 (1H, d, J=10 Hz), 3.63-3.77 (1H, m), 3.64 (1H, d, J=13 Hz), 3.69 (1H, d, J=13 Hz), 7.21-7.36 (5H, m), 8.56 (1H, d, J=8 Hz).

Example 14c tert-Butyl 2-[(3R*,4S*)-1-{[2-chloro-6-(difluoromethyl)phenyl]methyl}-3-{[1-(cyclohexylmethyl)piperidin-4-yl]carbamoyl}-4-methylpyrrolidin-3-yl] acetate The title compound (198 mg, yield: 67.9%) was obtained from tert-butyl 2-[(3R*,4S*)-1-benzyl-3-{[1-(cyclohexylmethyl)piperidin-4-yl]carbamoyl}-4-methylpyrrolidin-3-yl]acetate obtained in Example 14b (250 mg, 0.489 mmol) and 2-(bromomethyl)-1-chloro-3-(difluoromethyl)benzene obtained by a method similar to that of Example 10f (250 mg, 0.978 mmol) by a method similar to the method described in Example 11.

$^1$H-NMR (400 MHz, CDCl$_3$) δ ppm; 0.78-0.97 (2H, m), 0.91 (3H, d, J=7 Hz), 1.08-2.13 (18H, m), 1.40 (9H, s), 2.00 (1H, d, J=17 Hz), 2.05 (1H, d, J=7 Hz), 2.54 (1H, d, J=10 Hz), 2.61 (1H, dd, J=6, 10 Hz), 2.66-2.77 (2H, m), 2.85 (1H, t, J=10 Hz), 3.60 (1H, d, J=17 Hz), 3.58-3.72 (1H, m), 3.92 (1H, d, J=13 Hz), 3.96 (1H, d, J=13 Hz), 6.97 (1H, t, J=55 Hz), 7.36 (1H, t, J=8 Hz), 7.51-7.58 (2H, m), 7.62 (1H, d, J=8 Hz).

Example 14d

2-[(3R*,4S*)-1-{[2-Chloro-6-(difluoromethyl)phenyl]methyl}-3-{[1-(cyclohexylmethyl)piperidin-4-yl]carbamoyl}-4-methylpyrrolidin-3-yl]acetic acid The title compound (140 mg, yield: 79.8%) was obtained from tert-butyl 2-[(3R*,4S*)-1-{[2-chloro-6-(difluoromethyl)phenyl]methyl}-3-{[1-(cyclohexylmethyl)piperidin-4-yl]carbamoyl}-4-methylpyrrolidin-3-yl]acetate obtained in Example 14c (194 mg, 0.325 mmol) by a method similar to the method described in Example 1m.

$^1$H-NMR (400 MHz, CD$_3$OD) δ ppm; 0.90 (3H, d, J=7 Hz), 0.93-1.06 (2H, m), 1.16-1.40 (4H, m), 1.62-1.83 (8H, m), 1.85-1.98 (2H, m), 2.17-2.28 (1H, m), 2.29 (1H, d, J=16 Hz), 2.41-2.50 (1H, m), 2.56-2.80 (4H, m), 2.90-2.99 (2H, m), 3.10-3.25 (2H, m), 3.49 (1H, d, J=10 Hz), 3.76-3.86 (1H, m), 3.97 (1H, d, J=13 Hz), 4.01 (1H, d, J=13 Hz), 7.28 (1H, t, J=55 Hz), 7.42 (1H, t, J=8 Hz), 7.56-7.63 (2H, m).

Reference Example 1

1,3-Dibenzyl (3RS,4SR)-3-[2-(tert-butoxy)-2-oxoethyl]-4-methylpyrrolidine-1,3-dicarboxylate

Reference Example 1a (3RS,4SR)-3-[2-(tert-Butoxy)-2-oxoethyl]-4-methylpyrrolidine-3-carboxylic acid 44.7 g of (4-methoxyphenyl)methyl (3RS,4SR)-1-benzyl-3-[2-(tert-butoxy)-2-oxoethyl]-4-methylpyrrolidine-3-carboxylate was obtained by a method similar to the method described in Examples 2e to 2g. A part of this compound (20 g, 44.1 mmol) was dissolved in methanol (316 ml), 10% Pd/C (3.93 g) was added, and the atmosphere was replaced with hydrogen gas. The mixture was stirred at room temperature overnight and then stirred with addition of warm water (36° C., 160 ml) for 30 minutes, and the precipitated solid was dissolved. Pd/C was filtered off, the filtrate was then concentrated so that about 20 to 40 ml of water remained, and methanol (80 ml) was added to the cloudy residue containing water, which was stirred for 30 minutes. The precipitated solid was filtered off (Lot A). ¹H-NMR of Lot A is shown below.

Lot B was obtained by a similar method using (4-methoxyphenyl)methyl (3RS,4SR)-1-benzyl-3-[2-(tert-butoxy)-2-oxoethyl]-4-methylpyrrolidine-3-carboxylate (21 g, 46.3 mmol). After confirming that ¹H-NMR of Lot B is identical to ¹H-NMR of Lot A, Lot A and Lot B were combined and dried to give the title compound (9.91 g).

¹H-NMR (400 MHz, D$_2$O) δ ppm; 0.97 (3H, d, J=6 Hz), 1.42 (9H, s), 2.12-2.24 (1H, m), 2.29 (1H, d, J=17 Hz), 2.93 (1H, d, J=17 Hz), 3.04 (1H, t, J=12 Hz), 3.18 (1H, d, J=12 Hz), 3.49 (1H, dd, J=8, 12 Hz), 4.03 (1H, d, J=12 Hz).

Reference Example 1b (3RS,4SR)-1-[(Benzyloxy)carbonyl]-3-[2-(tert-butoxy)-2-oxoethyl]-4-methylpyrrolidine-3-carboxylic acid A 2 N aqueous sodium hydroxide solution (20.2 ml) was added to a mixture of (3RS,4SR)-3-[2-(tert-butoxy)-2-oxoethyl]-4-methylpyrrolidine-3-carboxylic acid obtained in Reference Example 1a (9.84 g, 40.5 mmol), acetone (39 ml) and water (49 ml) with stirring under ice-cooling (0 to 1° C.), and the reaction mixture was dissolved by stirring for 45 minutes. Benzyl chloroformate (6.35 ml, 44.5 mmol) and a 2 N aqueous sodium hydroxide solution (22.3 ml) were simultaneously added dropwise to the reaction mixture at an internal temperature of 3.5° C. or lower with stirring under ice-cooling (0 to 1° C.) over 20 minutes. The reaction liquid was stirred in an ice bath and gradually returned to mom temperature. This was stirred at mom temperature overnight. A 1N aqueous sodium hydroxide solution (10 ml) was added to the reaction liquid with stirring under ice-cooling (internal temperature: about 15° C.), and the mixture was adjusted to pH 12. This reaction liquid was returned to room temperature and washed three times by adding ethyl ether. The aqueous layer was adjusted to pH 2 to 3 by sequentially adding a 2 N aqueous hydrochloric acid solution (20.2 ml) and a 1N aqueous hydrochloric acid solution (13 ml) with stirring under ice-cooling (internal temperature: 5° C. or lower). The aqueous layer was returned to mom temperature and extracted with ethyl acetate three times. The organic layer was washed with brine, and then dried over sodium sulfate, filtered and concentrated. The residue was dissolved in ethyl acetate, washed with water four times and then with brine, dried over sodium sulfate, filtered and concentrated to give the title compound (14.53 g, yield: 95.1%).

¹H-NMR (400 MHz, CDCl$_3$) δ ppm; 1.02 (3H, t, J=8 Hz), 1.42 (9H, s), 2.14-2.22 (1H, m), 2.27 (1H, d, J=17 Hz), 3.04 (1H, d, J=5, 17 Hz), 3.12-3.19 (1H, m), 3.35 (1H, dd, J=7, 12 Hz), 3.65-3.72 (1H, m), 4.29 (1H, dd, J=7, 12 Hz), 5.09-5.19 (2H, m), 7.26-7.38 (5H, m).

Reference Example 1c 1,3-Dibenzyl (3RS,4SR)-3-[2-(tert-butoxy)-2-oxoethyl]-4-methylpyrrolidine-1,3-dicarboxylate Benzyl bromide (4.48 ml, 37.7 mmol) was added to a mixture of (3RS,4SR)-1-[(benzyloxy)carbonyl]-3-[2-(tert-butoxy)-2-oxoethyl]-4-methylpyrrolidine-3-carboxylic acid obtained in Reference Example 1b (14.5 g, 38.5 mmol), potassium carbonate (10.6 g, 77 mmol) and N,N-dimethylformamide (50 ml) with stirring under ice-cooling (internal temperature: 3 to 7° C.), and the mixture was stirred for one hour, returned to mom temperature and stirred overnight. Water was added to the reaction liquid, which was extracted with ethyl acetate three times. The organic layers were combined, sequentially washed with a saturated aqueous ammonium chloride solution (five times), water (twice) and brine, and then dried over sodium sulfate, filtered and concentrated to give the title compound (17.67 g, yield: 98.2%).

¹H-NMR (400 MHz, CDCl$_3$) δ ppm; 0.84-0.89 (3H, m), 1.36-1.39 (9H, m), 2.09-2.18 (1H, m), 2.24 (1H, dd, J=3, 17 Hz), 3.04-3.13 (2H, m), 3.35 (1H, dd, J=8, 12 Hz), 3.59-3.68 (1H, m), 4.32 (1H, t, J=12 Hz), 5.06-5.20 (4H, m), 7.29-7.36 (10H, m).

Reference Example 2

(3R*,4S*)-3-[2-(tert-Butoxy)-2-oxoethyl]-4-methylpyrrolidine-3-carboxylic acid

Reference Example 2a (−)-Dibenzoyl-L-tartrate of (4-methoxyphenyl)methyl (3S*,4S*)-1-benzyl-4-methylpyrrolidine-3-carboxylate (4-Methoxyphenyl)methyl (3RS,4RS)-1-benzyl-4-methylpyrrolidine-3-carboxylate separately obtained by a method similar to the method described in Example 2f (1000 mg, 2.946 mmol) was dissolved in methyl isobutyl ketone (4 ml), and (−)-dibenzoyl-L-tartaric acid (1055 mg) was added and dissolved. Crystals obtained from (4-methoxyphenyl)methyl (3RS,4RS)-1-benzyl-4-methylpyrrolidine-3-carboxylate separately obtained by a method similar to that of Example 2f and (−)-dibenzoyl-L-tartaric acid were added to the resulting solution as seed crystals, and the resulting precipitate was filtered off to give the title compound (757 mg, yield: 36.8%). Ethanol (3.02 mL) was added to 755 mg of the resulting solid, which was heated and dissolved, and then tert-butyl methyl ether (6.04 mL) was added. The resulting precipitate was filtered off to give the title compound (658 mg, yield: 87.2%) as crystals.

(4-Methoxyphenyl)methyl (3R*,4R*)-1-benzyl-4-methylpyrrolidine-3-carboxylate separately obtained by a method similar to the method described in Example 2f (150.0 g, 441 mmol) was dissolved in methyl isobutyl ketone (600 ml), and (−)-dibenzoyl-L-tartaric acid (157.0 g) was added and dissolved with stirring. (4-Methoxyphenyl)methyl (3RS,4RS)-1-benzyl-4-methylpyrrolidine-3-carboxylate (−)-dibenzoyl-L-tartrate obtained by the method described in the previous paragraph was added to the resulting solution as seed crystals (7.5 mg), followed by stirring for 18 hours and 18 minutes. The precipitated solid was filtered off and washed with methyl isobutyl ketone (150 ml). The resulting solid was dried under reduced pressure at 50° C. to give the title compound (152.07 g, yield: 49.4%). Ethanol (600 ml) was added to 150.00 g of the resulting solid, which was heated to 80° C. with stirring, and dissolution of the solid was confirmed, after which heating was stopped. Fifty-nine minutes after stopping heating, tert-butyl methyl ether (300 ml) was added over nine minutes; after further six minutes, seed crystals (5 mg) were added. After 12 minutes, tert-butyl methyl ether (900 ml) was added over two hours and 38 minutes, followed by stirring for further 10 hours and 43 minutes. The precipitated solid was filtered off and washed with a mixture of ethanol and tert-butyl methyl ether (75 ml+150 ml). The resulting solid was dried under reduced pressure at 50° C. to give the title compound (106.40 g, yield: 70.9%).

¹H-NMR (400 MHz, DMSO-d₆) δ ppm; 1.05 (3H, d, J=6 Hz), 2.32-2.45 (2H, m), 2.64-2.78 (1H, m), 2.92-3.12 (3H, m), 3.75 (3H, s), 3.80-3.94 (2H, m), 5.04 (2H, dd, J=12, 16 Hz), 5.77 (2H, s), 6.90-6.96 (2H, m), 7.26-7.38 (7H, m), 7.52-7.58 (4H, m), 7.66-7.72 (2H, m), 7.95-8.05 (2H, m).
Analysis by HPLC;
(Analysis conditions) Column: CHIRALCEL OJ-H (manufactured by Daicel Chemical Industries, Ltd.) (0.46 cm diameter×25 cm), eluent: hexane/ethanol/diethylamine=850/150/1 (v/v/v), flow rate: 1 ml/min., detection: UV (226 nm) (Analysis result) The resulting title compound was analyzed under the above analysis conditions, and a peak with a retention time of 8.62 minutes (enantiomeric excess: 98.0% ee) and a peak with a retention time of 10.9 minutes were observed.

Reference Example 2b (4-Methoxyphenyl)methyl (3S*,4S*)-1-benzyl-4-methylpyrrolidine-3-carboxylate Ethyl acetate (900 ml) was added to (−)-dibenzoyl-L-tartrate of (4-methoxyphenyl)methyl (3S*,4S*)-1-benzyl-4-methylpyrrolidine-3-carboxylate obtained in Reference Example 2a (104.0 g), and a 1N aqueous sodium hydroxide solution (600 ml) was added with stirring. The aqueous layer was discarded, and the organic layer was washed with water twice (100 ml, 50 ml). The resulting organic layer was concentrated under reduced pressure at 50° C. to give the title compound (49.8 g, yield: 98.5%).
¹H-NMR (400 MHz, CDCl₃) δ ppm; 1.12 (3H, d, J=7 Hz), 2.19 (1H, dd, J=6, 9 Hz), 2.44-2.62 (2H, m), 2.73-2.84 (2H, m), 2.85-2.92 (1H, m), 3.55 (1H, d, J=13 Hz), 3.63 (1H, d, J=13 Hz), 3.81 (3H, s), 5.02-5.10 (2H, m), 6.85-6.90 (2H, m), 7.21-7.33 (7H, m).

Reference Example 2c (3R*,4S*)-3-[2-(tert-Butoxy)-2-oxoethyl]-4-methylpyrrolidine-3-carboxylic acid Tetrahydrofuran (200 ml) was added to (4-methoxyphenyl)methyl (3S*,4S*)-1-benzyl-4-methylpyrrolidine-3-carboxylate obtained in Reference Example 2b (29.50 g, 87 mmol), followed by azeotropic dehydration. Tetrahydrofuran (200 ml) was further added, followed by azeotropic dehydration. Tetrahydrofuran (400 ml) was added to this product, which was cooled in a dry ice-ethanol bath, and a lithium diisopropylamide/n-hexane-tetrahydrofuran solution (129 ml, 1.11M, 144 mmol) was added over 27 minutes. After 30 minutes, a solution of tert-butyl bromoacetate (21.20 g, 144 mmol) in tetrahydrofuran (30 ml) was added over seven minutes. After 39 minutes, a 20% aqueous ammonium chloride solution (440 ml) was added, and ethyl acetate (440 ml) was further added to perform extraction. The resulting organic layer was washed with water twice (60 ml, 60 ml) and concentrated under reduced pressure at 30° C. Methanol (150 ml) and palladium hydroxide (885 mg) were added to the resulting concentrate, followed by stirring under hydrogen pressure (0.35 MPa) for seven hours and 20 minutes. Water (200 ml) and tetrahydrofuran (100 ml) were added to the reaction liquid, followed by filtration, and the catalyst was sequentially washed with methanol (50 ml) and water (50 ml×2). The filter washings were concentrated under reduced pressure at 50° C., the resulting aqueous layer was washed with tert-butyl methyl ether (100 ml), and the aqueous layer after washing was concentrated under reduced pressure at 50° C. Methanol (150 ml) was added to the resulting residue, and the mixture was ultrasonically treated and then filtered. The resulting solid was dried under reduced pressure at 50° C. to give the title compound (8.16 g, yield: 38.5%).
¹H-NMR (400 MHz, D₂O) δ ppm; 1.00 (3H, d, J=7 Hz), 1.45 (9H, s), 2.16-2.28 (1H, m), 2.33 (1H, d, J=17 Hz), 2.97 (1H, d, J=17 Hz), 3.08 (1H, t, J=12 Hz), 3.22 (1H, d, J=12 Hz), 3.50-3.58 (1H, m), 4.07 (1H, d, J=12 Hz).

Reference Example 3

(3R*,4S*)-3-[2-(tert-Butoxy)-2-oxoethyl]-4-methylpyrrolidine-3-carboxylic acid (R)-(−)-1,1'-binaphthyl-2,2'-diyl hydrogenphosphate ethanol solvate (3RS,4SR)-3-[2-(tert-Butoxy)-2-oxoethyl]-4-methylpyrrolidine-3-carboxylic acid obtained by a method similar to that of Reference Example 1a (500 mg), (R)-(−)-1,1'-binaphthyl-2,2'-diyl hydrogenphosphate (359 mg), ethanol (10.0 mL) and water (10.0 mL) were sequentially added to a 50 mL round bottom flask, followed by stirring at room temperature for about 22 hours. The precipitated solid was collected by filtration and washed with a 1:1 ethanol-water mixture (2 mL). The wet product was dried under reduced pressure at 40° C. for about one hour to give the title compound (269 mg, yield: 20.5%).
¹H-NMR (400 MHz, DMSO-d₆) δ ppm: 0.88 (3H, d, J=7 Hz), 1.06 (3H, t, J=7 Hz), 1.38 (9H, s), 2.09-2.16 (1H, m), 2.44 (1H, d, J=18 Hz), 2.74 (1H, t, J=12 Hz), 2.87 (1H, d, J=18 Hz), 3.11 (1H, d, J=12 Hz), 3.41-3.47 (2H, m), 3.81 (1H, d, J=12 Hz), 4.36 (1H, t, J=5 Hz), 7.21 (2H, d, J=9 Hz), 7.28-7.31 (2H, t, J=8 Hz), 7.38-7.45 (4H, m), 8.02 (4H, t, J=8 Hz).

8.85 mg of the above white solid was weighed out in a screw glass vessel. 0.2 mL of MilliQ water and 0.8 mL of 99.5% ethanol were added thereto. Thereafter, this was equally divided into three portions in 1.5 mL LCMS vials, and the vials were loosely capped and left to stand at room temperature. After nine days, crystals were observed to be precipitated in the vials. An X-ray diffraction experiment was performed with R-AXIS RAPID II (Rigaku Corporation) using the resulting single crystals (0.40×0.40×0.06 mm). The crystallographic data and structural analysis results are shown in Table 1, and the atomic coordinate data are shown in Tables 2 to 4. The absolute structure of the title compound was specified from such results.

TABLE 1

| | |
|---|---|
| Temperature | 296 K |
| Wavelength | 1.5418 Å |
| Crystal system, space group | Monoclinic system, P2₁ |
| Lattice parameter | a = 12.8692 (4) Å |
| | b = 10.9651 (3) Å |
| | c = 23.8299 (7) Å |
| | β = 95.637 (2)° |
| Volume | 3346.4 (2) Å³ |
| Z value, calculated density | 4, 1.357 g/cm³ |
| Absorption coefficient | 12.406 cm⁻¹ |
| Crystal size | 0.40 × 0.40 × 0.06 mm |
| Maximum measured 2θ | 136.5° |
| Total number of reflections/ number of unique reflections | 35631/11955 [R (Strength) = 0.0631] |
| Completeness | 98.5% |
| Structure solution | Direct method (SIR92) |
| Refinement | Least-squares method for F² |
| Data/parameter | 11955/835 |
| Goodness of fit indicator | 1.103 |
| R factor (all data) | 0.0739 |
| R factor (I > 2σ (I)) | 0.0477 |

TABLE 1-continued

| | |
|---|---|
| Flack parameter | −0.00 (3) |
| Difference between the maximum and minimum peaks | 0.43 and −0.40 e/Å$^3$ |

TABLE 2

| | x | z | y | U (eq) |
|---|---|---|---|---|
| P1 | −0.30549 (7) | 0.02152 (8) | 0.50227 (4) | 3.88 (2) |
| P2 | 0.27020 (8) | 0.29225 (8) | 0.07402 (5) | 4.25 (2) |
| O1 | −0.3526 (2) | 0.1284 (2) | 0.52810 (1) | 4.36 (6) |
| O2 | −0.3275 (2) | −0.1009 (2) | 0.5232 (2) | 4.78 (6) |
| O3 | −0.1819 (2) | 0.0485 (3) | 0.5071 (1) | 4.17 (6) |
| O4 | −0.3345 (2) | 0.0201 (3) | 0.4358 (3) | 4.33 (5) |
| O5 | 0.3291 (3) | 0.3968 (3) | 0.0554 (3) | 5.68 (7) |
| O6 | 0.3241 (3) | 0.1735 (3) | 0.0789 (2) | 5.81 (7) |
| O7 | 0.1636 (2) | 0.2859 (3) | 0.0336 (1) | 4.07 (5) |
| O8 | 0.2280 (2) | 0.3167 (3) | 0.1343 (1) | 4.30 (5) |
| O9 | 0.4552 (3) | −0.0428 (3) | 0.0300 (2) | 5.31 (7) |
| O10 | 0.3598 (3) | −0.0464 (3) | 0.1033 (1) | 4.86 (6) |
| O11 | 0.5908 (3) | −0.1764 (4) | 0.1547 (2) | 7.02 (9) |
| O12 | 0.5024 (3) | −0.2371 (3) | 0.2258 (2) | 5.75 (7) |
| O13 | 0.2710 (3) | −0.1574 (3) | 0.4519 (2) | 5.39 (7) |
| O14 | 0.4273 (2) | −0.0998 (3) | 0.4927 (2) | 5.64 (7) |
| O15 | 0.3547 (3) | −0.0085 (4) | 0.3501 (2) | 7.00 (9) |
| O16 | 0.1998 (2) | 0.0539 (3) | 0.3086 (1) | 5.14 (6) |
| O17 | 0.5245 (4) | −0.5826 (7) | 0.1062 (3) | 8.6 (1) |
| O18 | 0.417 (1) | 0.432 (1) | 0.3597 (7) | 27.9 (7) |
| N1 | 0.4848 (4) | −0.2939 (4) | −0.0160 (2) | 5.49 (9) |
| N2 | 0.4327 (4) | 0.1896 (4) | 0.5073 (2) | 4.89 (9) |
| C1 | −0.1225 (3) | −0.0260 (4) | 0.4752 (2) | 4.06 (8) |
| C2 | −0.1255 (3) | −0.0052 (4) | 0.4183 (2) | 4.19 (8) |
| C3 | −0.0719 (3) | −0.0909 (4) | 0.3854 (2) | 4.69 (9) |
| C4 | −0.0791 (4) | −0.0875 (5) | 0.3263 (2) | 5.8 (1) |
| C5 | −0.0310 (5) | −0.1735 (6) | 0.2967 (3) | 7.8 (2) |
| C6 | 0.0283 (6) | −0.2649 (6) | 0.3240 (4) | 8.6 (2) |
| C7 | 0.0370 (4) | −0.2729 (5) | 0.3811 (3) | 7.3 (2) |
| C8 | −0.0124 (4) | −0.1871 (4) | 0.4143 (3) | 5.2 (1) |
| C9 | −0.0085 (4) | −0.1966 (5) | 0.4725 (3) | 5.6 (1) |
| C10 | −0.0627 (3) | −0.1192 (4) | 0.5031 (2) | 5.00 (9) |
| C11 | −0.2906 (3) | 0.1083 (4) | 0.4029 (2) | 4.33 (8) |
| C12 | −0.1878 (3) | 0.0971 (4) | 0.3927 (2) | 4.21 (8) |
| C13 | −0.1444 (3) | 0.1916 (4) | 0.3603 (2) | 4.43 (8) |
| C14 | −0.0375 (4) | 0.1966 (4) | 0.3516 (2) | 5.27 (9) |
| C15 | 0.0028 (4) | 0.2881 (5) | 0.3224 (3) | 6.5 (2) |
| C16 | −0.0635 (5) | 0.3792 (5) | 0.2969 (3) | 6.9 (2) |
| C17 | −0.1655 (5) | 0.3780 (5) | 0.3048 (3) | 6.7 (2) |
| C18 | −0.2101 (4) | 0.2867 (5) | 0.3367 (2) | 5.21 (9) |
| C19 | −0.3152 (4) | 0.2885 (5) | 0.3465 (2) | 6.1 (1) |
| C20 | −0.3559 (4) | 0.2021 (5) | 0.3796 (2) | 5.7 (1) |
| C21 | 0.0837 (3) | 0.2113 (4) | 0.0497 (2) | 3.85 (7) |
| C22 | 0.0252 (3) | 0.2484 (3) | 0.0923 (2) | 3.49 (7) |
| C23 | −0.0515 (3) | 0.1662 (3) | 0.1095 (2) | 3.81 (7) |
| C24 | −0.1043 (3) | 0.1861 (4) | 0.1576 (2) | 4.44 (8) |
| C25 | −0.1780 (4) | 0.1049 (5) | 0.1724 (2) | 5.8 (1) |
| C26 | −0.2030 (5) | 0.0004 (5) | 0.1398 (2) | 6.9 (2) |
| C27 | −0.1507 (4) | −0.0222 (5) | 0.0945 (3) | 6.4 (2) |
| C28 | −0.0720 (4) | 0.0561 (4) | 0.0784 (2) | 4.68 (9) |
| C29 | −0.0149 (4) | 0.0295 (4) | 0.0330 (2) | 5.6 (1) |
| C30 | 0.0637 (4) | 0.1038 (4) | 0.0199 (2) | 5.28 (9) |

TABLE 3

| | | | | |
|---|---|---|---|---|
| C31 | 0.1477 (3) | 0.4005 (4) | 0.1378 (2) | 3.83 (7) |
| C32 | 0.0475 (3) | 0.3697 (3) | 0.1190 (2) | 3.36 (7) |
| C33 | −0.0330 (3) | 0.4594 (4) | 0.1223 (2) | 3.65 (7) |
| C34 | −0.1383 (3) | 0.4398 (4) | 0.1003 (2) | 4.30 (8) |
| C35 | −0.2124 (4) | 0.5278 (5) | 0.1034 (2) | 5.5 (1) |
| C36 | −0.1866 (5) | 0.6406 (5) | 0.1268 (3) | 6.4 (2) |
| C37 | −0.0872 (5) | 0.6641 (4) | 0.1475 (2) | 6.3 (2) |
| C38 | −0.0064 (4) | 0.5749 (4) | 0.1465 (2) | 4.69 (8) |
| C39 | 0.0979 (4) | 0.5978 (4) | 0.1669 (2) | 5.5 (1) |
| C40 | 0.1740 (4) | 0.5145 (4) | 0.1631 (2) | 5.02 (9) |
| C41 | 0.5212 (4) | −0.2809 (4) | 0.0451 (2) | 4.50 (8) |
| C42 | 0.4249 (3) | −0.2360 (3) | 0.0731 (2) | 3.50 (7) |

TABLE 3-continued

| | | | | |
|---|---|---|---|---|
| C43 | 0.3342 (4) | −0.2979 (4) | 0.0362 (2) | 4.49 (8) |
| C44 | 0.3695 (4) | −0.2987 (6) | −0.0228 (2) | 6.5 (2) |
| C45 | 0.4161 (3) | −0.0981 (4) | 0.0671 (2) | 3.91 (7) |
| C46 | 0.4261 (3) | −0.2755 (4) | 0.1337 (2) | 3.94 (7) |
| C47 | 0.5158 (4) | −0.2244 (4) | 0.1718 (2) | 4.42 (8) |
| C48 | 0.2262 (4) | −0.2444 (5) | 0.0384 (2) | 6.1 (1) |
| C49 | 0.5829 (4) | −0.1967 (7) | 0.2712 (2) | 6.9 (2) |
| C50 | 0.6778 (5) | −0.2758 (8) | 0.2683 (4) | 11.6 (3) |
| C51 | 0.5293 (6) | −0.2179 (9) | 0.3237 (3) | 11.8 (3) |
| C52 | 0.6039 (6) | −0.0633 (8) | 0.2658 (3) | 10.2 (2) |
| C53 | 0.4024 (3) | 0.1337 (4) | 0.4509 (2) | 4.17 (8) |
| C54 | 0.3066 (3) | 0.0503 (3) | 0.4574 (2) | 3.28 (6) |
| C55 | 0.2645 (3) | 0.1071 (4) | 0.5115 (2) | 4.11 (7) |
| C56 | 0.3633 (4) | 0.1414 (5) | 0.5485 (2) | 5.27 (9) |
| C57 | 0.3424 (3) | −0.0754 (3) | 0.4684 (2) | 3.97 (7) |
| C58 | 0.2247 (3) | 0.0656 (4) | 0.4074 (2) | 3.86 (7) |
| C59 | 0.2682 (4) | 0.0315 (4) | 0.3529 (2) | 4.59 (8) |
| C60 | 0.1912 (4) | 0.0265 (5) | 0.5417 (2) | 6.3 (1) |
| C61 | 0.2251 (4) | 0.0340 (5) | 0.2506 (2) | 5.5 (1) |
| C62 | 0.3176 (5) | 0.1142 (6) | 0.2394 (3) | 8.1 (2) |
| C63 | 0.2454 (5) | −0.1016 (6) | 0.2416 (2) | 7.2 (2) |
| C64 | 0.1280 (5) | 0.0737 (7) | 0.2156 (2) | 8.6 (2) |
| C65 | 0.528 (1) | −0.615 (1) | 0.1682 (6) | 15.5 (4) |
| C66 | 0.566 (2) | −0.715 (2) | 0.1763 (6) | 18.6 (5) |
| C67 | 0.294 (2) | 0.503 (2) | 0.3239 (6) | 20.9 (6) |
| C68 | 0.285 (2) | 0.370 (2) | 0.3574 (6) | 19.7 (6) |
| H1 | 0.5162 | −0.2306 | −0.0325 | 8.23 |
| H2A | 0.4928 | 0.1800 | 0.5194 | 7.43 |
| H2B | 0.4204 | 0.2798 | 0.5013 | 8.18 |
| H4 | −0.1173 | −0.0257 | 0.3071 | 6.91 |
| H5 | 0.4183 | 0.3988 | 0.0833 | 9.66 |
| H5A | −0.0381 | −0.1706 | 0.2575 | 9.35 |
| H6 | 0.0623 | −0.3213 | 0.3030 | 10.32 |
| H7 | 0.0762 | −0.3357 | 0.3988 | 8.73 |
| H9 | 0.0372 | −0.2466 | 0.4886 | 6.92 |
| H10 | −0.0604 | −0.1277 | 0.5420 | 6.00 |
| H13 | 0.2937 | −0.2206 | 0.4609 | 5.92 |
| H14 | 0.0067 | 0.1351 | 0.3665 | 6.33 |
| H15 | 0.0742 | 0.2910 | 0.3191 | 7.77 |
| H16 | −0.0369 | 0.4395 | 0.2749 | 8.32 |
| H17 | −0.2082 | 0.4395 | 0.2887 | 8.08 |

TABLE 4

| | | | | |
|---|---|---|---|---|
| H19 | −0.3584 | 0.3496 | 0.3303 | 7.37 |
| H20 | −0.4257 | 0.2053 | 0.3865 | 6.80 |
| H24 | −0.0892 | 0.2550 | 0.1796 | 5.33 |
| H25 | −0.2118 | 0.1192 | 0.2045 | 7.00 |
| H26 | −0.2550 | −0.0525 | 0.1493 | 8.25 |
| H27 | −0.1672 | −0.0919 | 0.0732 | 7.65 |
| H29 | −0.0309 | −0.0400 | 0.0115 | 6.67 |
| H30 | 0.1039 | 0.0826 | −0.0090 | 6.34 |
| H34 | −0.1572 | 0.3655 | 0.0834 | 5.16 |
| H35 | −0.2811 | 0.5119 | 0.0896 | 6.63 |
| H36 | −0.2378 | 0.7001 | 0.1283 | 7.71 |
| H37 | −0.0708 | 0.7405 | 0.1628 | 7.58 |
| H39 | 0.1150 | 0.6728 | 0.1835 | 6.60 |
| H40 | 0.2425 | 0.5317 | 0.1769 | 6.02 |
| H41A | 0.5777 | −0.2223 | 0.0506 | 5.40 |
| H41B | 0.5455 | −0.3586 | 0.0609 | 5.40 |
| H43 | 0.3313 | −0.3830 | 0.0486 | 5.38 |
| H44A | 0.3457 | −0.3723 | −0.0427 | 7.84 |
| H44B | 0.3413 | −0.2287 | −0.0441 | 7.84 |
| H46A | 0.3612 | −0.2504 | 0.1478 | 4.73 |
| H46B | 0.4292 | −0.3638 | 0.1354 | 4.73 |
| H48A | 0.1754 | −0.2967 | 0.0184 | 7.27 |
| H48B | 0.2233 | −0.1651 | 0.0211 | 7.27 |
| H48C | 0.2114 | −0.2372 | 0.0770 | 7.27 |
| H50A | 0.6611 | −0.3584 | 0.2771 | 13.90 |
| H50B | 0.7332 | −0.2470 | 0.2950 | 13.90 |
| H50C | 0.6998 | −0.2722 | 0.2310 | 13.90 |
| H51A | 0.5307 | −0.1442 | 0.3454 | 14.10 |
| H51B | 0.5649 | −0.2814 | 0.3457 | 14.10 |
| H51C | 0.4582 | −0.2417 | 0.3134 | 14.10 |
| H52A | 0.6571 | −0.0513 | 0.2408 | 12.22 |
| H52B | 0.6270 | −0.0302 | 0.3022 | 12.22 |
| H52C | 0.5411 | −0.0226 | 0.2509 | 12.22 |

TABLE 4-continued

| | | | | |
|---|---|---|---|---|
| H53A | 0.4591 | 0.0845 | 0.4392 | 5.00 |
| H53B | 0.3857 | 0.1966 | 0.4228 | 5.00 |
| H55  | 0.2271 | 0.1828 | 0.5009 | 4.93 |
| H56A | 0.3491 | 0.2033 | 0.5759 | 6.32 |
| H56B | 0.3940 | 0.0708 | 0.5683 | 6.32 |
| H58A | 0.1662 | 0.0127 | 0.4131 | 4.64 |
| H58B | 0.1992 | 0.1488 | 0.4048 | 4.64 |
| H60A | 0.1278 | 0.0136 | 0.5177 | 7.56 |
| H60B | 0.1754 | 0.0656 | 0.5759 | 7.56 |
| H60C | 0.2241 | −0.0506 | 0.5505 | 7.56 |
| H62A | 0.3110 | 0.1922 | 0.2570 | 9.71 |
| H62B | 0.3190 | 0.1250 | 0.1995 | 9.71 |
| H62C | 0.3813 | 0.0759 | 0.2548 | 9.71 |
| H63A | 0.2688 | −0.1136 | 0.2050 | 8.68 |
| H63B | 0.1821 | −0.1466 | 0.2443 | 8.68 |
| H63C | 0.2981 | −0.1297 | 0.2700 | 8.68 |
| H64A | 0.1146 | 0.1581 | 0.2229 | 10.35 |
| H64B | 0.0701 | 0.0253 | 0.2250 | 10.35 |
| H64C | 0.1370 | 0.0633 | 0.1764 | 10.35 |

The absolute structures of the compounds of Examples 1 to 14 are specified based on the information obtained in Reference Example 3, and the compounds of Examples 1 to 14 are named as follows.

Example 1: Chiral form of 2-[(3S,4R)-1-{[2-Chloro-6-(trifluoromethyl)phenyl]methyl}-3-{[1-(2-fluoropentyl)piperidin-4-yl]carbamoyl}-4-methylpyrrolidin-3-yl]acetic acid Example 2: 2-[(3S,4R)-1-[(2,6-Dichlorophenyl)methyl]-3-({1-[(4,4-difluorocyclohexyl)methyl]piperidin-4-yl}carbamoyl)-4-methylpyrrolidin-3-yl]acetic acid Examples 3 to 5: 2-[(3S,4R)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl]acetic acid Example 6: 2-[(3S,4R)-1-[(2-Chloro-6-methylphenyl)methyl]-3-{[1-(cyclohex-1-en-1-ylmethyl)piperidin-4-yl]carbamoyl}-4-methylpyrrolidin-3-yl]acetic acid Example 7: 2-[(3S,4R)-1-{[2-Chloro-6-(trifluoromethyl)phenyl]methyl}-3-{[1-(cyclopent-1-en-1-ylmethyl)piperidin-4-yl]carbamoyl}-4-methylpyrrolidin-3-yl]acetic acid Example 8: 2-[(3S,4R)-1-[(2-Chloro-6-methylphenyl)methyl]-3-{[(1-cyclopent-1-en-1-ylmethyl)piperidin-4-yl]carbamoyl}-4-methylpyrrolidin-3-yl]acetic acid Example 9: 2-[(3S,4R)-3-{[(3S)-1-(Cyclohex-1-en-1-ylmethyl)pyrrolidin-3-yl]carbamoyl}-1-[2,6-dichlorophenyl)methyl]-4-methylpyrrolidin-3-yl]acetic acid Example 10: 2-[(3S,4R)-1-{[2-Chloro-6-(difluoromethyl)phenyl]methyl}-3-[(1-hexylpiperidin-4-yl)carbamoyl]-4-methylpyrrolidin-3-yl]acetic acid Example 11: 2-[(3S,4R)-3-{[(1-Cyclohex-1-en-1-ylmethyl)piperidin-4-yl]carbamoyl}-1-[(2,6-dichlorophenyl)methyl]-4-methylpyrrolidin-3-yl]acetic acid Example 12: 2-[(3S,4R)-1-{[2-Chloro-6-(difluoromethyl)phenyl]methyl}-3-{[1-(cyclohex-1-en-1-ylmethyl)piperidin-4-yl]carbamoyl}-4-methylpyrrolidin-3-yl]acetic acid Example 13: 2-[(3S,4R)-1-{[2-chloro-6-(difluoromethyl)phenyl]methyl}-3-{[1-(cyclopent-1-en-1-ylmethyl)piperidin-4-yl]carbamoyl}-4-methylpyrrolidin-3-yl]acetic acid Example 14: 2-[(3S,4R)-1-{[2-Chloro-6-(difluoromethyl)phenyl]methyl}-3-{[1-(cyclohexylmethyl)piperidin-4-yl]carbamoyl}-4-methylpyrrolidin-3-yl]acetic acid The structural formulas of Example Compounds 1 to 8 are as follows.

[Chemical Formula 13]

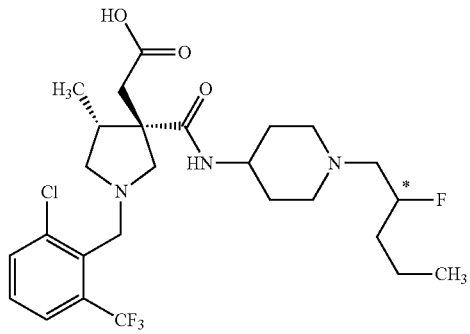

Example 1

*Chiral, stereochemistry was not determined

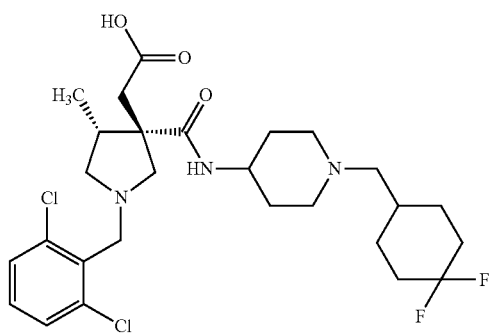

Example 2

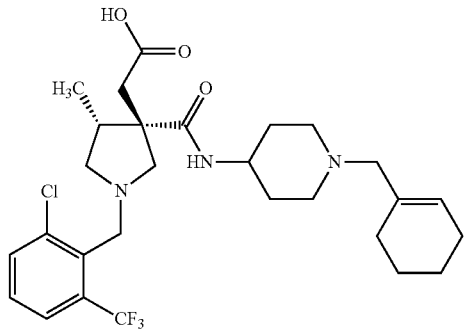

Example 3, 4 and 5

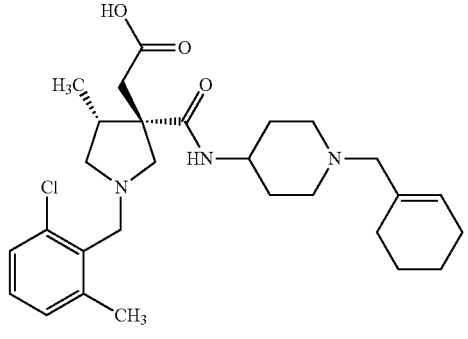

Example 6

Example 7

Example 8

The structural formulas of Example Compounds 9 to 14 are as follows.

[Chemical Formula 14]

Example 9

Example 10

Example 11

Example 12

Example 13

Example 14

Test Example 1

Inhibition of Cell Migration in Fractalkine-Induced Chemotaxis Assay (1) Method

The inhibitory effects of the example compounds on fractalkine-induced cell migration were examined using CX3CR1-transfected B300 cells After equilibrating the Transwell plate (24-well clusters, pore size: 5 μm, manufactured by Corning Incorporated), a fractalkine solution (0.3 nM, manufactured by R&D Systems, Inc.) was added to the lower wells. CX3CR1-expressing B300 cells which were preincubated with the test compound (0.001, 0.003, 0.01 or 0.03 μM) for 30 minutes were placed in the upper layer wells, followed by incubation under the condition of 5% $CO_2$ for 3.5 hours at 37° C. The number of cells migrated to the lower wells was evaluated using CellTiter (manufactured by Promega Corporation).

The inhibitory rate of the test compound on fractalkine-induced cell migration was calculated by the following formula, where [A] is the number of migrated cells in the presence of both fractalkine and the test compound, [B] is the number of migrated cells in the presence of fractalkine and in the absence of the test compound, and [C] is the number of migrated cells in the absence of both fractalkine and the test compound; the 50% inhibitory concentration ($IC_{50}$) was calculated based on the inhibitory rate.

Inhibitory rate (%)=[1−{(A−C)/(B−C)}]×100

(2) Results

The results of this test example are shown in the following table.

TABLE 5

| Test compound | $IC_{50}$ (nM) |
|---|---|
| Example 1 | 13 |
| Example 2 | 21 |
| Example 3 | 4 |
| Example 6 | 11 |
| Example 7 | 5 |
| Example 8 | 31 |
| Example 9 | 16 |
| Example 10 | 14 |
| Example 11 | 6 |
| Example 12 | 6 |
| Example 13 | 16 |
| Example 14 | 12 |

Test Example 2

Amelioration of Body Weight Loss in T Cell Transfer-Induced Colitis Model (1) Method By using colitis-induced SCID mice in which CD4-positive, CD45RB-high cells isolated from BALB/c mice splenocytes were injected, the efficacy of the example compounds was evaluated by the body weight changes. The experiment was performed over 31 days. On Day 1, CD4-positive, CD45RB-high cells isolated from the spleen of BALB/c mice ($5\times10^5$ cells/mouse) were intravenously administered to SCID mice. From Day 16 to 31, the example compound was orally administered to the SCID mice once a day, followed by measuring body weights of all animals on Day 19, 22, 24, 26, 29 and 31.

The efficacy was evaluated by body weight changes on Day 19, 22, 24, 26, 29 or 31. The body weight change (%) was determined by the formula shown below, where [A] is the body weight on Day 16, and [B] is the body weight on each day of body weight measurement (Day 19, 22, 24, 26, 29 or 31).

body weight change (%)=B/A×100

(2) Results

Figure 2:
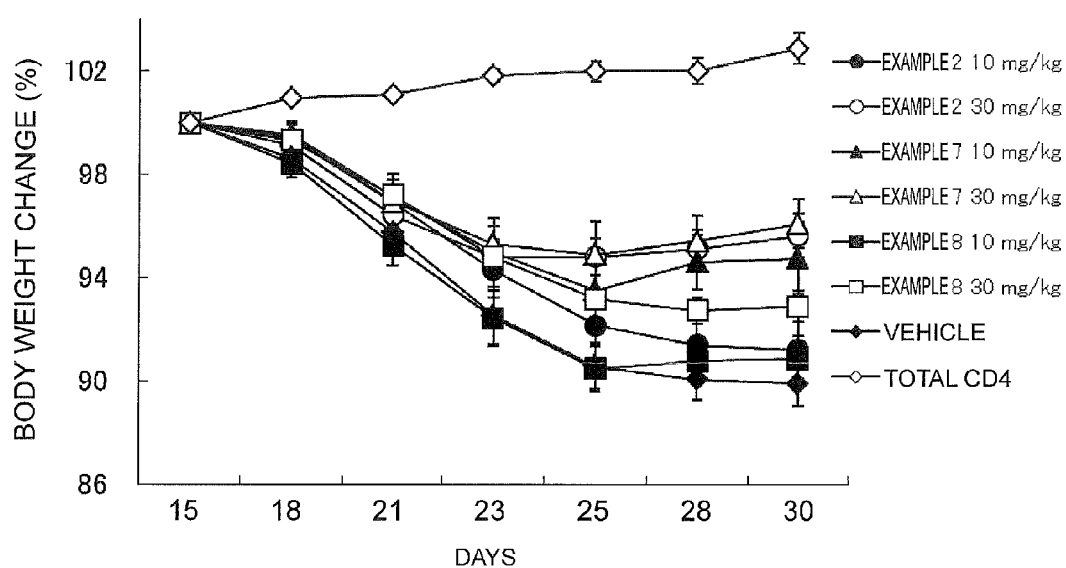
FIG. 2 shows a graph showing the results of Test Example 2 for the compounds of Examples 2, 7 and 8.
Figure 3:
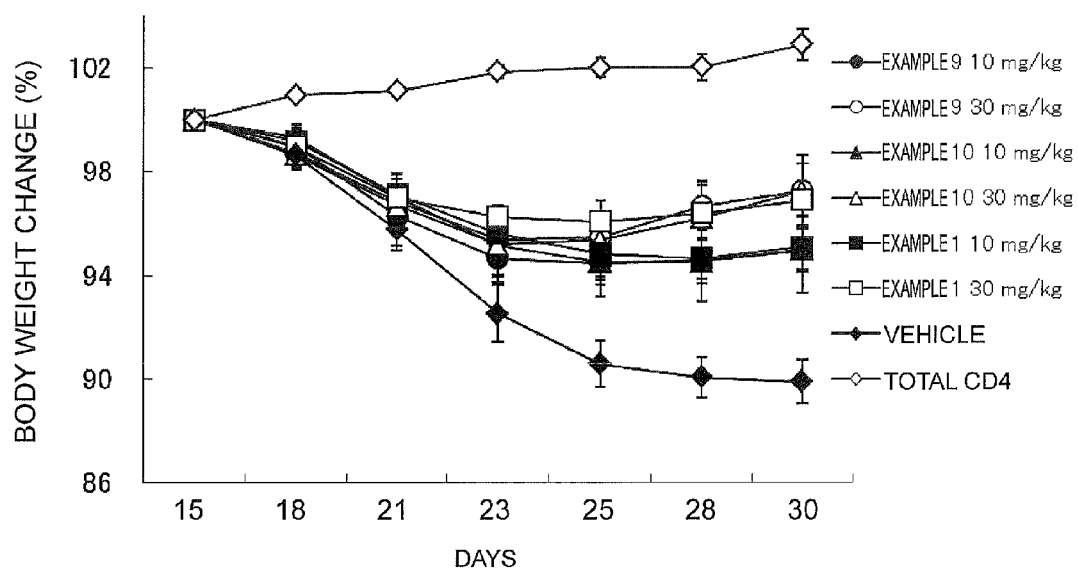
FIG. 3 shows a graph showing the results of Test Example 2 for the compounds of Examples 1, 9 and 10.
Figure 4:
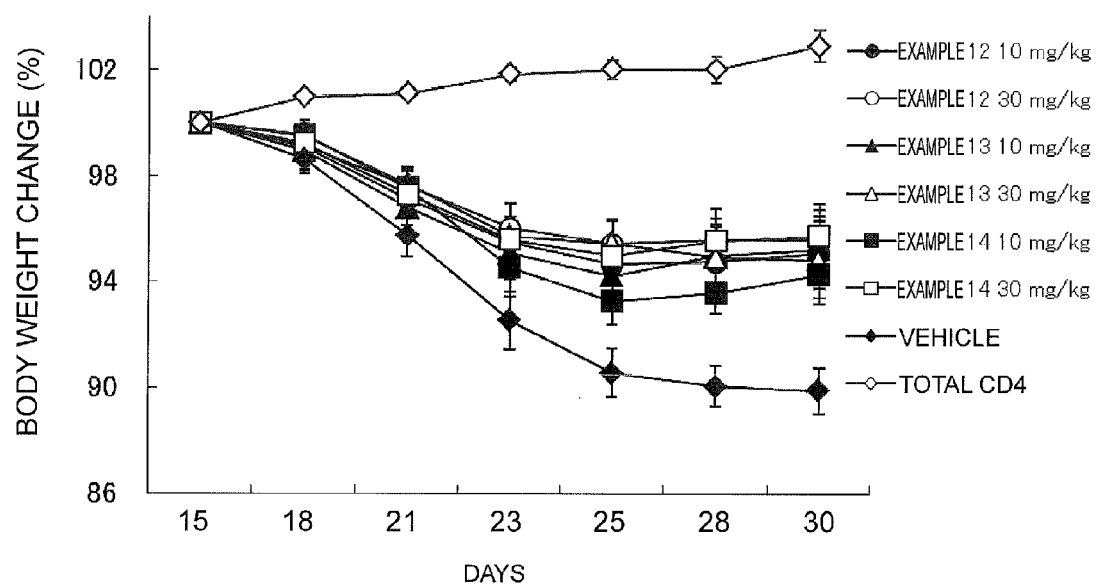
FIG. 4 shows a graph showing the results of Test Example 2 for the compounds of Examples 12, 13 and 14.

The results are shown in FIGS. 1 to 4. The abscissa in the figures indicates the number of days elapsed, where the day on which CD4-positive, CD45RB-high cells isolated from the spleen of BALB/c mice ($5\times10^5$ cells/mouse) were intravenously administered to SCID mice is Day 0.

What is claimed is:

1. A compound represented by formula (1) or pharmaceutically acceptable salt thereof:

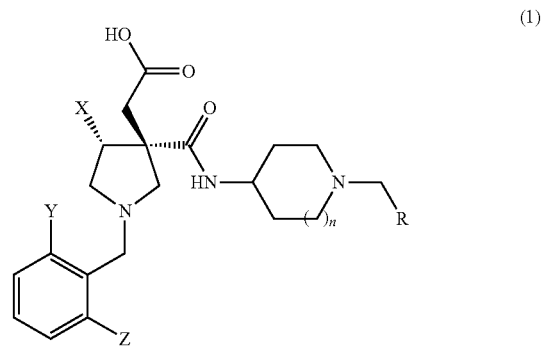

wherein R represents a $C_{1-6}$ alkyl group unsubstituted or having 1 to 3 substituents selected from Substituent Group A, a $C_{3-8}$ cycloalkyl group unsubstituted or having 1 to 3 substituents selected from Substituent Group A, or a $C_{3-8}$ cycloalkenyl group unsubstituted or having 1 to 3 substituents selected from Substituent Group A, X represents a $C_{1-6}$ alkyl group, Y and Z are the same or different from each other and each represents a halogen atom or a $C_{1-6}$ alkyl group unsubstituted or having 1 to 3 substituents selected from Substituent Group B, n represents 0 or 1, Substituent Group A consists of halogen atoms, and Substituent Group B consists of halogen atoms.

2. The compound or pharmaceutically acceptable salt thereof according to claim 1, wherein R is a fluorobutyl group, a pentyl group, a cyclohexyl group, a difluorocyclohexyl group, a cyclopentenyl group or a cyclohexenyl group.

3. The compound or pharmaceutically acceptable salt thereof according to claim 1, wherein X is a methyl group.

4. The compound or pharmaceutically acceptable salt thereof according to claim 1, wherein Y is a chlorine atom.

5. The compound or pharmaceutically acceptable salt thereof according to claim 1, wherein Z is a chlorine atom, a methyl group, a difluoromethyl group or a trifluoromethyl group.

6. The compound or pharmaceutically acceptable salt thereof according to claim 1, wherein n is 1.

7. A compound selected from the group consisting of:

2-[(3S,4R)-1-{[2-chloro-6-(trifluoromethyl)phenyl]methyl}-3-{[1-(2-fluoropentyl)piperidin-4-yl]carbamoyl}-4-methylpyrrolidin-3-yl]acetic acid, 2-[(3S,4R)-1-[(2,6-dichlorophenyl)methyl]-3-({1-[(4,4-difluorocyclohexyl)methyl]piperidin-4-yl}carbamoyl)-4-methylpyrrolidin-3-yl]acetic acid,
2-[(3S,4R)-1-{[2-chloro-6-(trifluoromethyl)phenyl]methyl}-3-{[1-(cyclohex-1-en-1-ylmethyl)piperidin-4-yl]carbamoyl}-4-methylpyrrolidin-3-yl]acetic acid,
2-[(3S,4R)-1-[(2-chloro-6-methylphenyl)methyl]-3-{[1-(cyclohex-1-en-1-ylmethyl)piperidin-4-yl]carbamoyl}-4-methylpyrrolidin-3-yl]acetic acid,
2-[(3S,4R)-1-{[2-chloro-6-(trifluoromethyl)phenyl]methyl}-3-{[1-(cyclopent-1-en-1-ylmethyl)piperidin-4-yl]carbamoyl}-4-methylpyrrolidin-3-yl]acetic acid,
2-[(3S,4R)-1-[(2-chloro-6-methylphenyl)methyl]-3-{[(1-cyclopent-1-en-1-ylmethyl)piperidin-4-yl]carbamoyl}-4-methylpyrrolidin-3-yl]acetic acid,
2-[(3S,4R)-3-{[(3S)-1-(cyclohex-1-en-1-ylmethyl)pyrrolidin-3-yl]carbamoyl}-1-[(2,6-dichlorophenyl)methyl]-4-methylpyrrolidin-3-yl]acetic acid,
2-[(3S,4R)-1-{[2-chloro-6-(difluoromethyl)phenyl]methyl}-3-[(1-hexylpiperidin-4-yl)carbamoyl]-4-methylpyrrolidin-3-yl]acetic acid,
2-[(3S,4R)-3-{[(1-cyclohex-1-en-1-ylmethyl)piperidin-4-yl]carbamoyl}-1-[(2,6-dichlorophenyl)methyl]-4-methylpyrrolidin-3-yl]acetic acid,
2-[(3S,4R)-1-{[2-chloro-6-(difluoromethyl)phenyl]methyl}-3-{[1-(cyclohex-1-en-1-ylmethyl)piperidin-4-yl]carbamoyl}-4-methylpyrrolidin-3-yl]acetic acid,
2-[(3S,4R)-1-{[2-chloro-6-(difluoromethyl)phenyl]methyl}-3-{[1-(cyclopent-1-en-1-ylmethyl)piperidin-4-yl]carbamoyl}-4-methylpyrrolidin-3-yl]acetic acid and
2-[(3S,4R)-1-{[2-chloro-6-(difluoromethyl)phenyl]methyl}-3-{[1-(cyclohexylmethyl)piperidin-4-yl]carbamoyl}-4-methylpyrrolidin-3-yl]acetic acid,
or a pharmaceutically acceptable salt thereof.

8. A medicine comprising the compound or pharmaceutically acceptable salt thereof according to claim 1 as an active ingredient.

9. 2-[(3S,4R)-1-[(2,6-Dichlorophenyl)methyl]-3-({1-[(4,4-difluorocyclohexyl)methyl]piperidin-4-yl}carbamoyl)-4-methylpyrrolidin-3-yl]acetic acid or a pharmaceutically acceptable salt thereof:

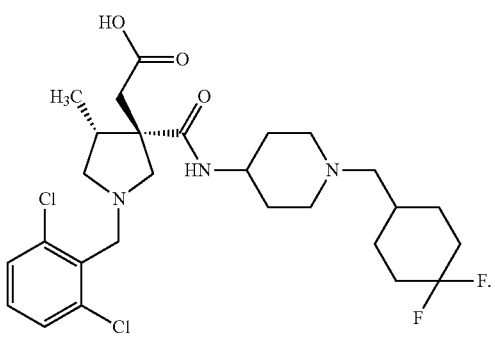 [SMILES: C[C@H]1CN(Cc2c(Cl)cccc2Cl)C[C@@]1(CC(=O)O)C(=O)NC1CCN(CC2CCC(F)(F)CC2)CC1]

10. 2-[(3S,4R)-1-{[2-Chloro-6-(trifluoromethyl)phenyl]methyl}-3-{[1-(cyclohex-1-en-1-ylmethyl)piperidin-4-yl]carbamoyl}-4-methylpyrrolidin-3-yl]acetic acid or a pharmaceutically acceptable salt thereof:

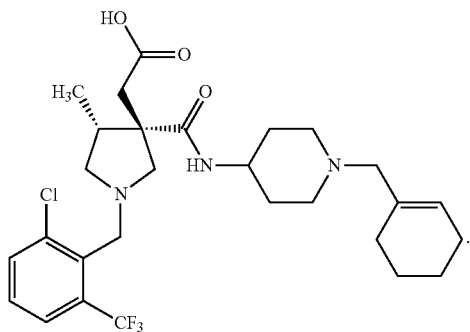

11. 2-[(3S,4R)-1-[(2-Chloro-6-methylphenyl)methyl]-3-{[1-(cyclohex-1-en-1-ylmethyl)piperidin-4-yl]carbamoyl}-4-methylpyrrolidin-3-yl]acetic acid or a pharmaceutically acceptable salt thereof:

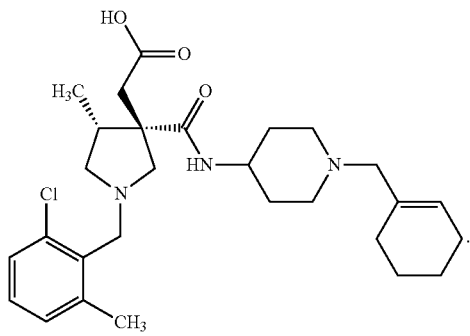 [SMILES: C[C@H]1CN(Cc2c(Cl)cccc2C(F)(F)F)C[C@@]1(CC(=O)O)C(=O)NC1CCN(CC2=CCCCC2)CC1]

12. 2-[(3S,4R)-1-{[2-Chloro-6-(trifluoromethyl)phenyl]methyl}-3-{[1-(cyclopent-1-en-1-ylmethyl)piperidin-4-yl]carbamoyl}-4-methylpyrrolidin-3-yl]acetic acid or a pharmaceutically acceptable salt thereof:

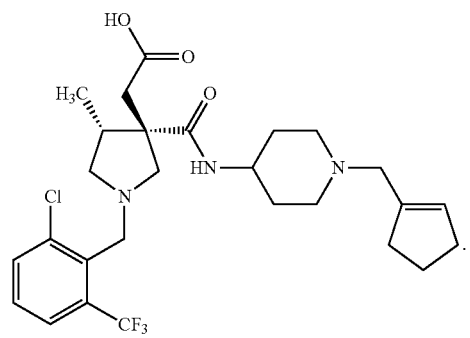 [SMILES: C[C@H]1CN(Cc2c(Cl)cccc2C(F)(F)F)C[C@@]1(CC(=O)O)C(=O)NC1CCN(CC2=CCCC2)CC1]

13. 2-[(3S,4R)-1-[(2-Chloro-6-methylphenyl)methyl]-3-{[(1-cyclopent-1-en-1-ylmethyl)piperidin-4-yl]carbamoyl}-4-methylpyrrolidin-3-yl]acetic acid or a pharmaceutically acceptable salt thereof:

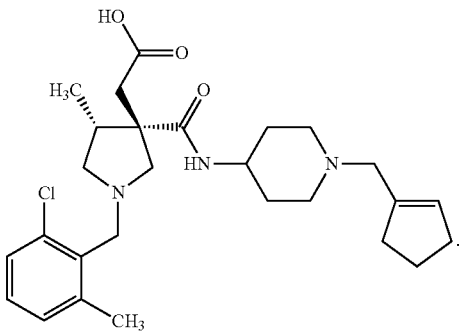 [SMILES: Cc1cccc(Cl)c1CN1C[C@H](C)[C@](CC(=O)O)(C(=O)NC2CCN(CC3=CCCC3)CC2)C1]

14. 2-[(3S,4R)-3-{[(3S)-1-(Cyclohex-1-en-1-ylmethyl)pyrrolidin-3-yl]carbamoyl}-1-[(2,6-dichlorophenyl)methyl]-4-methylpyrrolidin-3-yl]acetic acid or a pharmaceutically acceptable salt thereof:

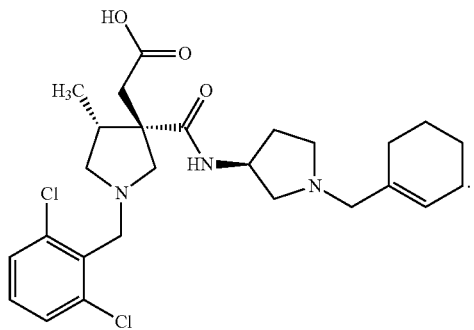 [SMILES: C[C@H]1CN(Cc2c(Cl)cccc2Cl)C[C@@]1(CC(=O)O)C(=O)N[C@H]1CCN(CC2=CCCCC2)C1]

15. 2-[(3S,4R)-3-{[(1-Cyclohex-1-en-1-ylmethyl)piperidin-4-yl]carbamoyl}-1-[(2,6-dichlorophenyl)methyl]-4-methylpyrrolidin-3-yl]acetic acid or a pharmaceutically acceptable salt thereof:

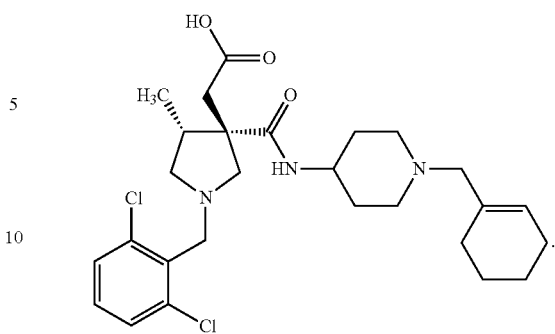

16. A method for treating an inflammatory bowel disease comprising administering the compound or pharmaceutically acceptable salt thereof according to claim 1 to a patient in need thereof.

17. The method according to claim 16, wherein the inflammatory bowel disease is ulcerative colitis.

18. A method for inhibiting the fractalkine-CX3CR1 pathway comprising administering the compound or pharmaceutically acceptable salt thereof according to claim 1 to a patient in need thereof.

19. A method for inhibiting fractalkine comprising administering the compound or pharmaceutically acceptable salt thereof according to claim 1 to a patient in need thereof.

20. A method for inhibiting CX3CR1 comprising administering the compound or pharmaceutically acceptable salt thereof according to claim 1 to a patient in need thereof.

21. The method according to claim 16, wherein the inflammatory bowel disease is Crohn's disease.

22. A method for treating an inflammatory bowel disease comprising administering the compound or pharmaceutically acceptable salt thereof according to claim 7 to a patient in need thereof.

23. The method according to claim 22, wherein the inflammatory bowel disease is ulcerative colitis.

24. The method according to claim 22, wherein the inflammatory bowel disease is Crohn's disease.

\* \* \* \* \*